(12) United States Patent
Cable, Jr. et al.

(10) Patent No.: US 8,348,537 B2
(45) Date of Patent: Jan. 8, 2013

(54) MEDICAL SKIN APPLICATOR APPARATUS

(75) Inventors: Frank A. Cable, Jr., Amherst, MA (US);
Mark Tauer, Belchertown, MA (US);
Andrew Fetterroll, Springfield, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/370,335

(22) Filed: Feb. 10, 2012

(65) Prior Publication Data

US 2012/0143153 A1 Jun. 7, 2012

Related U.S. Application Data

(60) Continuation of application No. 12/839,795, filed on Jul. 20, 2010, now Pat. No. 8,113,731, which is a division of application No. 11/200,460, filed on Aug. 8, 2005, now Pat. No. 7,866,907.

(60) Provisional application No. 60/599,927, filed on Aug. 9, 2004, provisional application No. 60/614,503, filed on Sep. 30, 2004, provisional application No. 60/639,182, filed on Dec. 22, 2004.

(51) Int. Cl.
*B43K 5/14* (2006.01)
(52) U.S. Cl. .............................. 401/134; 604/3; 401/133
(58) Field of Classification Search .......... 401/132–135; 604/2–3
See application file for complete search history.

(56) References Cited

U.S. PATENT DOCUMENTS

| | | | |
|---|---|---|---|
| 2,976,560 A | 3/1961 | Turner | |
| 2,998,822 A | 9/1961 | Birch et al. | |
| 3,324,855 A | 6/1967 | Heimlich et al. | |
| 3,399,020 A | 8/1968 | Margolis et al. | |
| 3,519,364 A * | 7/1970 | Truhan | 401/177 |
| 3,601,287 A | 8/1971 | Schwartzman | |
| 3,635,922 A | 1/1972 | Ketner | |
| 3,891,331 A | 6/1975 | Avery | |
| 4,084,910 A | 4/1978 | LaRosa | |
| 4,140,409 A | 2/1979 | DeVries | |
| 4,148,318 A | 4/1979 | Meyer | |
| 4,173,978 A | 11/1979 | Brown | |
| 4,183,684 A | 1/1980 | Avery, Jr. | |
| 4,201,491 A | 5/1980 | Kohler | |
| 4,225,254 A | 9/1980 | Holberg et al. | |
| 4,415,288 A | 11/1983 | Gordon et al. | |
| 4,498,796 A | 2/1985 | Gordon et al. | |
| 4,507,111 A | 3/1985 | Gordon et al. | |
| 4,578,055 A | 3/1986 | Fischer | |
| 4,863,422 A | 9/1989 | Stanley | |

(Continued)

FOREIGN PATENT DOCUMENTS

WO  WO 95/03734  2/1995

(Continued)

*Primary Examiner* — David Walczak
*Assistant Examiner* — Jennifer C Chiang
(74) *Attorney, Agent, or Firm* — Lisa E. Winsor

(57) ABSTRACT

A medical skin applicator apparatus includes a fluid housing having a fluid chamber for storing a medical agent and an applicator coupled to the housing. The fluid housing has a penetrable wall to permit access to the fluid chamber and release of the medical agent therefrom. The applicator includes an applicator surface for applying the medical agent to a patient. The applicator has a penetrating member adapted to penetrate the penetrable wall of the fluid housing upon achieving a predetermined coupled relation of the fluid housing and the applicator, to thereby permit the medical agent to be dispensed from the fluid chamber and applied to the patient with the applicator surface.

11 Claims, 57 Drawing Sheets

U.S. PATENT DOCUMENTS

| | | | |
|---|---|---|---|
| 4,925,327 A | 5/1990 | Wirt | |
| 5,006,004 A | 4/1991 | Dirksing et al. | |
| 5,015,228 A | 5/1991 | Columbus et al. | |
| 5,019,033 A | 5/1991 | Geria | |
| 5,088,849 A | 2/1992 | Johnson et al. | |
| 5,147,337 A | 9/1992 | Plone | |
| 5,288,159 A | 2/1994 | Wirt | |
| 5,308,180 A | 5/1994 | Pournoor et al. | |
| 5,435,660 A | 7/1995 | Wirt | |
| 5,445,462 A | 8/1995 | Johnson et al. | |
| 5,489,280 A | 2/1996 | Russell | |
| 5,509,744 A | 4/1996 | Frazier | |
| 5,568,988 A * | 10/1996 | Knox et al. | 401/40 |
| 5,658,084 A * | 8/1997 | Wirt | 401/132 |
| 5,713,843 A | 2/1998 | Vangsness | |
| 5,769,552 A * | 6/1998 | Kelley et al. | 401/132 |
| 5,775,826 A | 7/1998 | Miller | |
| 5,791,801 A | 8/1998 | Miller | |
| 5,871,297 A | 2/1999 | Rogers et al. | |
| 5,908,256 A | 6/1999 | Bernstein | |
| 5,934,296 A | 8/1999 | Clay | |
| 6,190,367 B1 | 2/2001 | Hall | |
| 6,238,117 B1 | 5/2001 | Griebel et al. | |
| 6,371,675 B1 | 4/2002 | Hoang et al. | |
| 6,422,778 B2 | 7/2002 | Baumann et al. | |
| 6,471,095 B1 | 10/2002 | Cann | |
| 6,475,701 B2 | 11/2002 | Ohno et al. | |
| 6,488,665 B1 * | 12/2002 | Severin et al. | 604/200 |
| 6,505,985 B1 | 1/2003 | Hidle et al. | |
| 6,533,484 B1 * | 3/2003 | Osei et al. | 401/205 |
| 6,536,975 B1 | 3/2003 | Tufts | |
| 6,595,696 B1 | 7/2003 | Zellak | |
| 6,616,363 B1 | 9/2003 | Guillaume et al. | |
| 6,672,784 B2 | 1/2004 | Baumann et al. | |
| 6,689,103 B1 | 2/2004 | Palasis | |
| 6,729,786 B1 * | 5/2004 | Tufts et al. | 401/133 |
| 6,743,211 B1 | 6/2004 | Prausnitz et al. | |
| 6,755,586 B1 | 6/2004 | Frazier | |
| 6,805,682 B1 | 10/2004 | Campbell | |
| 6,811,341 B2 | 11/2004 | Crane | |
| 6,869,242 B2 | 3/2005 | May | |
| 6,909,339 B2 | 6/2005 | Yonekura et al. | |
| 6,910,822 B2 | 6/2005 | Hidle et al. | |
| 6,916,133 B2 | 7/2005 | Hoang et al. | |
| 6,916,137 B2 | 7/2005 | Shiraiwa | |
| 6,991,394 B2 | 1/2006 | Tufts et al. | |
| 7,090,422 B2 | 8/2006 | Baumann et al. | |
| 7,201,525 B2 | 4/2007 | Mohiuddin | |
| 7,261,701 B2 * | 8/2007 | Davis et al. | 604/3 |
| 2001/0055511 A1 | 12/2001 | Baumann et al. | |
| 2002/0076255 A1 | 6/2002 | Hoang et al. | |
| 2002/0076258 A1 | 6/2002 | Crosby et al. | |
| 2003/0049069 A1 | 3/2003 | Osei et al. | |
| 2003/0060746 A1 | 3/2003 | Mark | |
| 2003/0068190 A1 | 4/2003 | Hidle et al. | |
| 2003/0118629 A1 | 6/2003 | Scholz et al. | |
| 2003/0149106 A1 | 8/2003 | Mosbey et al. | |
| 2003/0194447 A1 | 10/2003 | Scholz et al. | |
| 2004/0068218 A1 | 4/2004 | Davis et al. | |
| 2004/0162533 A1 | 8/2004 | Alley | |
| 2004/0179888 A1 | 9/2004 | Tufts et al. | |
| 2004/0240927 A1 | 12/2004 | Hoang et al. | |
| 2004/0267182 A1 | 12/2004 | Davis et al. | |

FOREIGN PATENT DOCUMENTS

| | | |
|---|---|---|
| WO | WO 00/10889 | 3/2000 |
| WO | WO 2004/062709 | 7/2004 |

* cited by examiner

MEDICAL SKIN APPLICATOR APPARATUS

CROSS-REFERENCE TO RELATED APPLICATIONS

This application is a continuation application under 35 U.S.C. §120 of and claims priority to and the benefit of co-pending U.S. application Ser. No. 12/839,795, filed Jul. 20, 2010, which is a divisional application under 35 U.S.C §121 of and claims priority to and the benefit of U.S. application Ser. No. 11/200,460, filed Aug. 8, 2005, (now U.S. Pat. No. 7,866,907) which claims priority to and the benefit of U.S. Provisional Application Ser. No. 60/639,182, filed Dec. 22, 2004, U.S. Provisional Application Ser. No. 60/614,503, filed Sep. 30, 2004 and U.S. Provisional Application Ser. No. 60/599,927, filed Aug. 9, 2004, the entire contents of which are incorporated herein by reference.

BACKGROUND

1. Technical Field

The present disclosure relates generally to medical skin applicators, and more particularly, to a skin applicator apparatus adapted to uniformally and consistently dispense sterilizing fluid to a skin surface of a patient.

2. Description of the Related Art

Many medical procedures involve application of medicines, sterilizing fluids, antiseptics, gels, agents or other materials to portions of the body, such as the skin, for preparation, treatment, etc. Such medicines, sterilizing fluids, agents are typically transferred to the skin via an applicator. Conventional liquid applicators incorporate a glass ampoule or plastic blow-molded bottles for storing the liquid and a mechanism for fracturing the ampoule to release the stored liquid. The released liquid contacts a swab, foam pad or tip for application to the skin.

However, numerous problems are encountered with applicators of this type. Fracture of the glass ampoule generates shards within the applicator that may pose risks to a patient. Attempts to overcome these potential risks include devices that employ screens or foam to contain the glass shards. However, there still exists a possibility of introducing these shards into the fluid pathway, which poses an unacceptable and unnecessary risk to the patient.

Another drawback of the above mentioned devices is the permeation of certain gases through the seals of bottles as well as the plastic of the bottle. Ethylene oxide (EO) migrates through most plastics at the thicknesses used for blow molding containers (0.040" or less) and forms toxic by-products when allowed to react with certain antiseptic products, most notably chlorhexidine gluconate (CHG). Manufacturers have devised methods to eliminate permeation such as packaging in glass ampoules or by employing plastics with gas barrier properties such as polyethylene terephthalate (PET). PET greatly reduces permeation when a sufficient cross-section is provided in the package; however the current devices employ blow molded containers in combination with conventional caps. The caps therefore become the weakest part of these systems and oftentimes leak due to inconsistent sealings (PET/foil) or due to cap loosening due to the pressure imparted during the EO sterilization process.

The current devices mentioned above employ either a glass blow or molded plastic container with a thickness of or less than 0.030". This minimal thickness allows for considerable permeation of EO through the wall of the container during sterilization. Additionally, the current devices use blow-molded containers that during manufacture are pinched off at the openings or cut via a spindle and knife apparatus. The result is a sharp, uneven and irregular top surface to the container, which is problematic when a seal is applied to the non-uniform surface and an irregular seal is formed.

Additionally, current container designs utilize conventional, single weld innerseals as a means of sealing the bottle contents. The size of the bottle cap and force with which it is tightened on the bottle therefore becomes critical to maintenance of the force needed to mechanically reinforce the foil over time. The loosening of the cap is a common failure and oftentimes results in leakage of the bottle contents—especially when the system is pressurized or is required to remain in storage for long periods prior to use.

Finally current devices suffer from control of the contained fluid due to their design. Ampulized applicators rely upon low viscosity fluid of less than 200 centipoise due to the small orifice associated with the ampule after fracture. Fluids of higher viscosity do not readily flow out of standard ampule designs when inverted. These lower viscosity fluids however require metering features within the applicator, especially when smaller (less than 4 sq. in.) sponges are used. Inevitably these lower viscosity fluids result in loss of fluid control once dispensed to the patient's skin which poses an unnecessary risk of fire due to the associated pooling of alcohol within surgical drapes.

Alternate embodiments have attempted to address this issue by adding gel components into the antiseptic resulting in a 100 fold increase in the viscosity (2,000 centipoise) or higher. These devices suffer an inability of the fluid to migrate to the sponge dispensing means.

Therefore it would be highly desirable to overcome these disadvantages relating to fluid control and viscosity with a device that contained an antiseptic that would flow readily under gravity (400-700 centipoise) thereby eliminating the need for compression of the handle element in combination with an absorbent member, e.g., sponge design, that contained sufficient fluid capacity such that little to no pooling of the antiseptic fluid would result.

Therefore, it would be desirable to overcome the disadvantages and drawbacks of the prior art with a medical skin applicator including a fluid container having a penetrable surface that is engageable with a piercing member to facilitate fluid communication with a dispensing member of the skin applicator thereby enabling preparation and treatment of a skin surface of a patient. It would be desirable if the skin applicator can be disposed in an inverted orientation during use. Such a skin applicator may also accommodate multiple combinations of sterilizing agents and applicator head designs. It would be highly desirable if the medical skin applicator and its constituent parts are easily and efficiently manufactured and assembled.

SUMMARY

In accordance with a preferred embodiment of the present disclosure, a medical skin applicator apparatus includes a fluid housing having a fluid chamber for storing a medical agent, and a penetrable wall to permit access to the fluid chamber and release of the medical agent therefrom, and an applicator coupled to the fluid housing. The applicator includes an applicator surface for applying the medical agent to a patient. The applicator has a penetrating member adapted to penetrate the penetrable wall of the fluid housing upon achieving a predetermined coupled relation of the fluid housing and the applicator, to thereby permit the medical agent to be dispensed from the fluid chamber and applied to the patient with the applicator surface. The fluid housing is adapted to move relative to the applicator from a first transit position to a second actuated position to cause penetration of the penetrating member with the penetrable wall and to establish the predetermined coupled relation thereof.

The fluid housing may include an end cap mounted adjacent the penetrating wall. The end cap preferably defines an open portal to permit the penetrating member to pass therethrough and penetrate the penetrable wall of the fluid housing upon movement of the fluid housing to the second actuated position. The end cap may include at least one retaining member mounted along an outer surface thereof The at least one retaining member is received within a locking recess associated with the applicator upon movement of the fluid housing to the second actuated position to retain the fluid housing in the second actuated position. The at least one retaining member includes a locking tab which is received within a corresponding channel in the dispenser. The locking tab is adapted to traverse the channel during movement of the fluid housing to the second actuated position for reception within the locking recess. Additional means for retaining the fluid housing in the second actuated position is also envisioned.

The applicator may include at least two penetrating members. A first penetrating member is dimensioned and positioned to penetrate the penetrable wall in a first location to allow egress of the medical agent from the fluid chamber. A second penetrating member of the at least two penetrating members is dimensioned and positioned to penetrate the penetrable wall in a second location spaced from the first location to allow air ingress to the fluid chamber. In the alternative, the at least two penetrating members are adapted to divide the penetrable wall into wall portions. The at least two penetrating members may be coaxially arranged about an axis in spaced relation. Four penetrating members are provided to divide the penetrable wall into quadrant portions. In a further alternative, the penetrating member is arranged in an annular array of, e.g., a plurality of penetrating members to form a substantially annular opening within the penetrable wall.

In one preferred embodiment, at least one of the fluid housing and the applicator includes an internal member. The internal member is positioned to engage a wall portion defined within the opening of the penetrable wall to displace the wall portion during movement of the fluid housing to the second actuated position. The internal member is an internal wall within the fluid housing. The internal wall extends in a general longitudinal direction and is positioned to rotate the wall portion of the penetrable wall during movement of the fluid housing to the second actuated position thereof. Preferably, an internal wall is also within the applicator. The internal wall extends in a general longitudinal direction and within the annular array, and is positioned to cooperate with the internal wall of the fluid housing to rotate the penetrable wall.

The applicator includes an applicator frame and an absorbent member mounted to a lower surface of the applicator frame. The applicator includes a relative enlarged section and a relative narrow prow section depending from the enlarged section. The prow section includes opposed generally concave surfaces extending to a leading surface which interconnects the concave surfaces. The leading surface is preferably arcuate. The enlarged section includes opposed generally convex surfaces extending from a trailing surface which interconnects the convex surfaces. Alternatively, the applicator defines a complex curve configuration in plan. The complex curve configuration includes a pair of opposed generally convex surfaces and a pair of opposed generally concave surfaces extending contiguously from the convex surfaces to a leading surface.

The fluid housing is preferably adapted for longitudinal movement to move from the first transit position to the second actuated position. The fluid housing may also be adapted for rotational movement relative to the applicator to release the fluid housing to permit movement thereof toward the second actuated position. One of the fluid housing and the applicator may include a locking tab and the other of the fluid housing and the applicator include a locking recess for cooperating with the locking tab to selectively lock the fluid housing and the applicator in the second actuated position.

An outer housing may be provided for at least partially accommodating the fluid housing. The outer housing is mountable to the applicator. The fluid housing is adapted for longitudinal movement within the outer housing. A manually engageable member is connected to the fluid housing and extends beyond the outer housing. The manually engageable member is depressible to cause longitudinal movement of the fluid housing to the second actuated position. The manually engageable member may include a locking member which is received within a corresponding locking recess in the outer housing to releasably retain the fluid housing in the first transit position. The locking member of the manually engageable member may include a deflectable tab. The deflectable tab is movable from the locking recess to release the manually engageable member and permit movement of the fluid housing to the second position thereof Means for securing the fluid housing in the second position is also provided. In one arrangement, the outer housing includes a locking recess adapted to receive the deflectable tab to secure the fluid housing in the second position.

In another preferred embodiment, the manually engageable member includes a locking tab releasably mounted thereto. The locking tab selectively secures the fluid housing in the first transit position and is removable to permit the manually engageable member to be advanced to move the fluid housing to the second actuated position.

In another preferred embodiment, the applicator frame of the applicator includes a conduit for passage of the medical agent from the fluid chamber to the absorbent member. The applicator frame includes a plurality of channels on the lower surface thereof in communication with the conduit. The channels are dimensioned to convey fluid along the lower surface and to the absorbent member. The applicator frame may include a plurality of arcuate channels defined in the lower surface thereof and in communication within the conduit for conveying fluid to the absorbent member. At least two of the arcuate channels are in general concentric arrangement. Alternatively, the channels of the applicator frame are in intersecting relation. The channels may define a general grid pattern on the lower surface of the applicator frame. As a further alternative, the applicator frame includes first and second substantially linear channels in the lower surface thereof and in intersecting relation, and in communication with the conduit for conveying fluid to the absorbent member.

The applicator frame preferably includes an enlarged opening extending through a lower surface thereof and in communication with the conduit. The opening conveys fluid to the absorbent member. A supplemental channel may be adjacent the enlarged opening and in communication with the conduit. The supplemental channel facilitates dispensing of the medical agent. Preferably, first and second supplemental channels are adjacent forward and rear ends of the applicator frame and in communication with the conduit for facilitating dispensing of the medical fluid. The first and/or second channels may serve as vents for release of air captured within the absorbent member.

The absorbent member may include at least one slit defined therein. The at least one slit is adapted to assume a substantially open condition upon application of pressure to the absorbent member to permit passage of the medical agent and assume a substantially closed condition in the absence of pressure to the absorbent member substantially preventing the medical agent to pass therethrough. Preferably, the absorbent member includes a plurality of spaced slits. Alternatively, the absorbent member includes a recessed channel defined in a lower surface thereof adapted to facilitate passage of the medical agent therethrough.

The penetrable wall may include one of a metal and a polymeric member connected to the fluid housing. Preferably, the penetrable wall includes a foil liner which is attached to the fluid housing. The foil liner may be attached to the fluid housing and to the end cap.

In one preferred embodiment, the outer housing and the fluid housing are arranged about a first longitudinal axis and the applicator is arranged about a second longitudinal axis displaced from the first longitudinal axis in a direction perpendicular to the applicator surface. The first axis of the fluid housing preferably is in general parallel relation to the second axis of the applicator.

A dye may positioned relative to the fluid housing. The dye contacts the medical agent upon release of the medical agent from the internal chamber of the fluid housing. The dye may be stored within the fluid housing in isolated relation from the medical agent whereby upon movement to the second actuated position, the penetrating member penetrates the penetrable wall to permit release of the medical agent and contact thereof with the dye. The fluid housing may include a second penetrable wall distal of the first-mentioned penetrable wall and having the dye stored therebetween whereby upon movement of the fluid housing to the second actuated position, the penetrating member penetrates the first mentioned penetrable wall and the second penetrable wall to permit respective release of the medical agent and the dye.

In another preferred embodiment, a medical skin applicator apparatus includes a fluid housing defining a longitudinal axis and having a fluid chamber for storing and selectively releasing a medical agent, and an applicator coupled to the fluid housing. The applicator includes an applicator surface in fluid communication with the fluid chamber for applying the medical agent to a patient. The applicator surface defines a configuration characterized by having a relatively enlarged portion and a relatively narrowed portion extending from the enlarged portion. The relatively narrowed portion includes opposed generally concave surfaces extending to a leading surface which interconnects the concave surfaces. The leading surface may be generally arcuate. The enlarged section includes opposed generally convex surfaces extending from a trailing surface which interconnects the convex surfaces. In the alternative, the applicator defines a complex curve configuration in plan. The complex curve configuration includes a pair of opposed generally convex surfaces and a pair of opposed generally concave surfaces extending contiguously from the convex surfaces to a leading surface.

A method of using a medical skin applicator apparatus is also disclosed. The method includes the steps of providing an applicator having a fluid housing that defines a fluid chamber and an applicator member for dispensing the fluid and actuating the applicator with a single hand to facilitate fluid communication between the chamber and the applicator member.

BRIEF DESCRIPTION OF THE DRAWINGS

The objects and features of the present disclosure are set forth with particularity in the appended claims. The present disclosure, both as to its organization and manner of operation, together with further objectives and advantages, may be best understood by reference to the following description, taken in connection with the accompanying drawings, as set forth below, wherein:

DETAILED DESCRIPTION OF THE EMBODIMENTS

The exemplary embodiments of the medical skin applicator apparatus and use(s) thereof are discussed in terms of medical skin applicators employed during medical procedures that involve application of sterilizing fluids, gels or agents to the skin of a body for preparation, treatment, etc. The skin applicator apparatus is advantageously configured to facilitate fluid communication of the sterilizing fluids with a skin contacting member or dispensing member of the skin applicator apparatus thereby enabling preparation and treatment of a skin surface of a patient. It is envisioned that the skin applicator apparatus may be employed in a range of medical procedures, such as, for example, surgical, diagnostic and related treatments of diseases and body ailments of a subject. It is further envisioned that the principles relating to the skin applicator apparatus disclosed include application of various agents to a body, such as, for example, medications and other fluids.

In the discussion that follows, the term "proximal" will refer to the portion of a structure that is closer to a practitioner, while the term "distal" will refer to the portion that is further from the practitioner or user. As used herein, the term "subject" refers to a human patient or other animal. According to the present disclosure, the term "practitioner" or "user" refers typically to a doctor, nurse or other care provider and may include support personnel.

The following discussion includes descriptions of the various embodiments of the skin applicator apparatus in accordance with the principles of the present disclosure followed by a description of uses of the apparatus.

Figure 1:
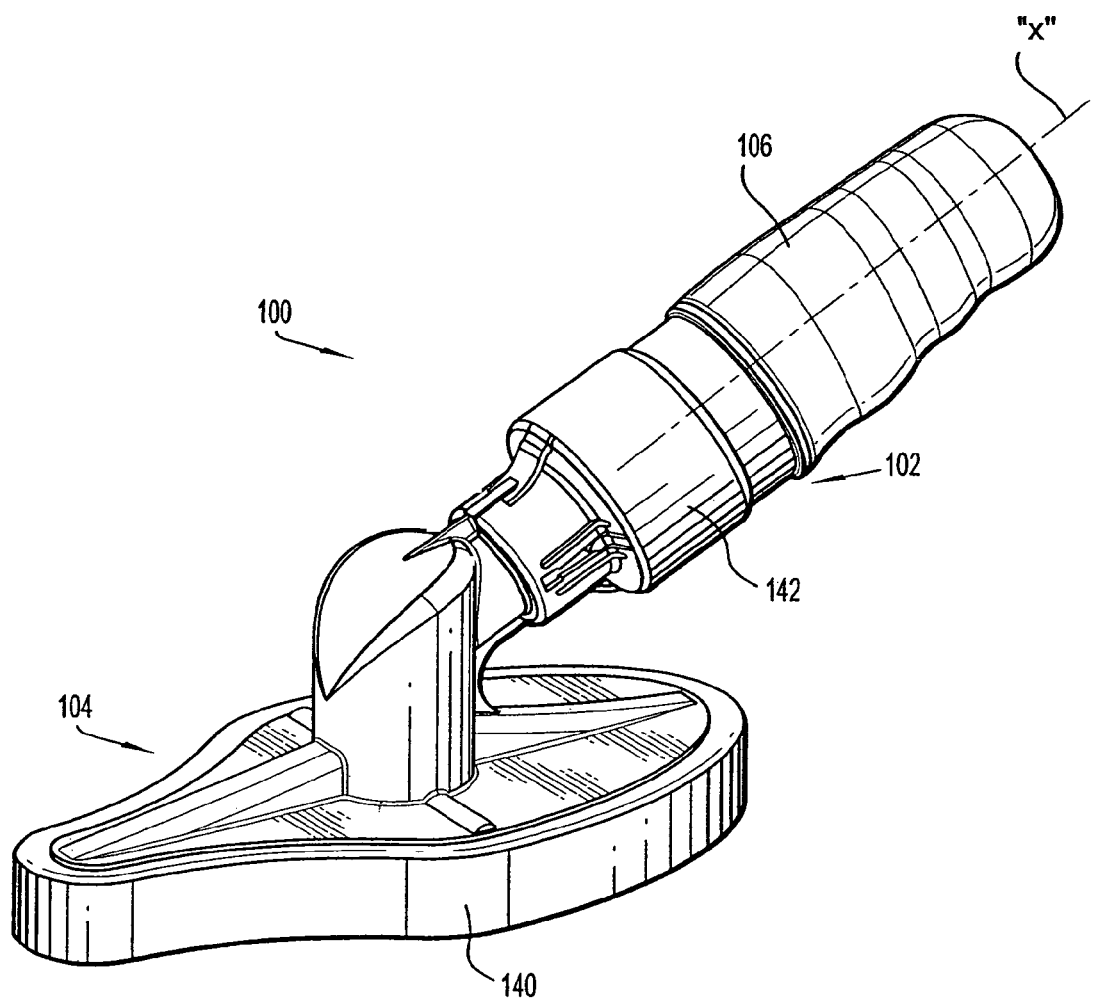
FIG. 1 is a perspective view of a medical skin applicator apparatus in accordance with the principles of the present disclosure illustrating the fluid container assembly and the applicator head assembly.
Figure 2:
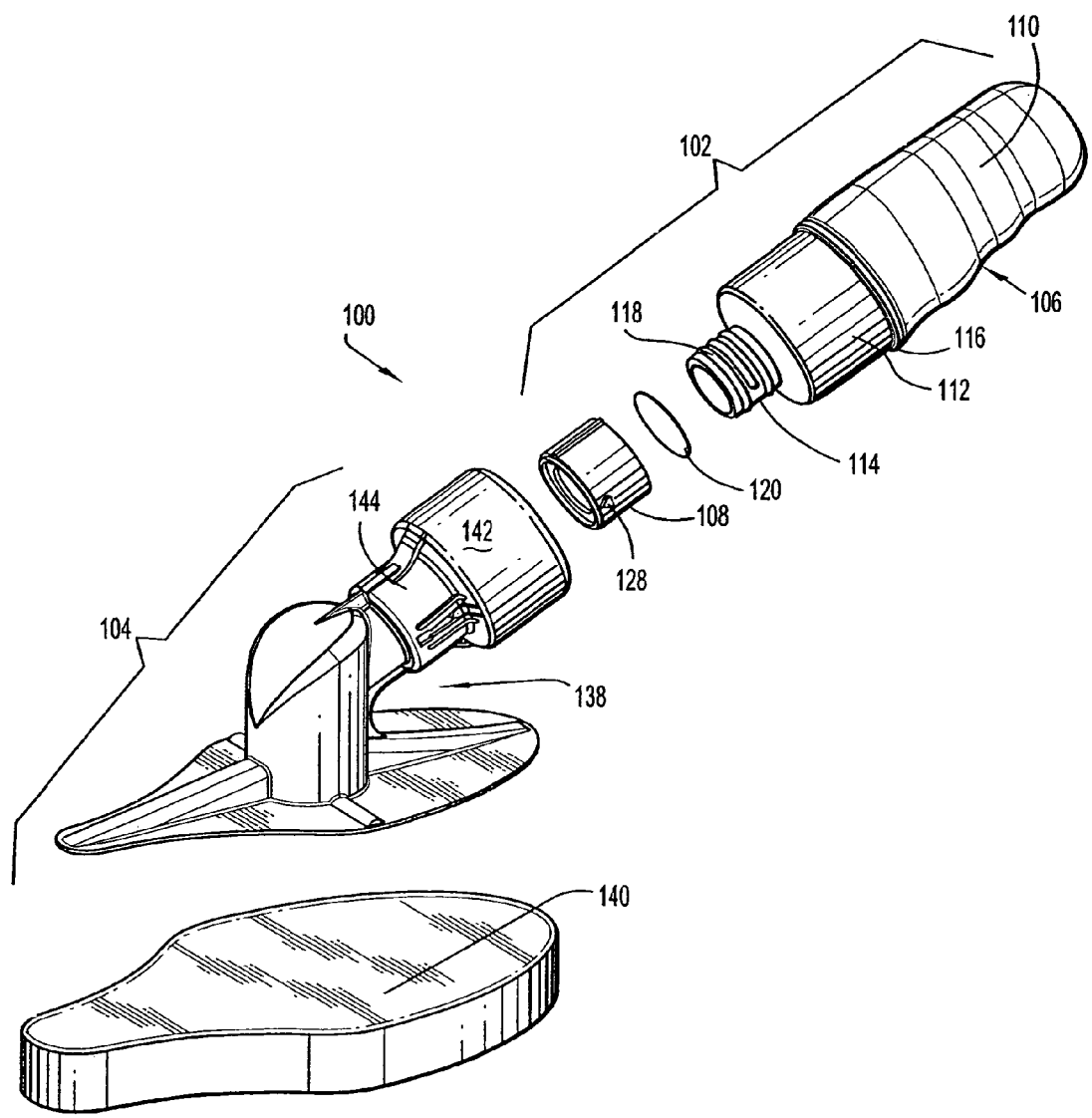
FIG. 2 is an exploded perspective view of the skin applicator apparatus of FIG. 1.
Figure 3:
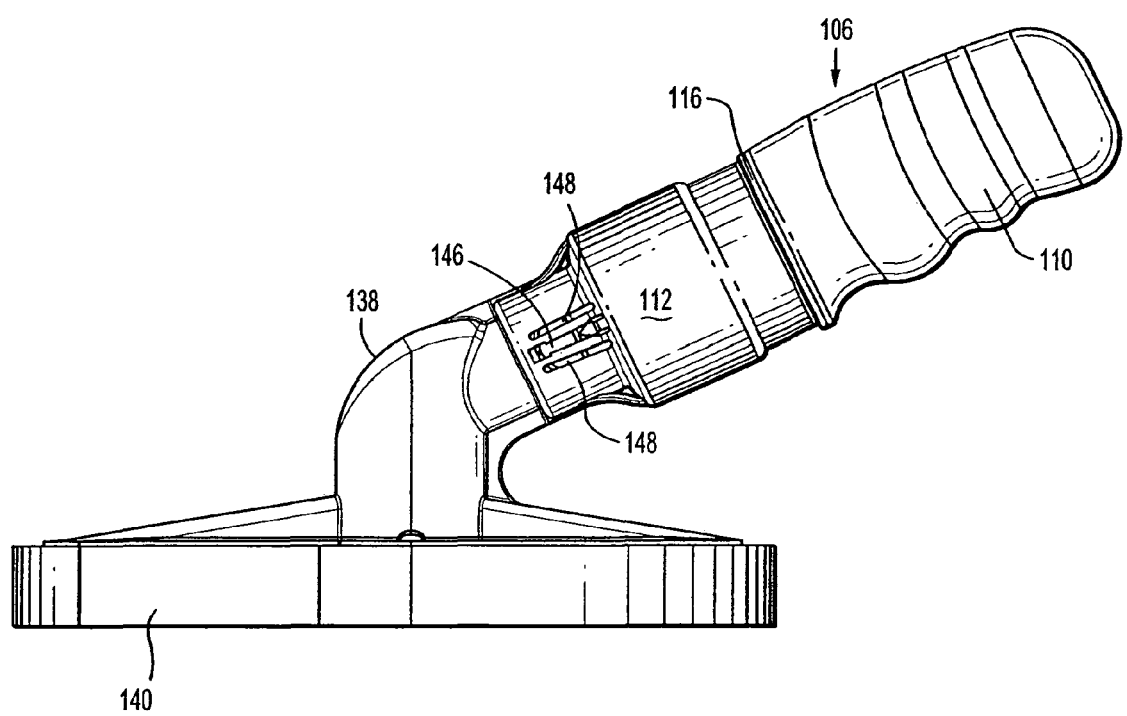
FIG. 3 is a side plan view of the skin applicator apparatus illustrating the fluid container assembly in a first transit position.
Figure 4:
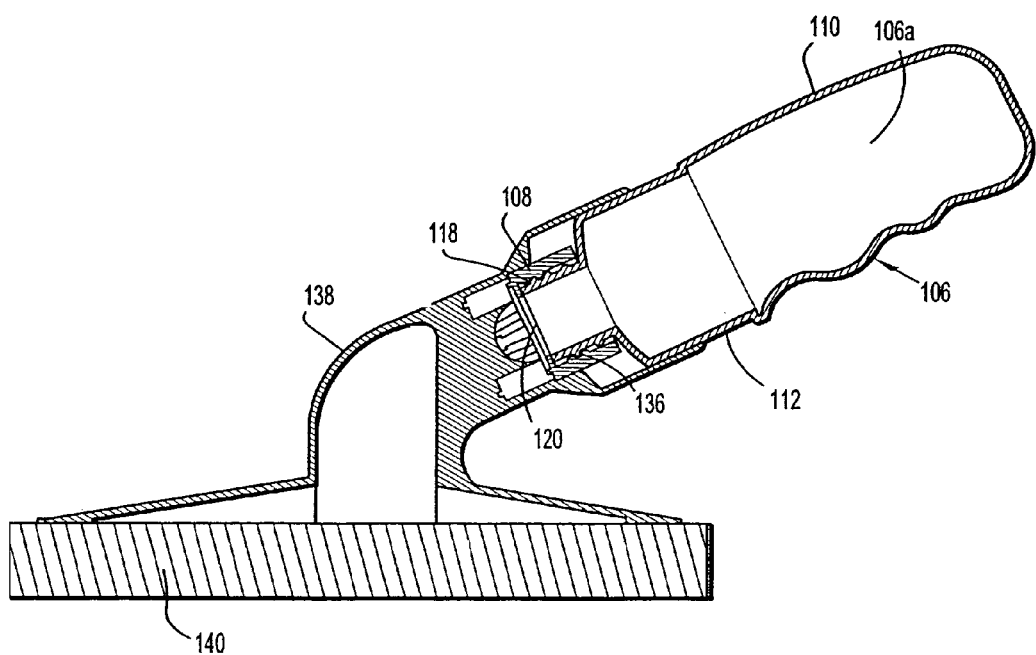
FIG. 4 is a side cross-sectional view of the skin applicator apparatus.

Referring now to the drawings wherein like components are designated by like references throughout the several views, FIGS. 1-3, in conjunction with the cross-sectional view of FIG. 4, illustrate the medical skin applicator apparatus in accordance with the principle of the present disclosure. Apparatus 100 includes two main assemblies, namely, fluid container assembly 102 and applicator head assembly 104 which is connected to the fluid container assembly 102. In general, fluid container assembly 102 is adapted for movement relative to applicator head assembly 104 from a first transit position to a second actuated position to dispense a medical agent or fluid for application to a patient. Fluid container assembly 102 includes fluid housing 106 defining housing axis "x", and end cap 108 which is releasably mountable to the fluid housing 106. Fluid housing 106 defines internal chamber 106a (FIG. 4) which is filled with a medicant, cleaning solution or the like. Such medicants are inclusive of antiseptic solutions, sterilizing solutions, etc., in liquid or in gel form. One suitable sterilization fluid is the sterilized liquid made under the tradename, Excel-AP, manufactured by Aplicare, Branford Conn. This liquid is comprised of 7.5% w/w available Iodine, 64.5% w/w Isopropanol and 25.3% USP sterile water among other proprietary ingredients.

Fluid housing 106 further defines handle section 110, cylindrical section 112 disposed distal of the handle section 110 and nipple section 114. Handle section 110 has a scalloped undersurface for facilitating gripping engagement by the user, specifically, with a single hand of the user. Cylindrical section 112 includes outer circumferential rib 116 defined at the juncture of the cylindrical section 112 and handle section 110. Circumferential 116 serves as a stop to properly position fluid container assembly 102 relative to applicator head assembly 104 upon actuation of apparatus 100. Nipple section 114 incorporates external thread 118.

Fluid housing 106, particularly, handle section 110, may be fabricated from a suitable flexible material to permit the handle section 110 to be compressed to expel the fluid. In one preferred embodiment, fluid housing 106 is fabricated from a suitable polymeric material such as polypropylene and is manufactured via conventional injection molding techniques. Other elastomeric materials are also envisioned.

Fluid housing 106 also includes a penetrable wall or surface in the form of, e.g., seal or liner 120, connected to the distal end surface of nipple section 114. Liner 120 may be a metallic or a polymeric material, and is attached to fluid housing 106 subsequent to filling the housing 106 with the medical liquid. In one preferred embodiment, liner 120 is a foil liner which is induction sealed to nipple 114 of fluid housing 106. In the alternative, liner 120 may be secured within end cap 108 and adapted to seal nipple 114 when the end cap 108 is mounted to fluid housing 106. Liner 120 may also be a double ply liner with one ply attached to end cap 108 and the other ply attached to nipple 114. In the alternative, liner 120 may be a spin welded plastic cap having a thin wall which is joined to nipple 114 via a spin weld or the like. A plastic cap may be required with antiseptic solutions containing alcohol. The plastic cap may have a selected notched geometry that provides a fracture point for the sharp point of the penetrating member to reduce the required puncture bore. Upon actuation of apparatus 100, liner 120 is punctured to permit release of the medical agent or liquid from fluid housing 106.

Figure 5:
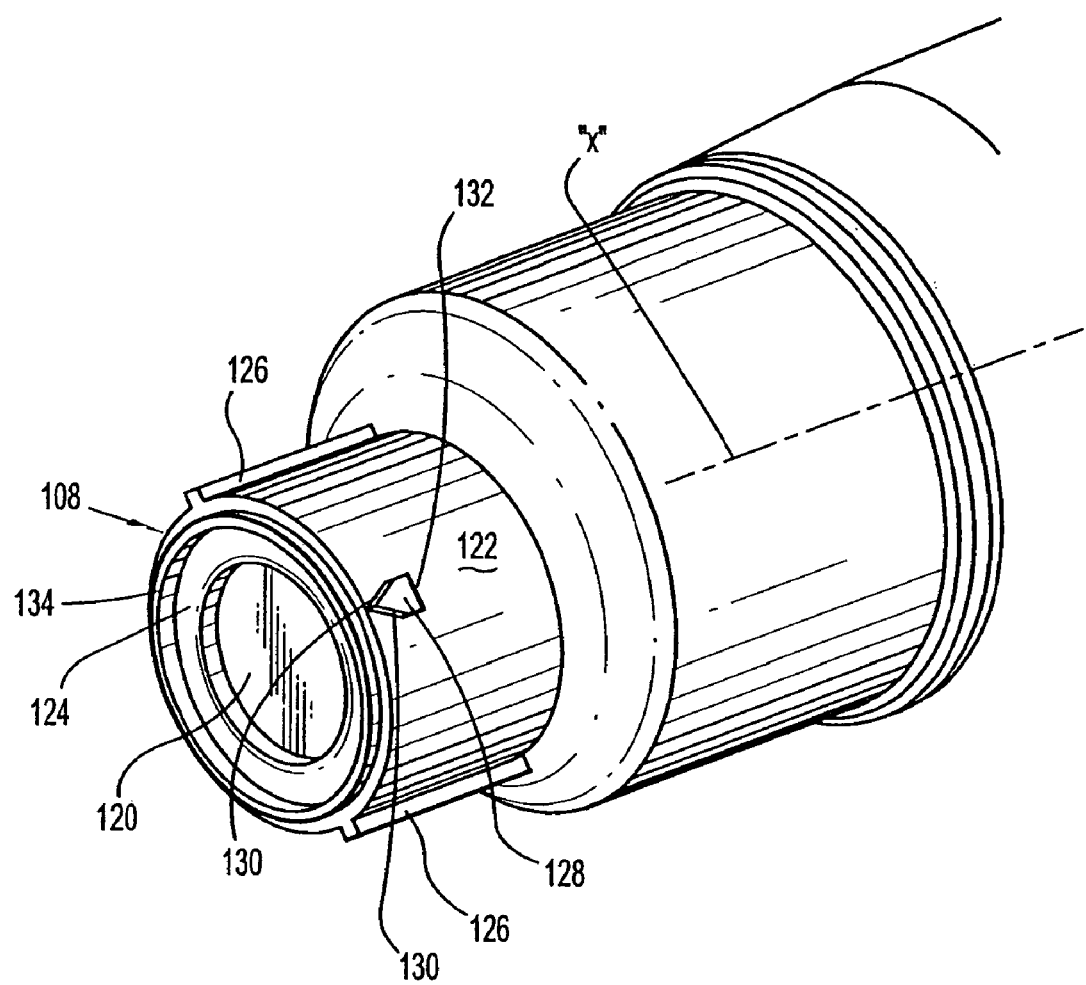
FIG. 5 is an enlarged perspective view illustrating the end cap mounted to the fluid housing of the fluid container assembly.

With reference now to FIGS. 4-5, in conjunction with FIG. 2, end cap 108 of fluid container assembly 102 will be discussed. End cap 108 is generally cylindrical in configuration and defines outer wall 122 and annular flange 124 disposed at the distal end of the outer wall in transverse relation to housing axis "x". Outer wall 122 incorporates a pair of axial guide ribs 126 disposed in diametrically opposed relation and extending along the axis "x" of fluid housing 106. Guide ribs 126 orient end cap 108 at a predetermined rotational position relative to applicator head assembly 104 and/or prevent the end cap 108 from rotating within applicator head assembly 104 upon assembly. Outer wall 122 of end cap 108 further possesses a pair of locking tabs 128 arranged in diametrical opposed relation approximately 90° displaced from guide ribs 126. Locking tabs 128 are each in the shape of a baseball plate having a leading v-shaped head with angled side surfaces 130 and transverse surface 132 contiguously extending from the v-shaped head. Locking tabs 128 secure fluid container assembly 102 in the second actuated position.

Annular flange 124 of end cap 108 defines central opening 132 which permits access to liner 120 attached to fluid housing 106. Annual flange 124 has peripheral rib 134 disposed about the periphery of the flange 124. Peripheral rib 134 extends a predetermined distance along the housing axis "x" and cooperates with corresponding structure within applicator head assembly 102 to form a fluid tight seal within apparatus 100 when the apparatus 100 is actuated. End cap 108 further defines internal thread 136. Internal thread 136 cooperates with external thread 118 of fluid housing 106 to mount the end cap 108 to the fluid housing 106.

Figure 6:
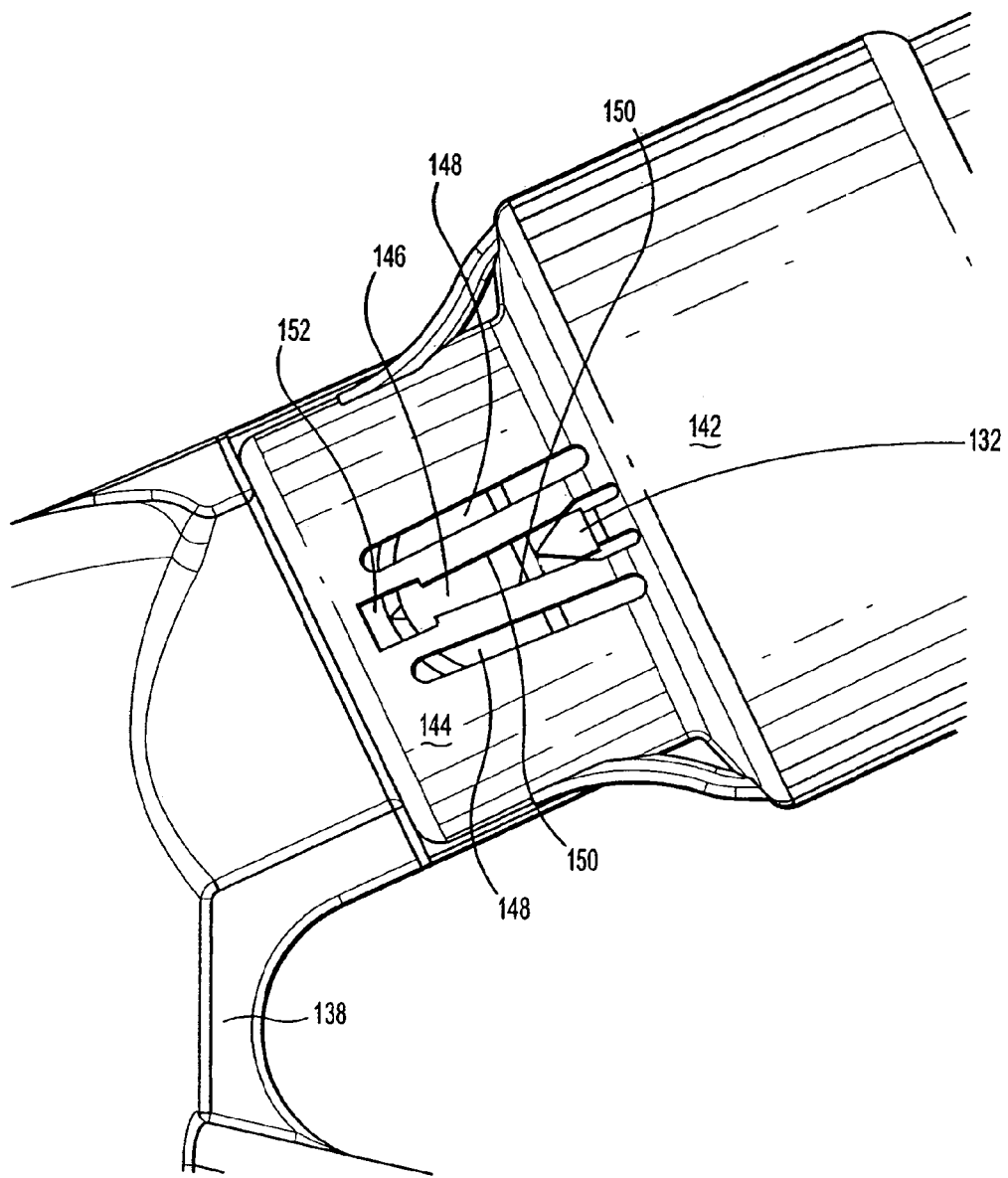
FIG. 6 is an enlarged side plan view illustrating the locking tabs of the end cap mounted within axial channels of the applicator head assembly.
Figure 7:
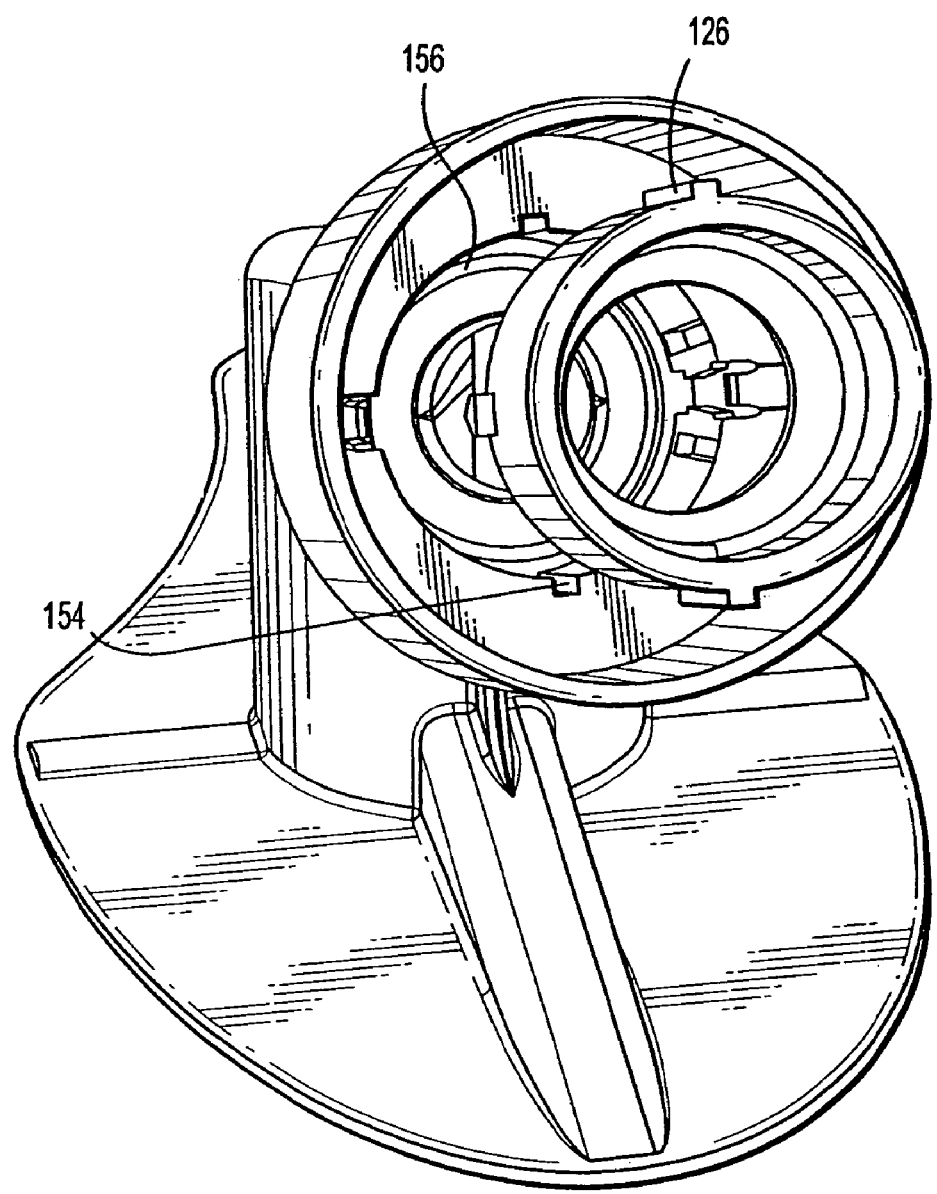
FIG. 7 is a perspective view illustrating mounting of the end cap within the applicator frame of the applicator head assembly.

Referring now to FIGS. 2-4, and the enlarged views of FIGS. 6-7, applicator head assembly 104 will be discussed. Applicator head assembly 104 includes applicator frame 138 and applicator member 140 (in the form of an absorbent member) which is mounted to the applicator frame 138. Applicator frame 138 incorporates housing support collar 142 at is proximal end and cap support collar 144 disposed distal of the housing support collar 142. Housing support collar 142 defines an internal cavity having a diameter which approximates the diameter of cylindrical section 112 of fluid housing 106 to receive the cylindrical section 112 during assembly. Similarly, cap support collar 144 defines an internal diameter or dimension which corresponds to the diameter of end cap 108. As depicted in FIGS. 6-7, cap support collar 144 further includes at least one, preferably, a pair of diametrically opposed axial channels 146 extending completely through its outer wall and longitudinal relief slots 148 on opposed sides of each axial channel 146. Axial channel 146 is defined by opposed cam surfaces 150 which extend in oblique relation to the housing axis "x" and terminate in locking recess 152. Axial channels 146 receive locking tabs 128 of end cap 108 and permit the locking tabs 128 to traverse the channels 146 during actuation of apparatus 10. The functionality of axial channels 146 and longitudinal slots 148 will be discussed in greater detail hereinbelow.

As best depicted in FIG. 7, cap support collar 144 further defines internal longitudinal grooves 154. Internal grooves 154 receive axial guide ribs 126 of end cap 108, which traverse the internal grooves 154 during actuation of the apparatus 108. Internal grooves 154 and axial guide ribs rotatably fix fluid container assembly 102 within applicator head assembly 104. Cap support collar 144 further defines annual groove 156 within the internal cavity of the support collar 144. Annual groove 156 is arranged in opposed relation to peripheral rib 134 of end cap 108 to receive the peripheral rib 134 during actuation of apparatus 100. Annular groove 156 and peripheral rib 134 are appropriately dimensioned to form a seal within the internal cavity of cap support collar 144 during actuation of the apparatus to substantially minimize migration of fluids back toward fluid housing 106.

Figure 8:
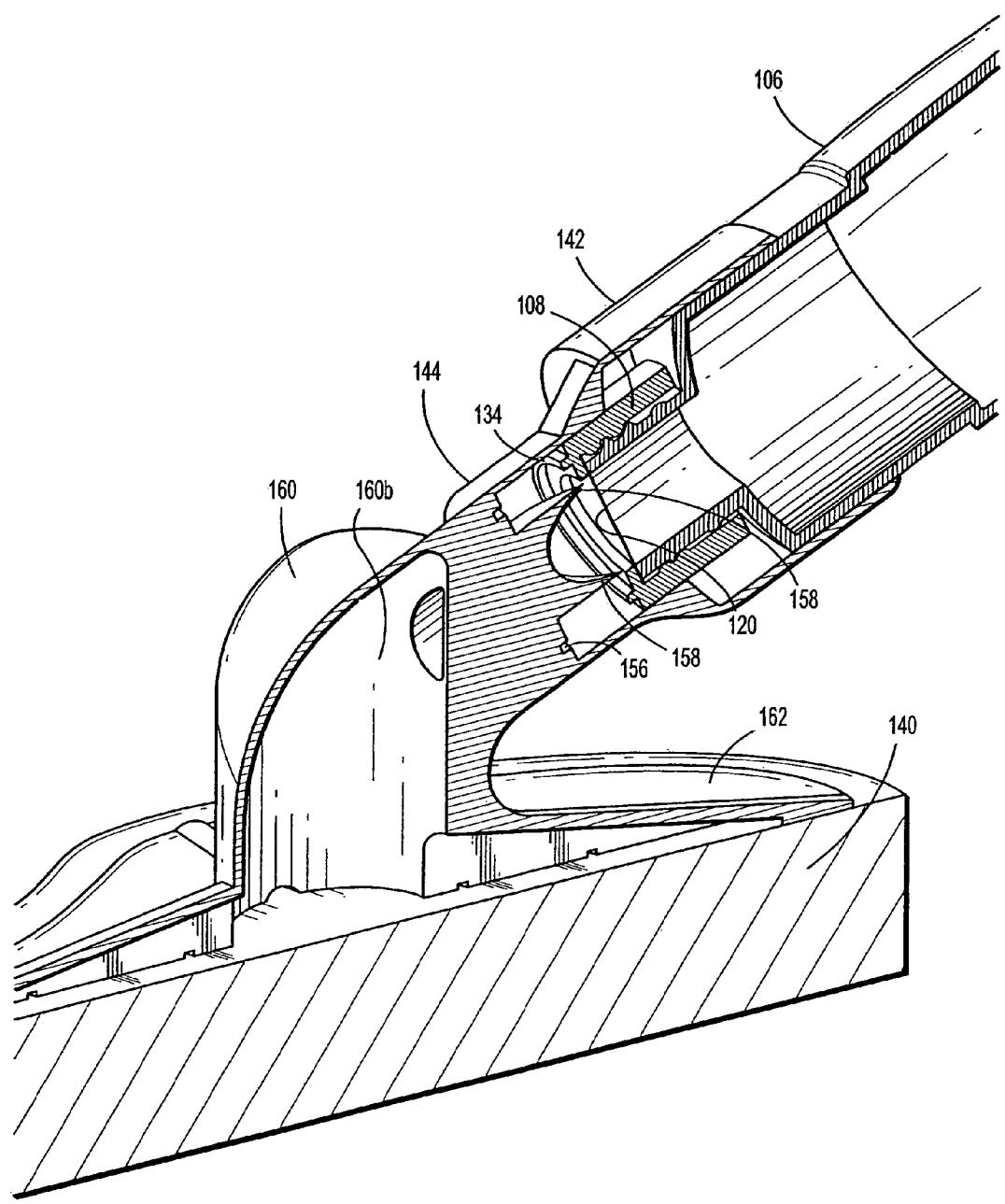
FIG. 8 is an enlarged perspective view in cross section illustrating the relationship of the end cap and the penetrating members of the applicator head assembly.

Referring now to FIG. 8, applicator frame 138 further defines a pair of piercing members or spikes 158 disposed within the interior of cap support collar 144. Piercing members 158 define sharpened tips which penetrate liner 120 during actuation of apparatus 100. Piercing members 158 are preferably spaced as shown. Two piercing members 158 are shown, however, it is appreciated that more or less than two piercing members 158 may be provided and still achieve the objectives of the present disclosure.

Figure 9:
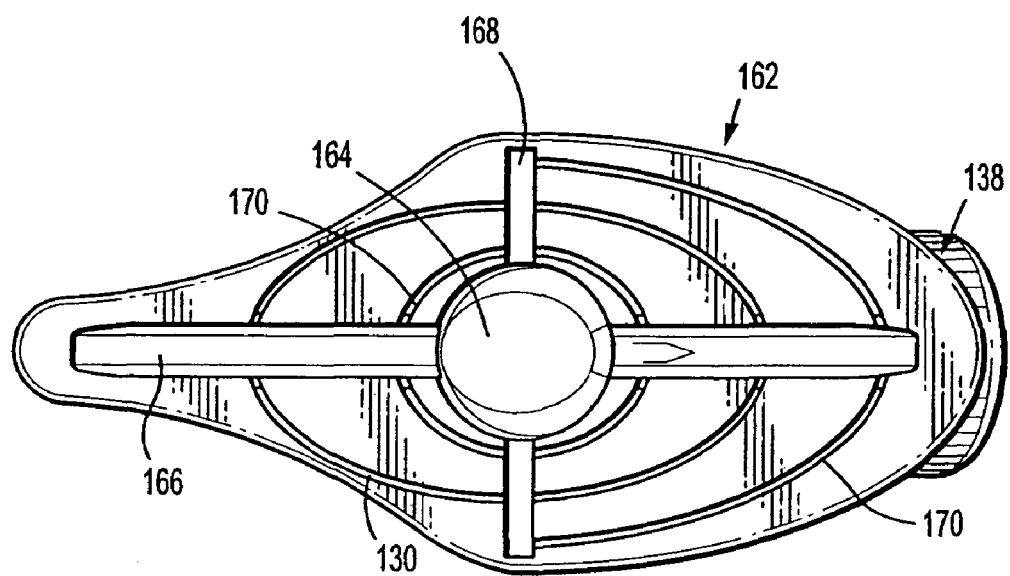
FIG. 9 is a plan view illustrating the lower surface of the applicator frame of the applicator head assembly.

Referring now to FIGS. 8-9, applicator frame 138 further includes throat 160 and applicator support plate 162 extending from the throat 160. Throat 160 defines internal bore 160b through which the medical agent or fluid released from fluid housing 106 flows to applicator member 140. Applicator support plate 162 supports applicator member 140. Support plate 162 includes central aperture 164 which is in communication with internal bore 160a of throat 160 and first and second channels 166, 168 disposed on the lower surface of the support plate (FIG. 9). Central aperture 164 is dimensioned to permit a relatively large volume of the medical agent or fluid to be dispersed therefrom and communicated through first and second channels 166, 168. First channel 166 extends in a general longitudinal direction and second channel 168 extends in transverse relation to the first channel 166. First channel 166 defines an enlarged width relative to second channel 168 and permits a sufficient volume of medical fluid to communicate with the extreme outer portions, i.e., the leading and trailing ends of, applicator frame 138. Applicator frame 138 may further define a plurality of radial or arcuate grooves 170 generally arranged in the concentric relation shown. Arcuate grooves 170 are in fluid communication with first and second channels 166, 168. Arcuate grooves 170 distribute the medical agent to substantially the entire surface of support plate 160 for delivery to applicator member 140. In this regard, the medical agent is uniformly applied to applicator member 140 through the fluid manifold defined within support plate 162 inclusive of first and second channels 166, 168, arcuate grooves 170 and central aperture 164, which consequently results in uniform application to the patient.

Applicator member 140 is mounted to support plate 162. Applicator member 140 preferably includes an absorbent member in the form of an open cell, reticulated urethane foam, 75 +/−10 pores/inch (ppi). Applicator member 140 may be adhered to support plate 160 with adhesives, welding or the like. Applicator member 140 is configured for transmission of the medical agent dispensed from fluid container assembly 102. The volume of absorbent member of applicator member 140 is proportioned to contain the full contents of the fluid container thereby acting as a fluid reservoir during application to the patient's skin. This capacity is used to control fluid release and minimize pooling of the antiseptic on the patient's skin.

Figure 10:
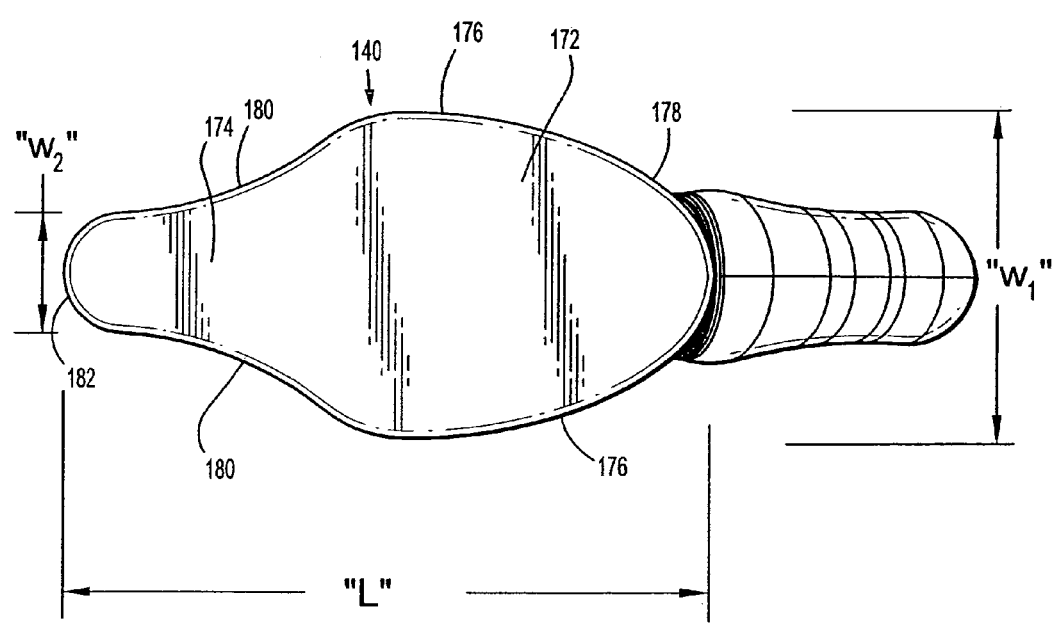
FIG. 10 is a plan view illustrating the configuration of the applicator member of the applicator head assembly.

As best depicted in FIG. 10 applicator member 140 defines a general tear-drop shaped or dolphin nosed configuration when viewed in plan. In particular, support plate 160 and applicator member 140 define an enlarged section 172 and an elongated neck or prow section 174 depending from the enlarged section 172. Enlarged section 172 is envisioned to facilitate application of medical fluid to relatively large body areas. Elongated neck section 174 is dimensioned to be-positioned in narrow remote areas such as the patient's fingers, toes, eye area etc. or in areas where only a relatively small amount of fluid is needed. Enlarged section 172 includes opposed generally convex surfaces 176 interconnected by arcuate trailing surface 178. In one preferred embodiment, enlarged section 172 defines a partial ellipse having a maximum width "w" of about 2 inches to about 4 inches. Elongated neck or prow section 174 defines opposed concave surfaces 180 extending contiguously from convex surfaces 176 of enlarged section 172, which lead to leading arcuate surface 182 interconnecting the concave surfaces 180. The arcuate configuration of concave surfaces 180 facilitates manipulation of apparatus 100 about the fingers, toes, etc. of the patient. In particular, the curvature of concave services 180 generally conforms to the curvature of various parts of the anatomy whereby applicator member 140 can be applied to the body with the concave services 180 being rolled and pivoted in relation to the anatomical body part. Prow section 174 defines a minimum width "$w_2$" of about 0.5 inches to about 1.5 inches. Absorbent applicator member 140 defines a length "l" ranging from about 3 inches to about 6 inches.

Figure 11:
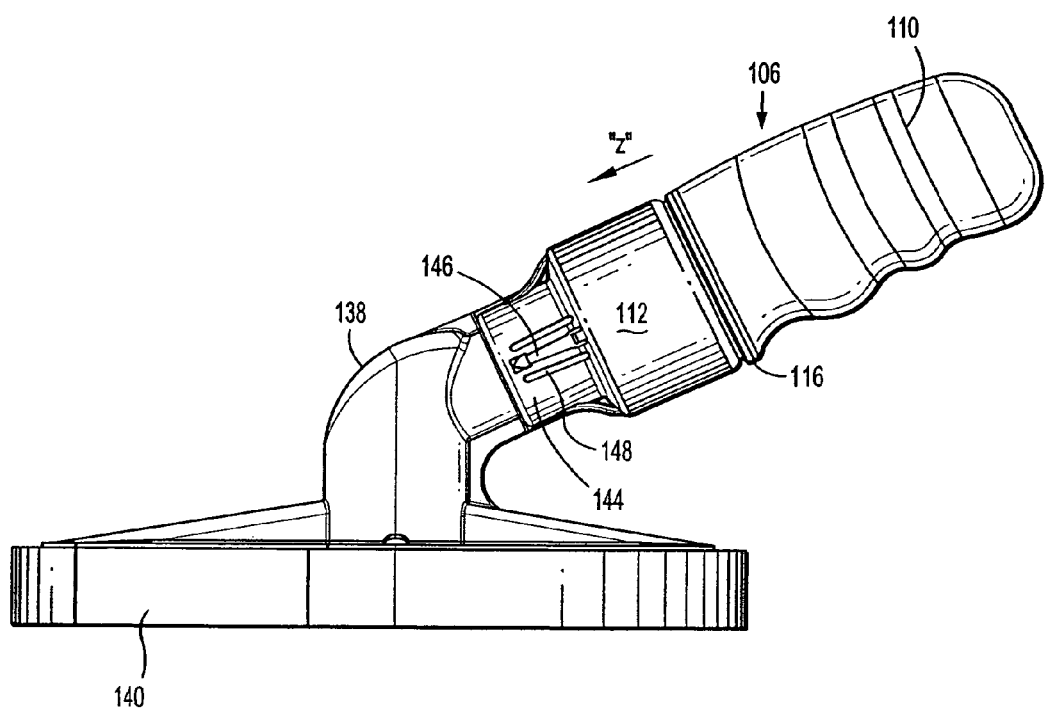
FIG. 11 is a side plan view similar to the view of FIG. 3 illustrating the fluid container assembly in a second actuated position.

The operation of apparatus 100 now be discussed. In use, the practitioner grasps applicator 100 with a single hand by anchoring his or her last three digits to an underside of fluid housing 106. The thumb is then placed across the top of applicator frame 138 to grasp the frame 138. The index finger is anchored relative to applicator frame 138, and then both thumb and index finger are simultaneously pulled toward the anchored fingers to generate a predetermined joining force between fluid container assembly 102 and applicator housing assembly 104. Fluid housing assembly 102 is thus caused to move relative to applicator head assembly 104 in a longitudinal direction, as depicted by the directional arrow "z" in FIG. 11 to its second actuated position. The range of longitudinal movement may be limited by engagement of circumferential stop or rib 116 with housing supported collar 142.

Figure 12:
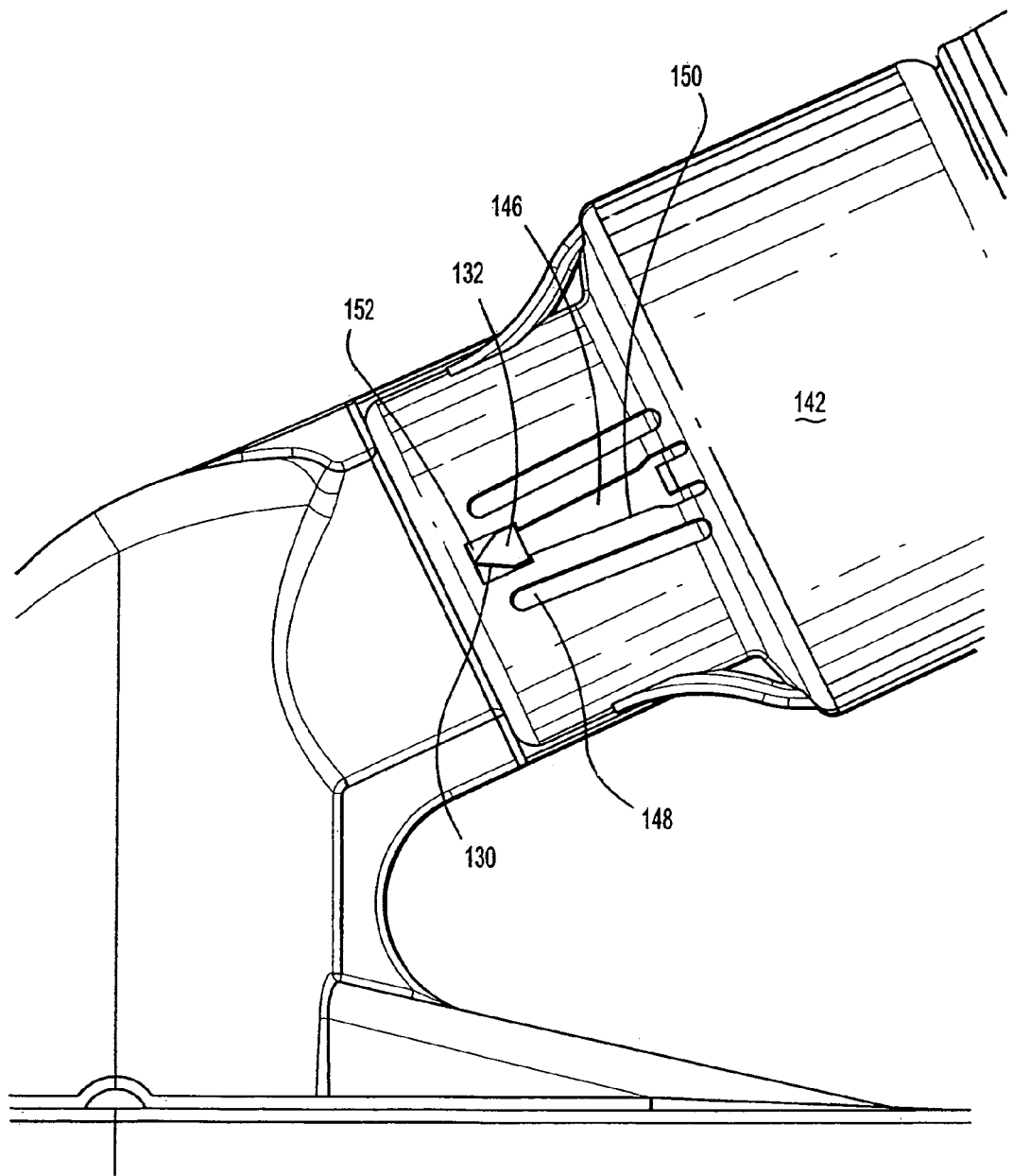
FIG. 12 is a view similar to the view of FIG. 6 illustrating the locking tabs of the end cap secured within the locking recesses of the applicator head assembly when the fluid container assembly is in the second actuated position.
Figure 13:
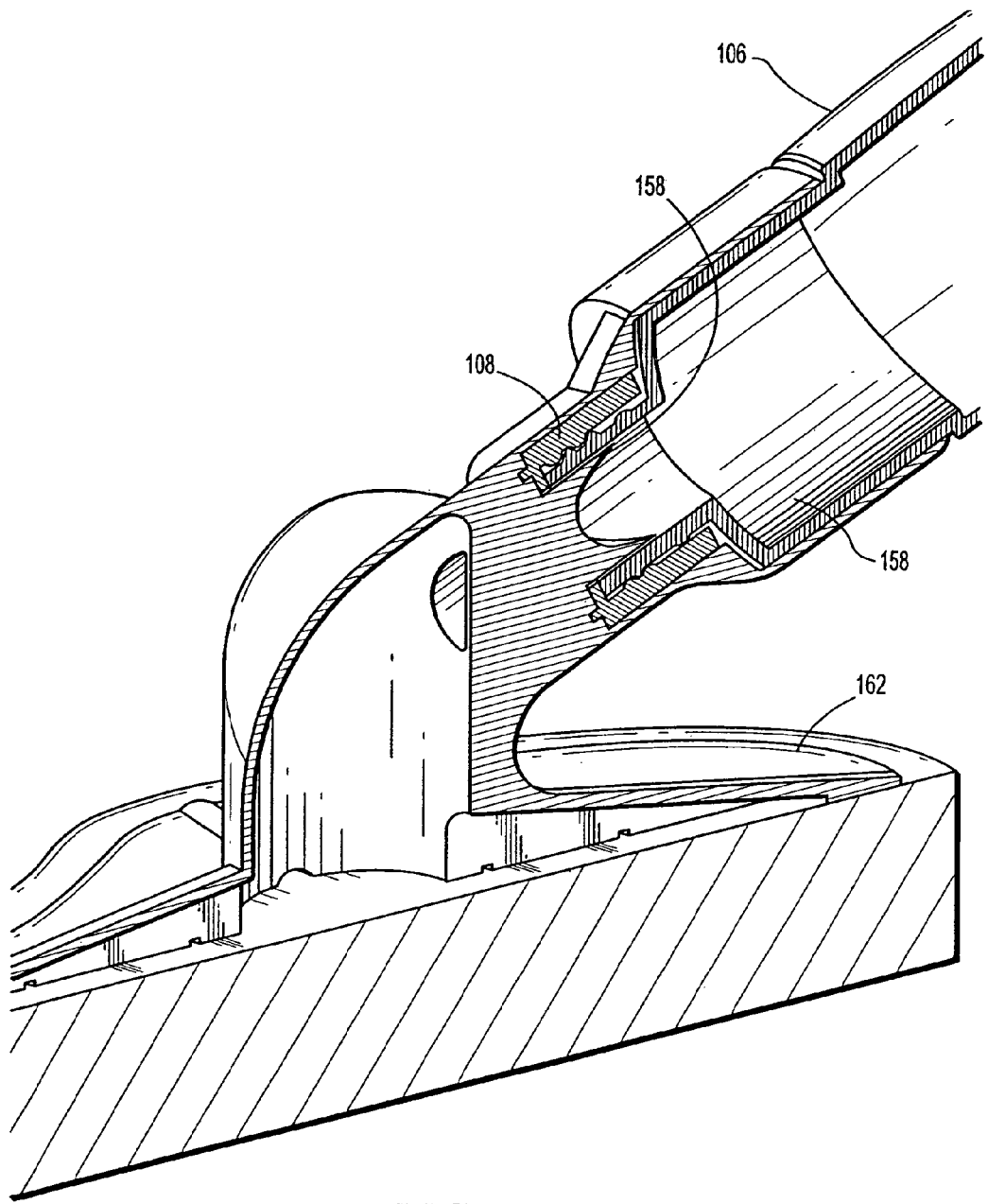
FIG. 13 is a view similar to the view of FIG. 8 illustrating the penetrating members piercing the end cap when the fluid container assembly is in the second actuated position.

Referring now to FIG. 12, during axial movement of fluid housing 106, locking tabs 132 of end cap 108 traverse axial channels 146 of applicator frame 138. As noted, longitudinal relief slots 148 adjacent axial channels 146 permits cam surfaces 150 (which define axial channels 146) to deflect outwardly through the camming engagement with angled side surfaces 130 of locking tabs 128 whereby the locking tabs 128 are received within locking recesses 152. As appreciated, cam surfaces 150 provide a degree of resistance to movement of locking tabs 128 through axial channels 146. This resistance provides a tactile indicator to the practitioner of the condition of apparatus 100 thereby minimizing the potential of inadvertent actuation of the apparatus 100. With locking tabs 128 received within locking recesses 152, the fluid container assembly 102 is retained in a second actuated position shown in FIGS. 11-13. Simultaneously with the relative advancement fluid housing assembly 102, piercing members 158 of applicator head assembly 104 penetrate liner 120 as depicted in FIG. 13. It is also noted that in the second actuated position, peripheral rib 134 is received within recess 156 (see FIG. 7) to form a substantial fluid tight seal of this location thereby minimizing fluid back toward fluid housing 106.

Figure 14:
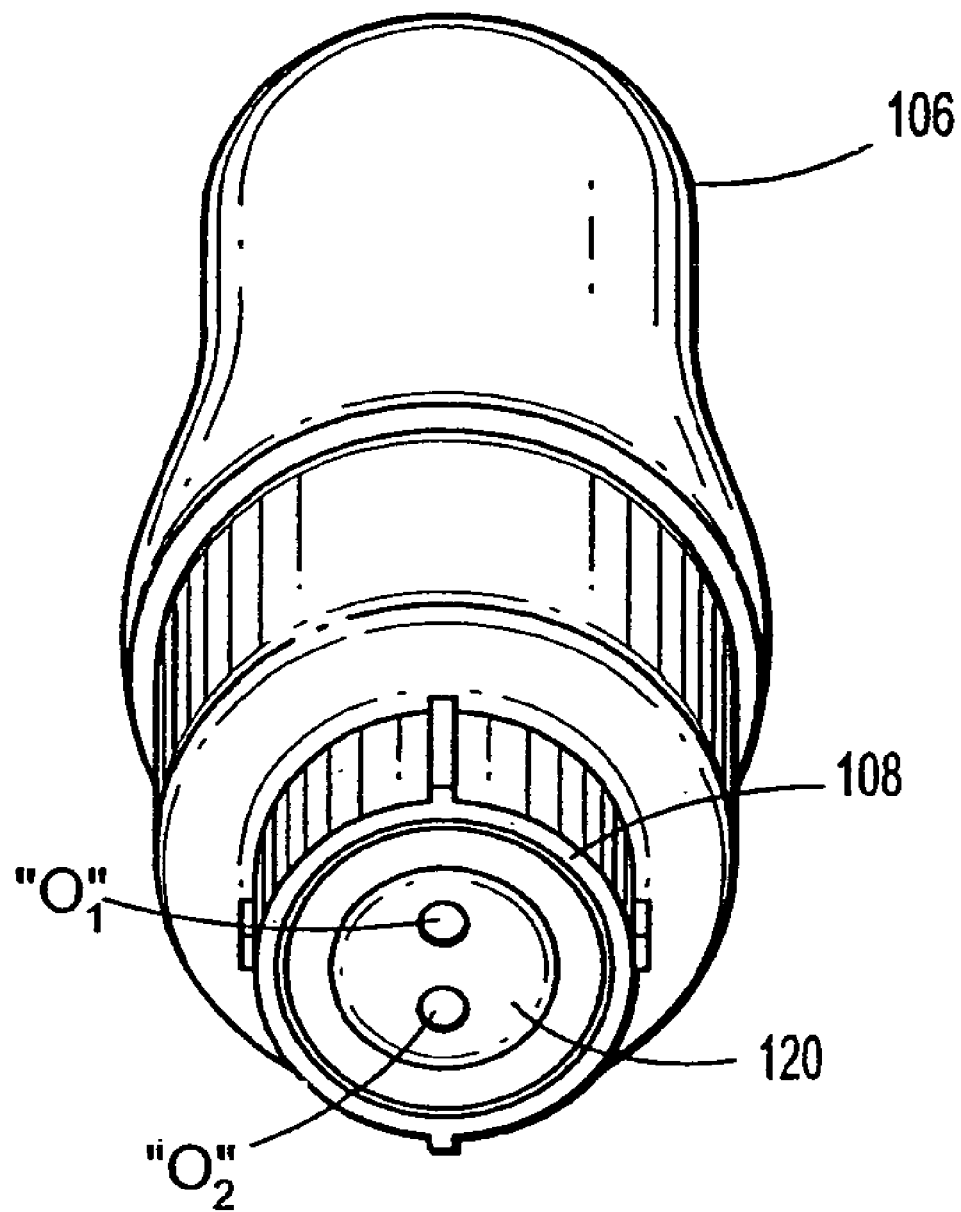
FIG. 14 is a perspective view of the fluid container assembly illustrating the drainage apertures formed in the liner of the end cap when in the second actuated position.
Figure 15:
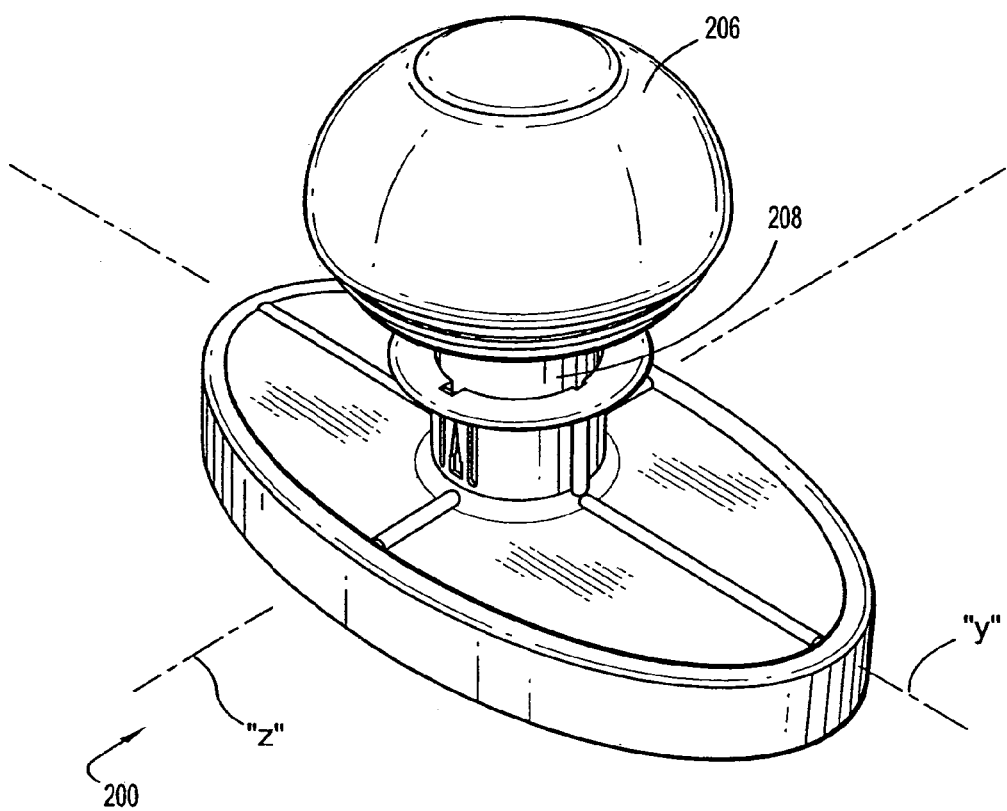
FIG. 15 is a perspective view of another embodiment of the skin applicator apparatus of the present disclosure.

Piercing members 158 may be arranged to completely cover liner 120. Alternately piercing member 158 are arranged to puncture two holes in liner 120 as depicted in FIG. 14. The two openings $O_1$, $O_2$ produced by this action produce fluid channels, one for the antiseptic solution to spill into throat of applicator frame 136 under pressure generated by moderate compression of fluid housing 106 by the practitioner. Second opening $O_2$ facilitates fluid disbursement by allowing air to enter fluid housing 106, thereby equilibrating the internals thereof, preventing vapor lock of the container contents, and providing a more consistent release of fluid. The above assembly position is defined as a second or "actuated" position.

Fluid contained within the fluid housing 106 is allowed to flow into applicator frame 138 immediately after rupture of liner 120. A moderate compression of fluid housing 106 allows for a portion of the contents therein to be evacuated, whereupon release of compression allows for air to replace the contents within fluid housing 106. Allowing for air ingress in this manner speeds fluid flow. In this way, fluid can be metered or pumped out, and within two to three pumps the entire contents of approximately 60 ml is expelled from fluid housing 106.

With reference to FIGS. 8-9, the fluid migrates to the applicator support plate 162 and is distributed through central apparatus 164 and first and second channels 166, 168 and arcuate channels 170. A gentle compression of fluid housing 106 may force the antiseptic downward into the pores of absorbent member, e.g. The arrangement of applicator plate 162 allows for transfer of the entire container contents to absorbent member 142 in approximately two to three seconds, i.e., almost instant fluid fill and equilibration, thereby allowing uniform wetting over the sponge's non-symmetrical profile.

In use, the multi-contoured absorbent member 140 conforms to substantially all body contours or topology of a patient. For example, prow shaped nose, facilitates prepping of eyes, ears, fingers, toes, groin, or other confined topology.

Additionally, the contoured or section conforms to the radial surface of an arm or leg of a subject. The extended footprint length L (i.e., longer sponge interface) of applicator 70 allows for about four times the coverage in a single stroke by using a side to side motion, as compared with the prior art. This translates into about a four hundred percent increase in productivity over prior art applicators having flatter contours, which saves prepping time and effort, particularly during turnover involving multiple surgeries.

As described above, applicator apparatus 100 of the present disclosure includes key features and advantages not found in the prior art. The single-handed triggering mechanism and single-handed activation improves ease and productivity—there is no snap ring to deal with or pre-triggering mechanism necessary, and there are no other parts that require removal prior to use. Instead, a smooth activation, single snap triggering mechanism is employed. The minimum number of parts reduces complexity and manufacturing cost. In addition, fluid housing 106 permits for faster wetting, and the integrated fluid manifold within the applicator frame 138 allows for uniform wetting and balanced fill of any sponge configuration regardless of fluid viscosity. The larger sponge consequently allows for inverted use of applicator, faster prep and controlled fluid release. The contoured multi-use sponge may conform to any patient topology, and the integrated sponge stick/prow provides the dexterity of a conventional sponge stick with the speed of an applicator.

Referring now to FIGS. 15-18, another preferred embodiment of the present disclosure is illustrated. Skin applicator apparatus 200 includes fluid container assembly 202 and applicator head assembly 204 mounted to the fluid housing assembly 202. Fluid container assembly 202 includes fluid housing 206 and collar 208 contiguously extending from the fluid housing 206. Fluid housing 206 is preferably in the shape of a dome and may incorporate an accordion like configuration to permit the housing 206 to be compressed to expel the fluid contained therein. It is envisioned that fluid housing 206 may have various configurations, such as, for example, cylindrical, rectangular, elliptical, polygon oh, etc., according to requirements of a particular application. Fluid housing 206 may be formed of an elastomeric material or any of the materials defined hereinabove. Fluid container assembly 202 further includes liner 210 and end cap 212 which is mounted to collar 208 of fluid housing 206. Liner 210 is preferably in the form of a foil seal and may be adhered to collar 208 and/or within the interior of end cap 212.

Figure 19:
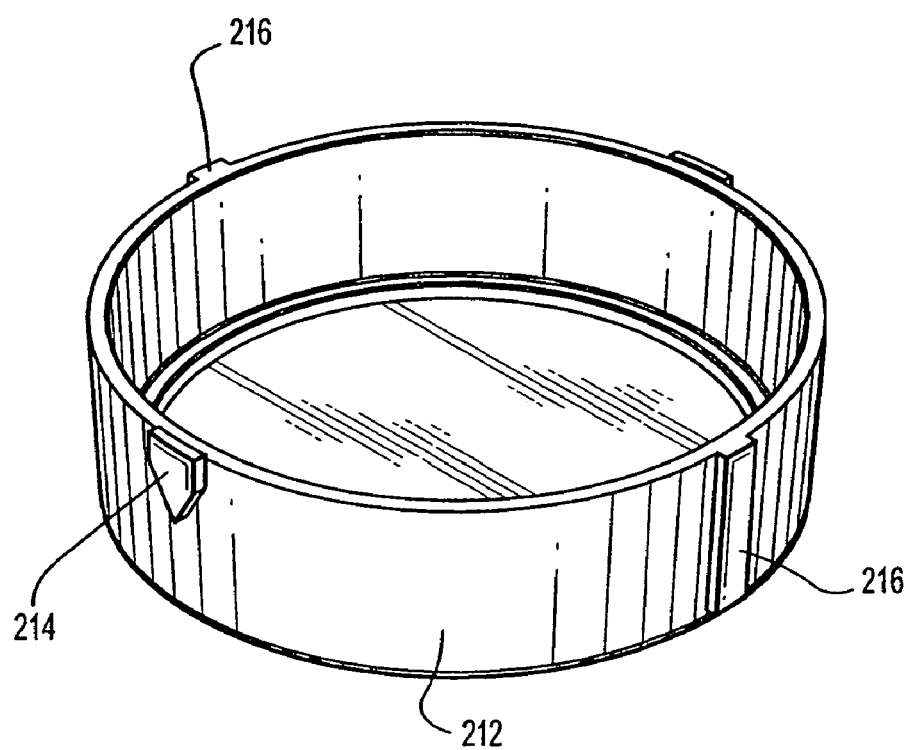
FIG. 19 is a perspective view of the end cap.

As best depicted in FIG. 19, end cap 212 is devoid of threads and may be secured to collar 208 with adhesives, welding, cements, or the like. End cap 212 includes a pair of diametrically opposed locking tabs 214 on its outer surface, preferably, about 180° apart, and axial ribs 216. Locking tabs and axial ribs 216 function in a similar manner to the locking tabs and axial ribs of the embodiment of FIGS. 1-14.

Figure 16:
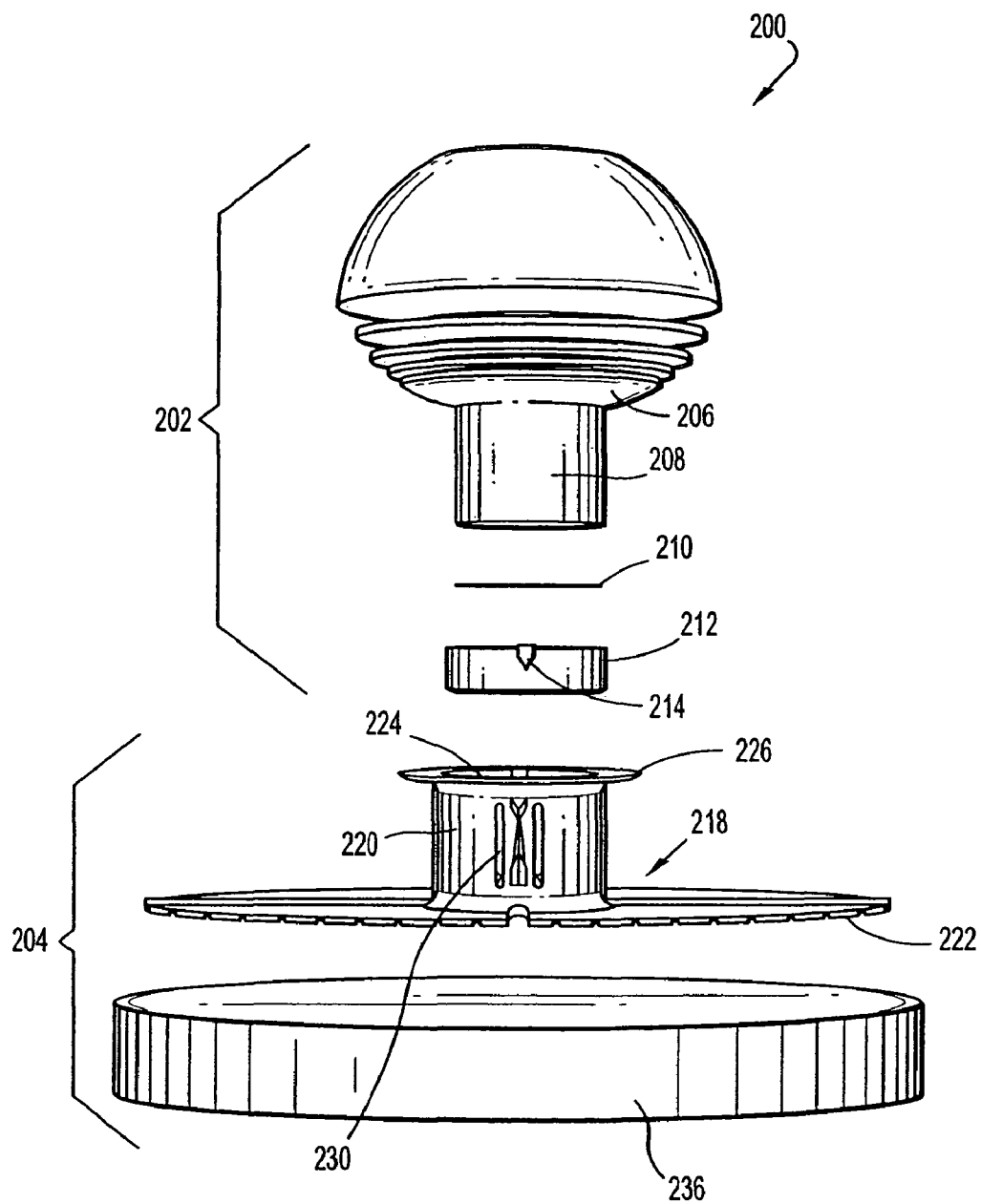
FIG. 16 is an exploded perspective view of the skin applicator apparatus of FIG. 15.
Figure 17:
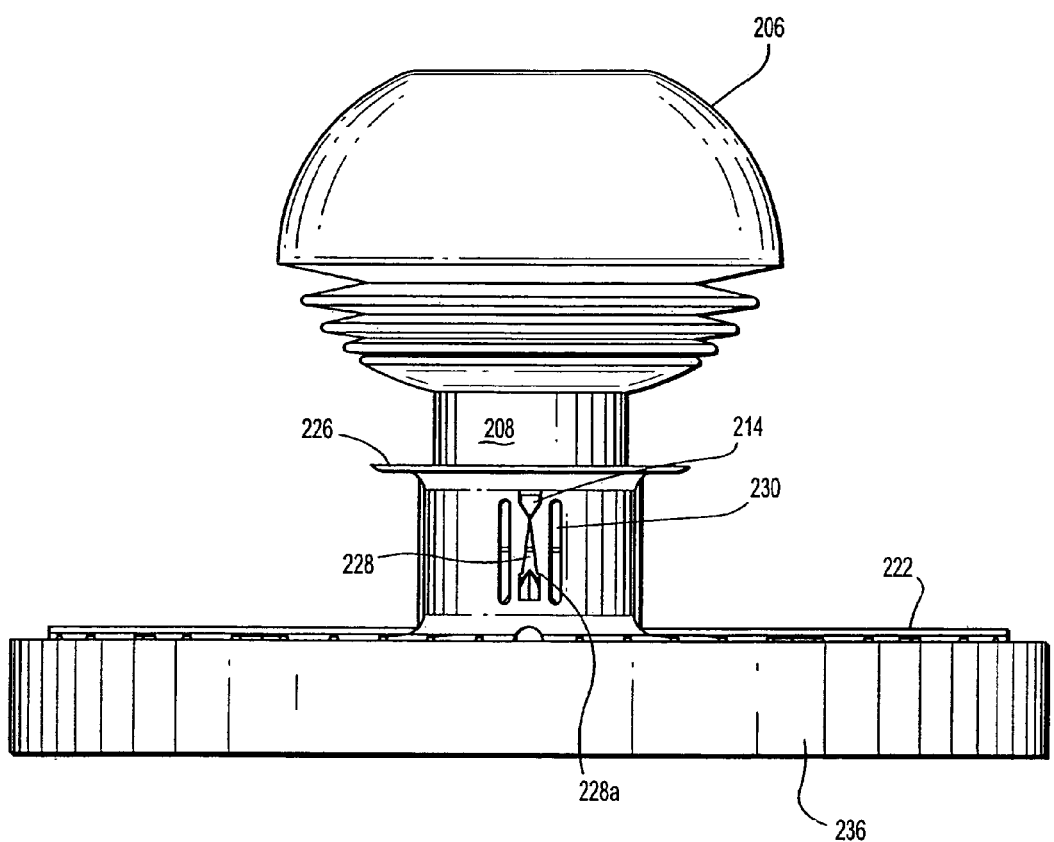
FIG. 17 is a side plan view of the skin applicator apparatus of FIG. 15 illustrating the fluid housing assembly in a first transit position thereof.
Figure 18:
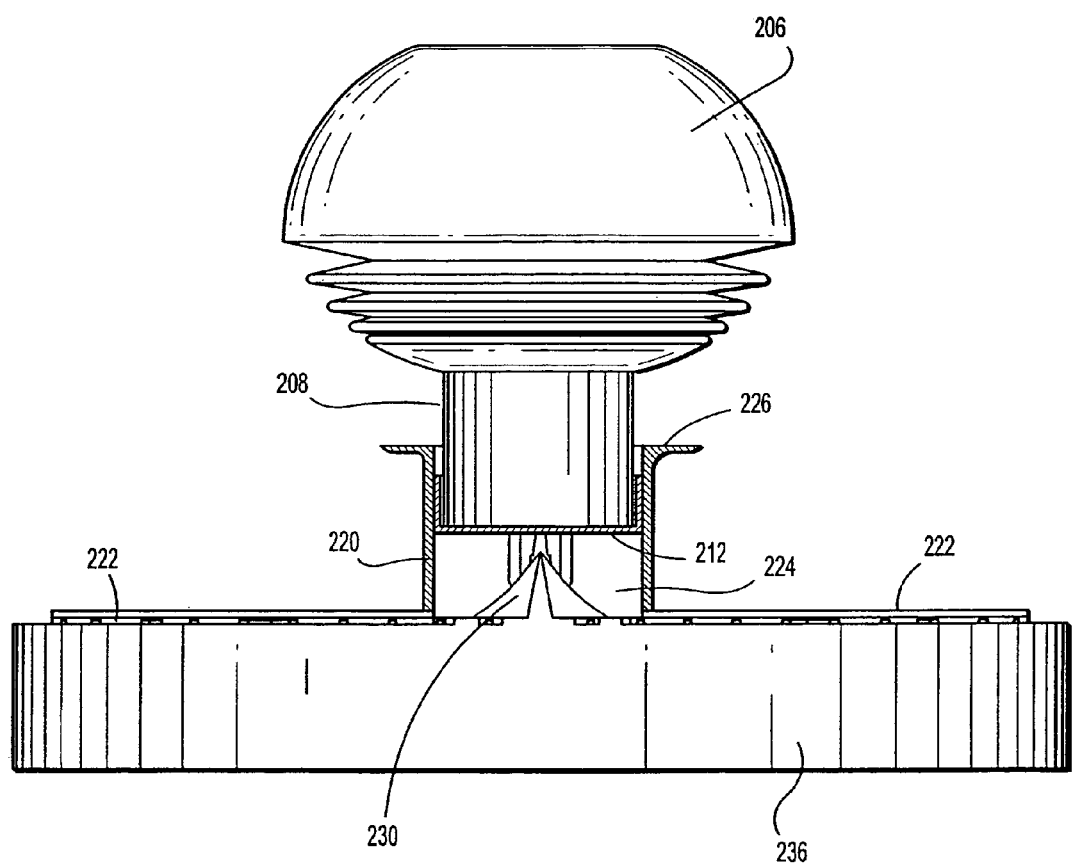
FIG. 18 is a side cross-sectional view of the skin applicator apparatus in the first transit position.

With reference to FIGS. 16-18, applicator head assembly 204 includes applicator frame 218 having throat 220 and applicator support plate 222 connected to the throat 220. Throat 220 defines internal opening 224 which permits passage of the medical agent to support plate 222 and has proximal flange 226 which is advantageously dimension to be grasped by the fingers of the practitioner. A pair of axial channels 228 with corresponding longitudinal relief slots 230 extends within the walls of throat 220. Axial channels 228 receive locking tabs 214 and permit the locking tabs 214 to traverse the channels 228 during actuation of the instrument. Throat 220 has penetrating spike or member 230 extending upwardly from applicator supporting plate 222 with internal opening 224. Spike 230 is shown as a single conically shaped element, however spike 230 can assume any sharpened configuration or may be multiple in number.

Figure 20:
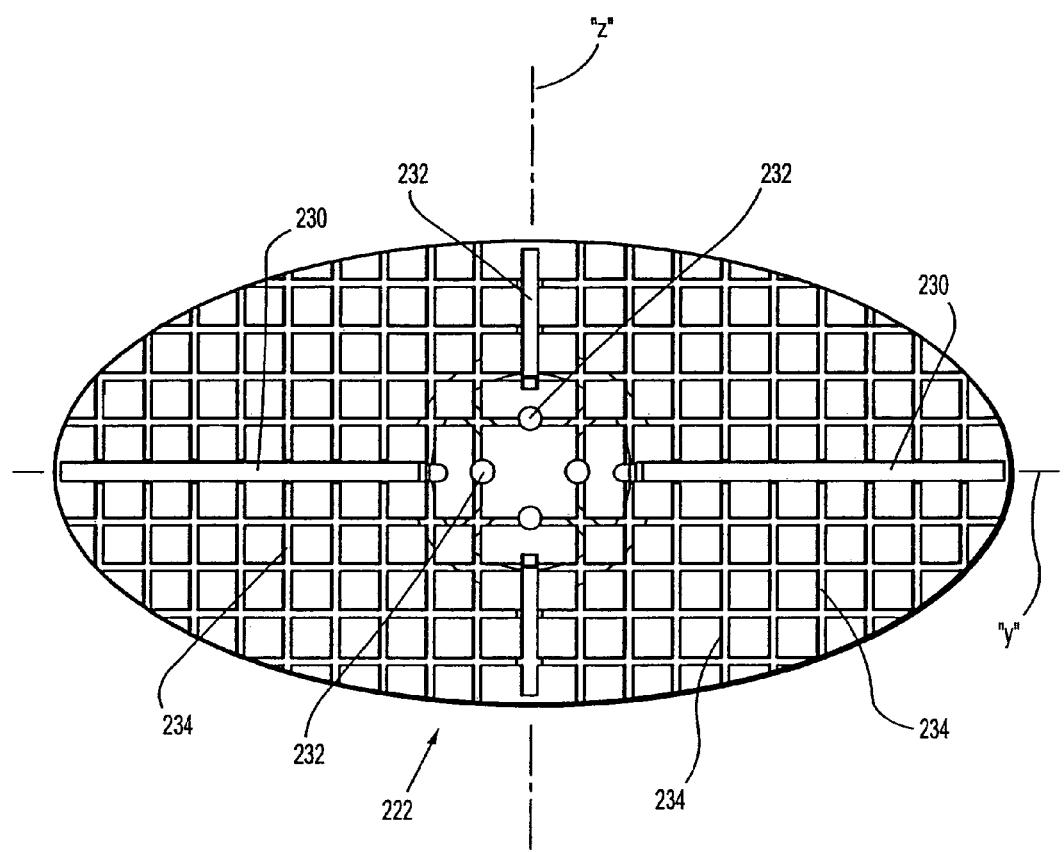
FIG. 20 is a bottom plan view of the applicator frame of the applicator head assembly.
Figure 21:
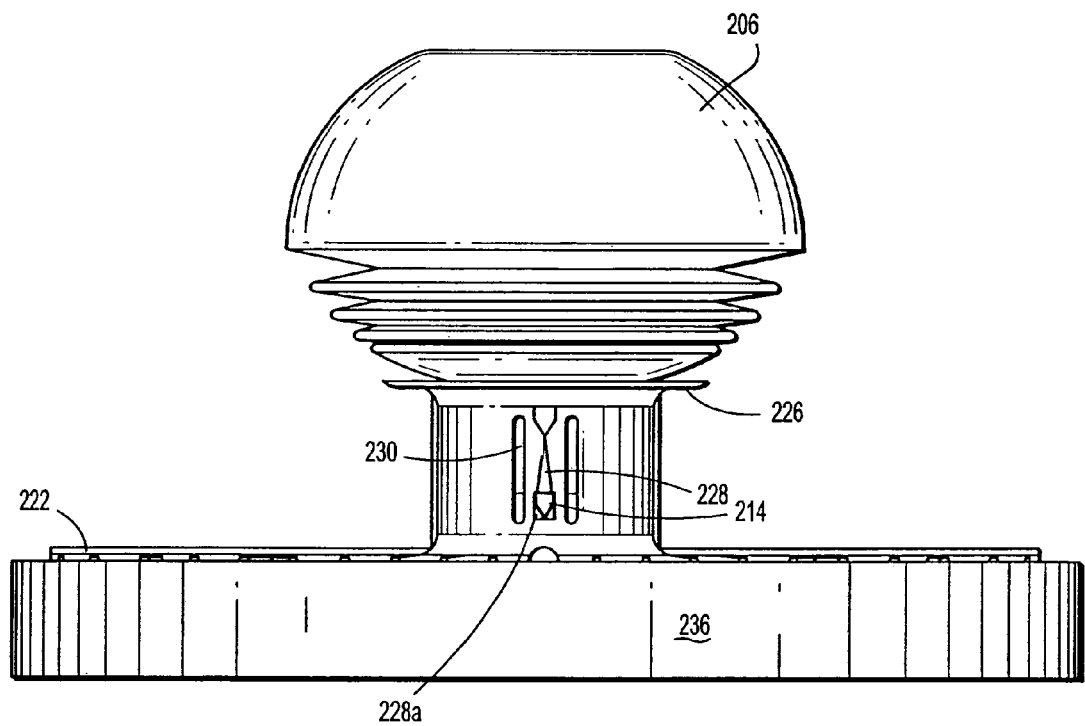
FIG. 21 is a side plan view similar to the view of FIG. 17 illustrating the fluid housing assembly in a second actuated position thereof.

Referring to FIGS. 18 and 20, applicator support plate 222 includes a plurality of apertures 232 in communication with internal opening 224 of throat 220, and centrally disposed within the center of applicator plate 222. On its lower surface, applicator support plate 222 includes first and second linear channels 230, 232 in general transverse relation to each other and centrally located along the major and minor axes "y", "z" of the support plate 222. Applicator support plate 222 further includes a grid-type arrangement having a plurality of narrow intersecting channels 234 on its lowest surface and intersecting linear channels 230, 232.

In use, fluid container assembly 202 is moved from the first transit position of FIG. 17 to the second actuated position of FIG. 20. Preferably, the practitioner grabs flange 226 of applicator frame 218 with the index and middle finger and positions the palm of his hand against the upper surface of fluid housing 206. During this movement, locking tabs 214 traverse axial channels 228 and are secured within the locking recesses 228a of the axial channels 228 in a manner similar to that described hereinabove. Concurrently therewith, penetrating member 230 pierces liner 210 to permit expulsion of the fluid contained within fluid housing 206. The fluid then communicates through internal opening 224 of throat 220 and apertures 232. The fluid agent then communicates through linear channels 230, 232, and further through the grid type arrangement 234 provided on the lower surface of applicator frame 218. With this arrangement substantially the entire absorbent member 236 is saturated with the medical agent. Apparatus 200 is then utilized to apply the medical agent to the skin of the patient. Fluid housing 206 may be compressed to facilitate expulsion of the fluid agent or the agent may be gravity fed by inverting the fluid housing 206.

Figure 22:
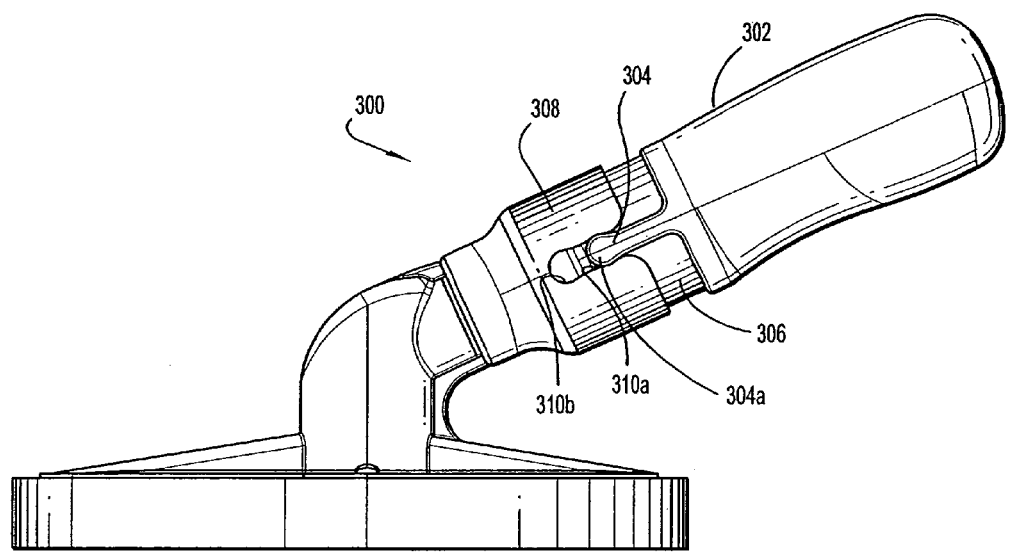
FIG. 22 is a side plan view of another alternate embodiment of the skin applicator apparatus of the present disclosure.
Figure 23:
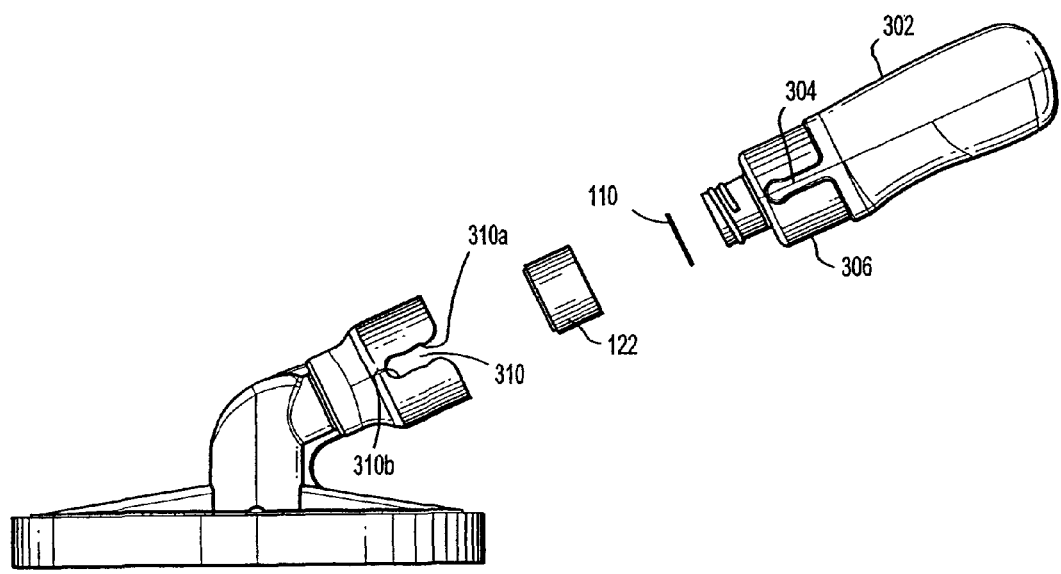
FIG. 23 is an exploded view of the skin applicator apparatus of FIG. 22.
Figure 24:
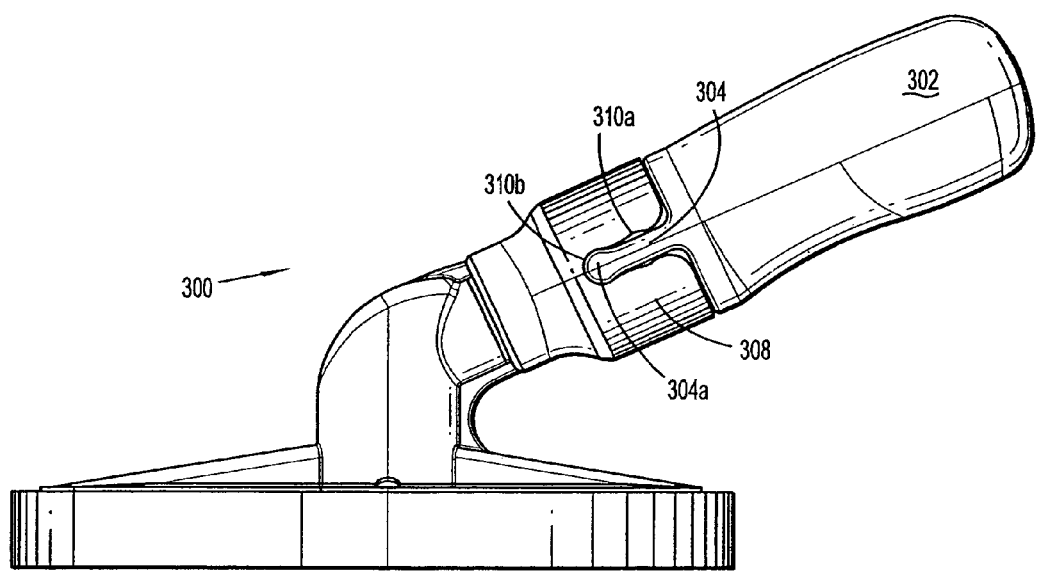
FIG. 24 is a side plan view of the skin applicator apparatus in a second actuated position.
Figure 25:
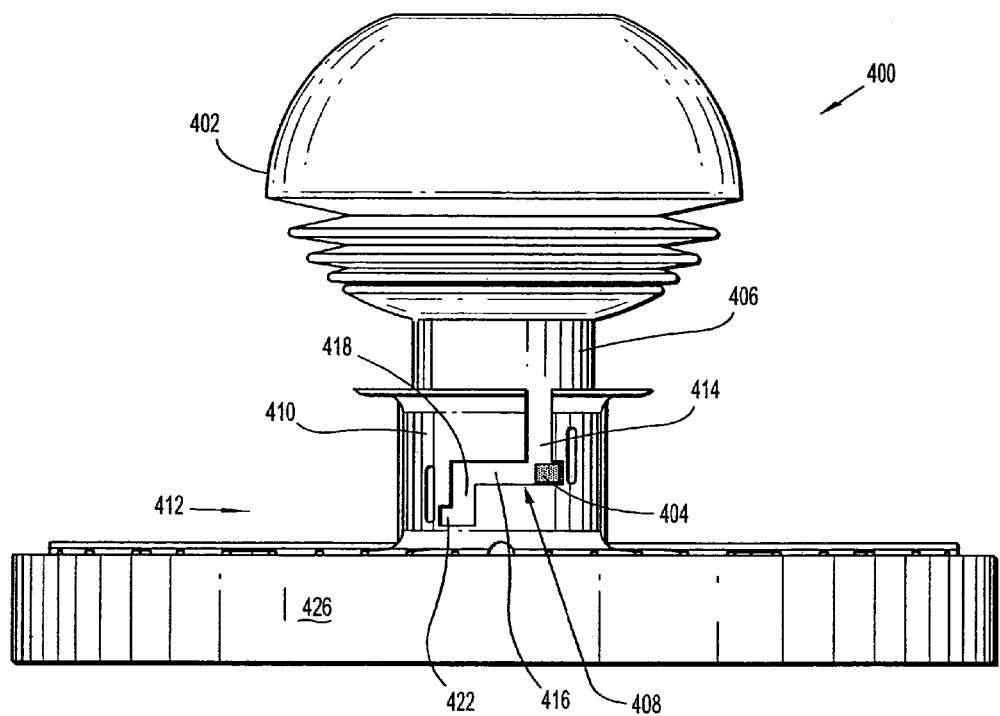
FIG. 25 is a side plan view of another alternate embodiment of the skin applicator apparatus of the present disclosure illustrating the fluid housing in the first transit position.
Figure 26:
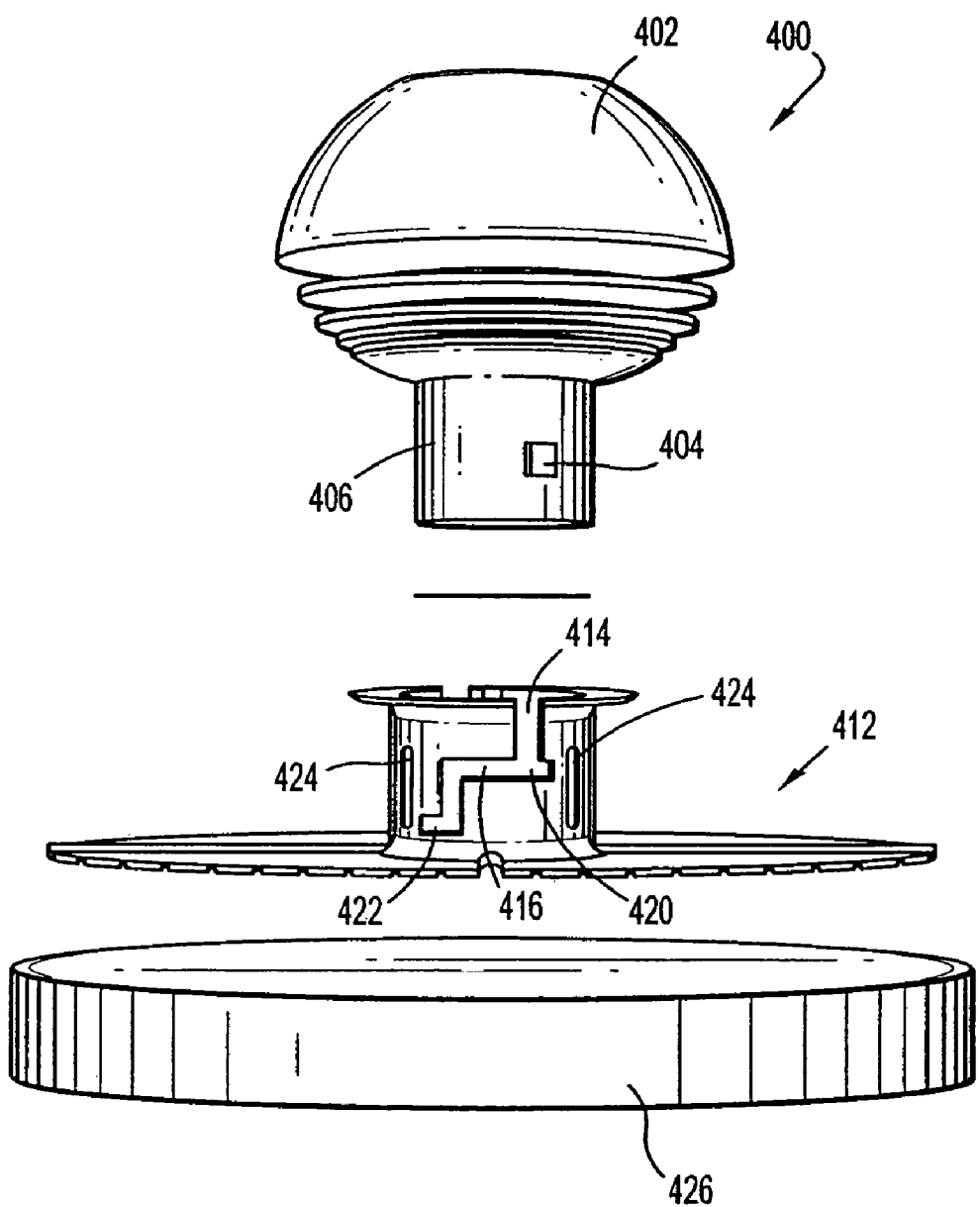
FIG. 26 is an exploded perspective view of the skin applicator apparatus of FIG. 25.

Referring now to FIGS. 22-24, an alternate embodiment of the present disclosure is illustrated. This embodiment is substantially similar to the embodiment of FIG. 1. However, in accordance with this embodiment, skin applicator apparatus 300 includes fluid housing 302 having a pair of diametrically opposed locking ribs 304 disposed on the exterior surface of cylindrical section 306. Locking ribs 304 are generally linear in configuration and possess enlarged arcuate rib sections 304a at its distal end. Applicator frame 306 incorporates collar 308 having locking channels 310 generally corresponding in shape and position to locking ribs 304 of fluid housing 302. Specifically, locking channels 310 are substantially linear and include first and second arcuate channel sections 310a, 310b. In the first transit position of fluid housing 302 shown in FIG. 22, each enlarged arcuate rib section 304a of locking ribs 304 resides within first arcuate channel section 310a of locking channel 310 and is confined therein through the inner boundary of the channel section 310a thus releasably securing fluid housing 302 in the first transit position. When it is decided to actuate the apparatus 300, the practitioner advances fluid housing 302 relative to applicator frame 306. During this movement, locking ribs 304 traverse locking channels 310 whereby the surfaces defining the locking channels 310 deflect outwardly to permit passage of the enlarged rib section 304a and reception thereof within second arcuate channel section 310b in snap relation therewith. In this position, locking ribs 304 are secured within locking channels 310 thereby securing the fluid housing 302 in the second actuated position of FIG. 24. In all other respects, apparatus 300 is similar in function to apparatus 100 of FIG. 1.

Figure 27:
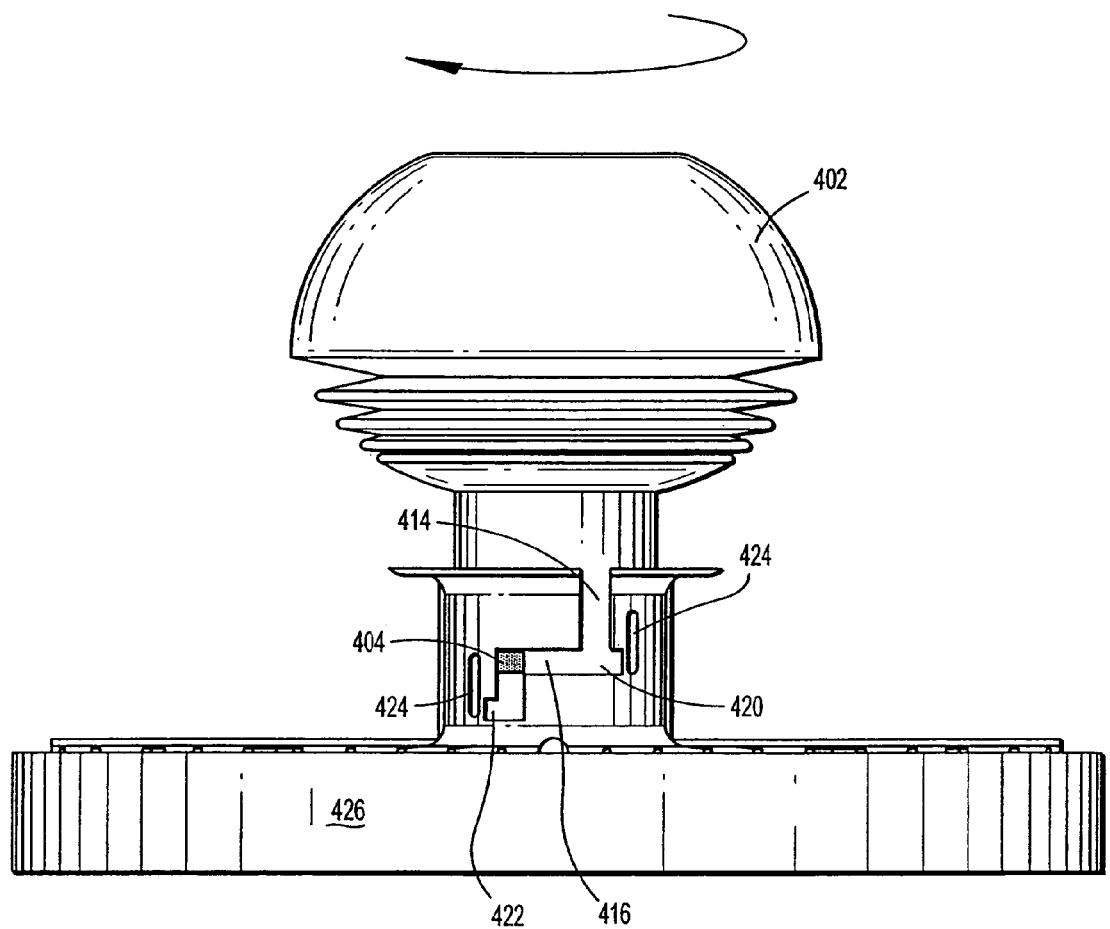
FIG. 27 is a side plan view illustrating rotation of the fluid housing to release the fluid housing from the first transit position.
Figure 28:
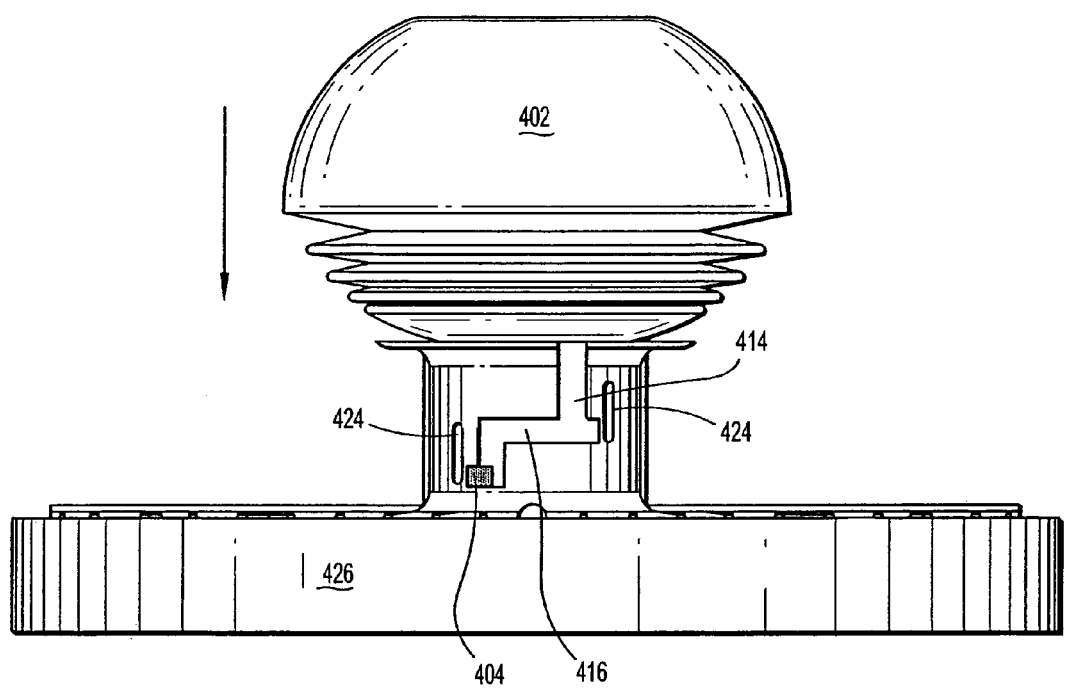
FIG. 28 is a side plan view of the skin applicator apparatus illustrating the fluid housing in a second actuated position.

FIGS. 25-28 illustrate another preferred embodiment of the present disclosure. Skin applicator apparatus 400 is generally similar to apparatus 200 described in connection with the embodiment of FIGS. 15. However, in accordance with this embodiment, fluid housing 402 includes at least one or a pair of diametrically opposed locking tabs 404 on distal collar 406. In this embodiment, apparatus 200 is devoid of an end cap; however, it is envisioned that apparatus 200 may have an end cap with the aforedescribed locking tabs 404. Locking tabs 404 are received within corresponding generally z-shaped slots 408 defined in throat 410 of applicator frame 412. Z-shaped slot 408 is characterized by having a first vertical section 414, a horizontal section 416 and a second vertical section 418 extending from the horizontal section 416. Vertical section 414, 418 includes locking recesses 420, 422. A longitudinal relief slot 424 is disposed adjacent each vertical section 414, 418 of z-shaped slots 408. Relief slots 424 permit outward deflection of the wall surfaces defining vertical sections 414, 418 to permit locking tabs 404 to be received within locking recesses 420, 422. In use, collar 406 of fluid housing 402 is positioned within throat 410 of applicator frame 412 with locking tabs 404 positioned within vertical section 414 of z-shaped slots 408 and received within locking recess 420. In this position, fluid housing 402 is retained within applicator frame 412 and releasably secured in the first transit position through cooperation of tabs 404 with the wall surfaces defining locking recesses 420. When it is decided to actuate apparatus 400, the practitioner rotates fluid housing 402 in the direction of directional arrow "a" relative to applicator frame 412 as shown in FIG. 27. Locking tabs 404 are forced from locking recesses 420 whereby relief slots 424 permit the surfaces defining locking recesses 420 to deflect in an outward direction. The force required to displace locking tabs 404 from locking recesses 420 provides a tactile indicator to the practitioner of the movement of fluid housing 402 toward the second actuated position. Locking tabs 404 traverse horizontal sections 416 of the z-shaped slot 408 to a position in alignment with second vertical section 418, shown in FIG. 27. Thereafter, the practitioner applies a distal force to fluid housing 402 to cause the fluid housing 402 to advance relative to applicator frame 412 to the position depicted in FIG. 28. During this movement, locking tabs 404 traverse second vertical section 418 of the shaped slot 408 and are received within the locking recesses 422. As appreciated, during this movement wall surfaces defining vertical section 418 are permitted to deflect outwardly by provision of longitudinal relief slots 424 to permit locking tabs 404 to be received within locking recesses 422. Locking recesses 422 thus retain locking tabs 404 to thereby retain fluid housing 402 in its second actuated position dispensing the medical agent into absorbent member 426.

Figure 29:
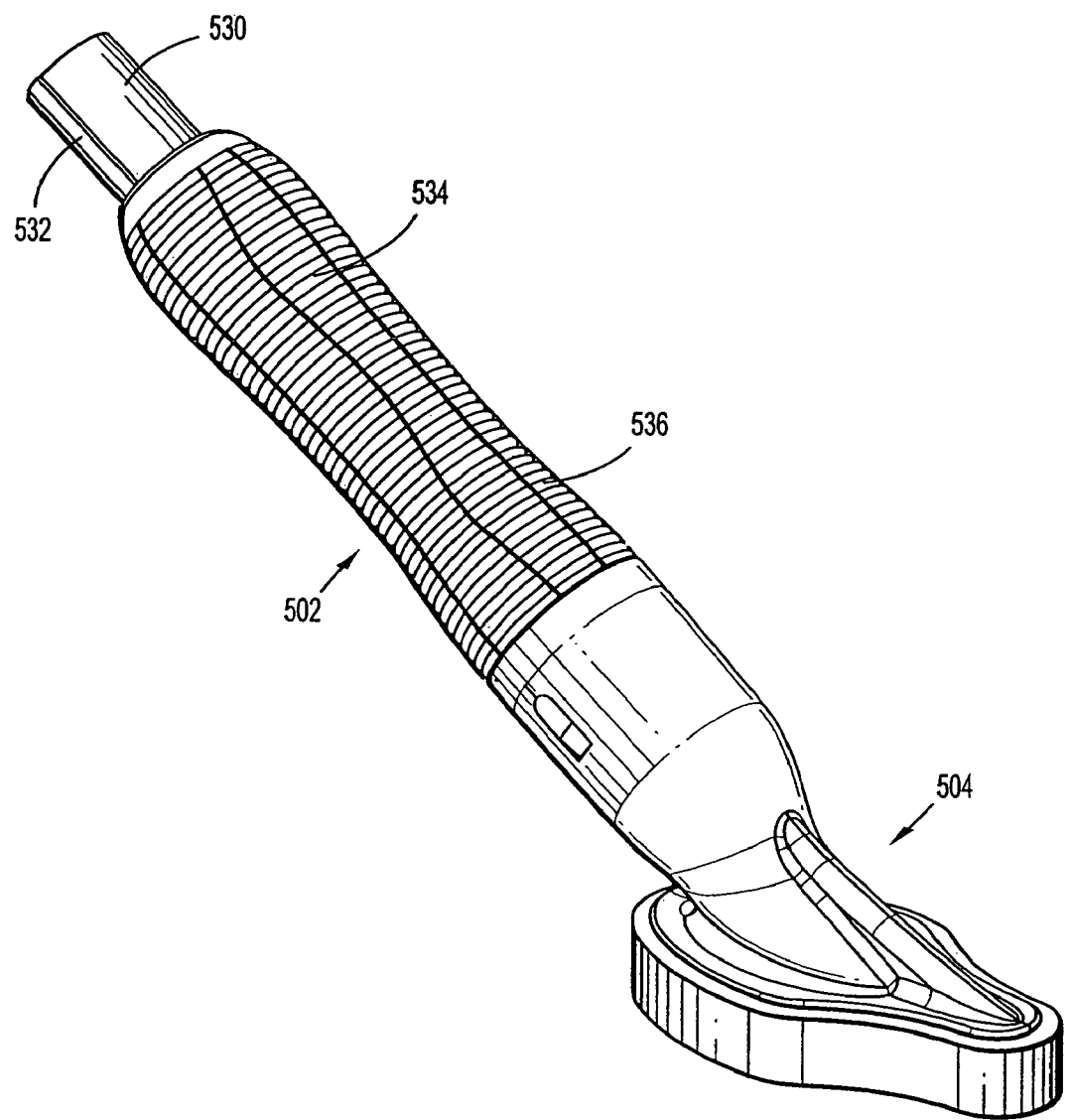
FIG. 29 is a perspective view of another alternate embodiment of the skin applicator apparatus of the present disclosure.
Figure 30:
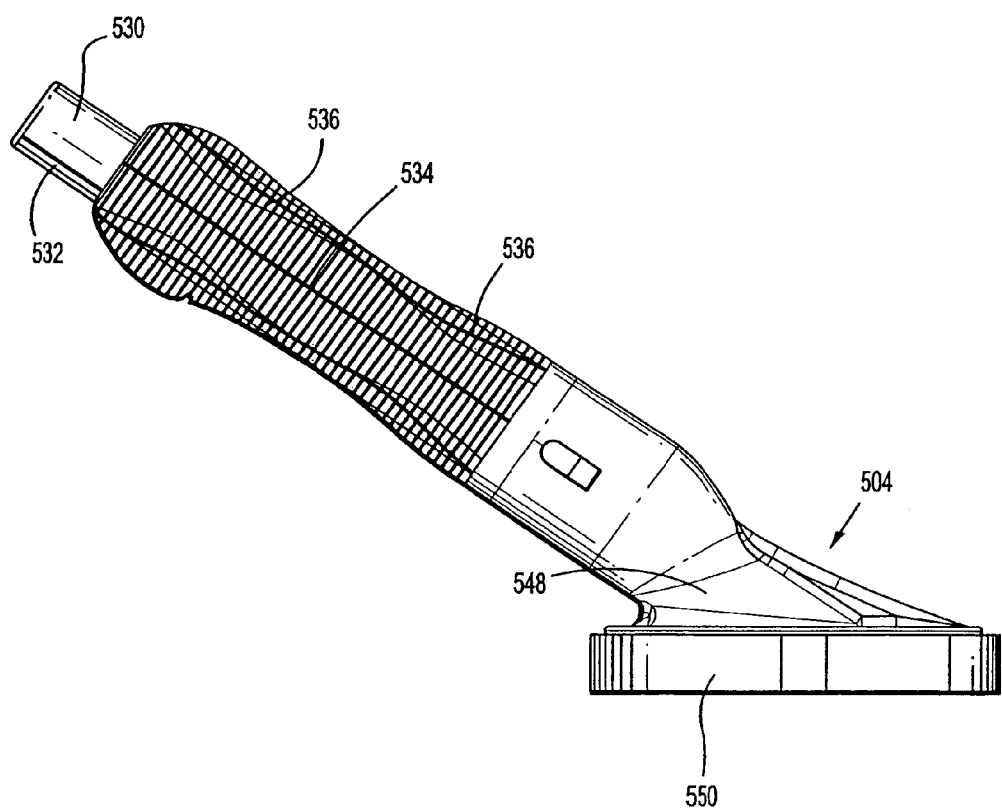
FIG. 30 is a side plan view of the skin applicator apparatus of FIG. 29 illustrating the fluid container assembly in the first transit position.
Figure 31:
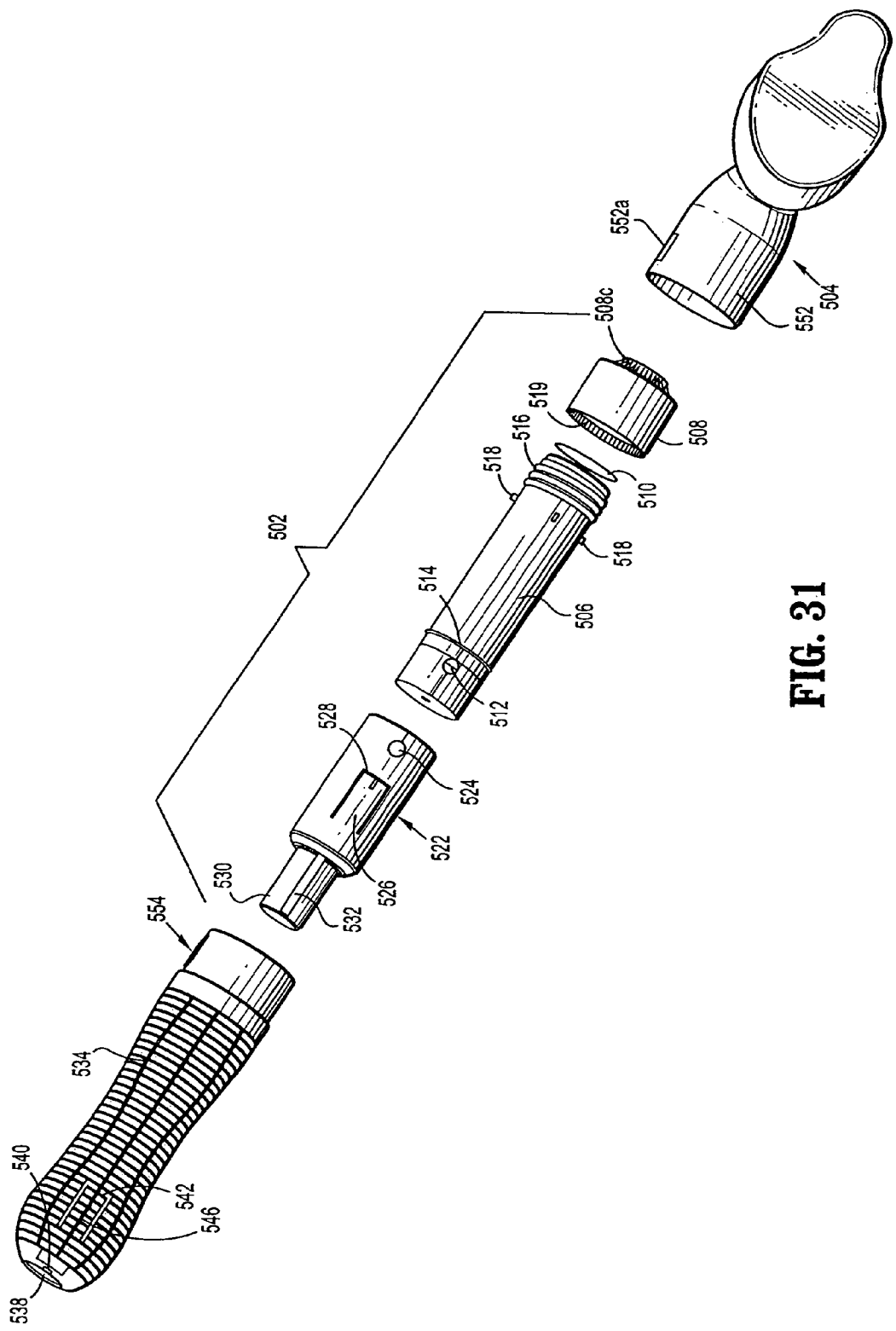
FIG. 31 is an exploded perspective view of the skin applicator apparatus of FIG. 29.
Figure 33:
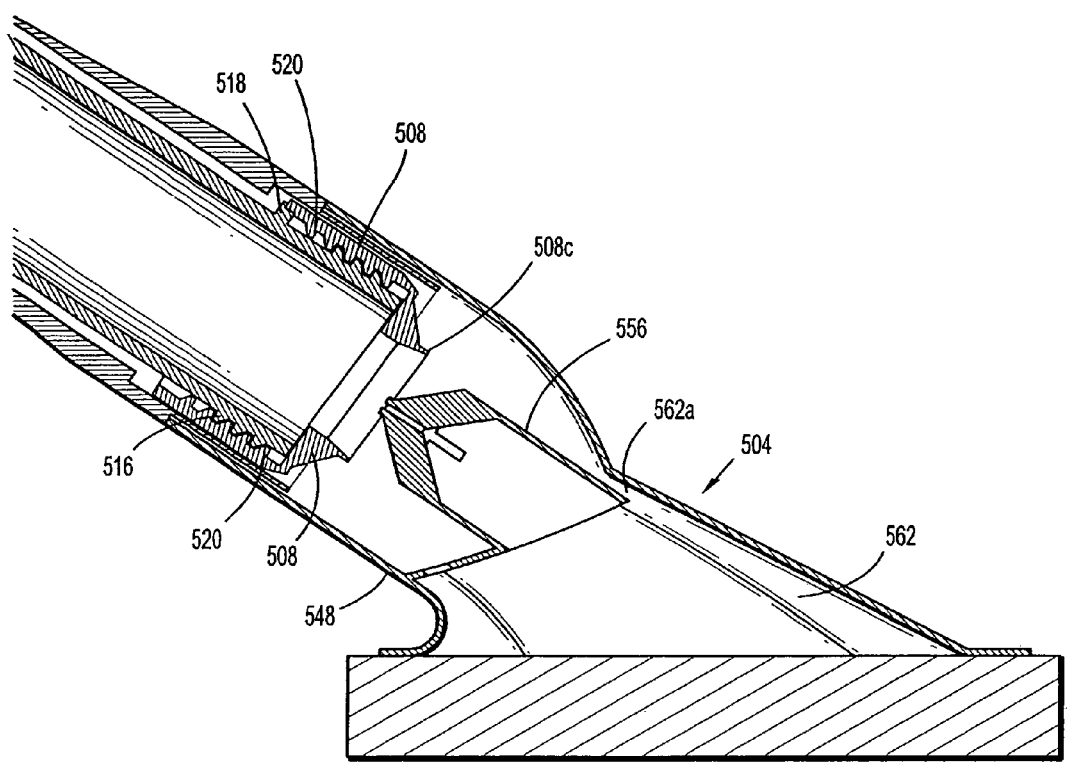
FIG. 33 is a side cross-sectional view of the distal end of the applicator apparatus.
Figure 34:
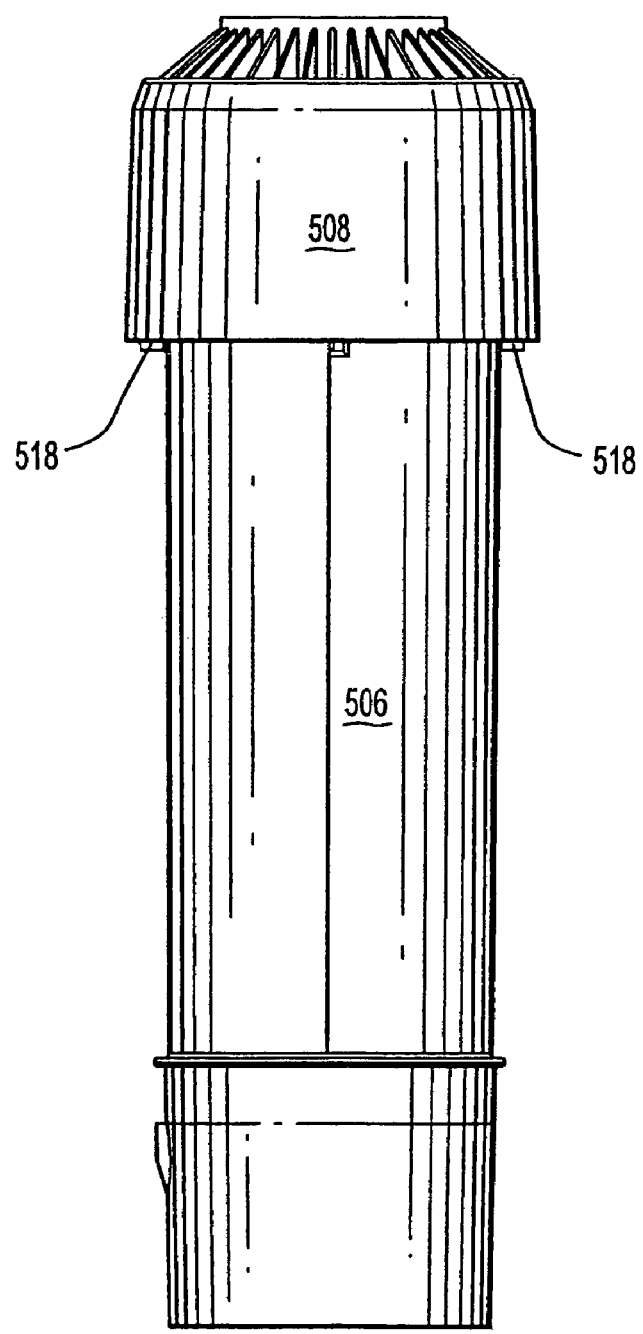
FIG. 34 is a side plan view of the fluid housing and the end cap.
Figure 35:
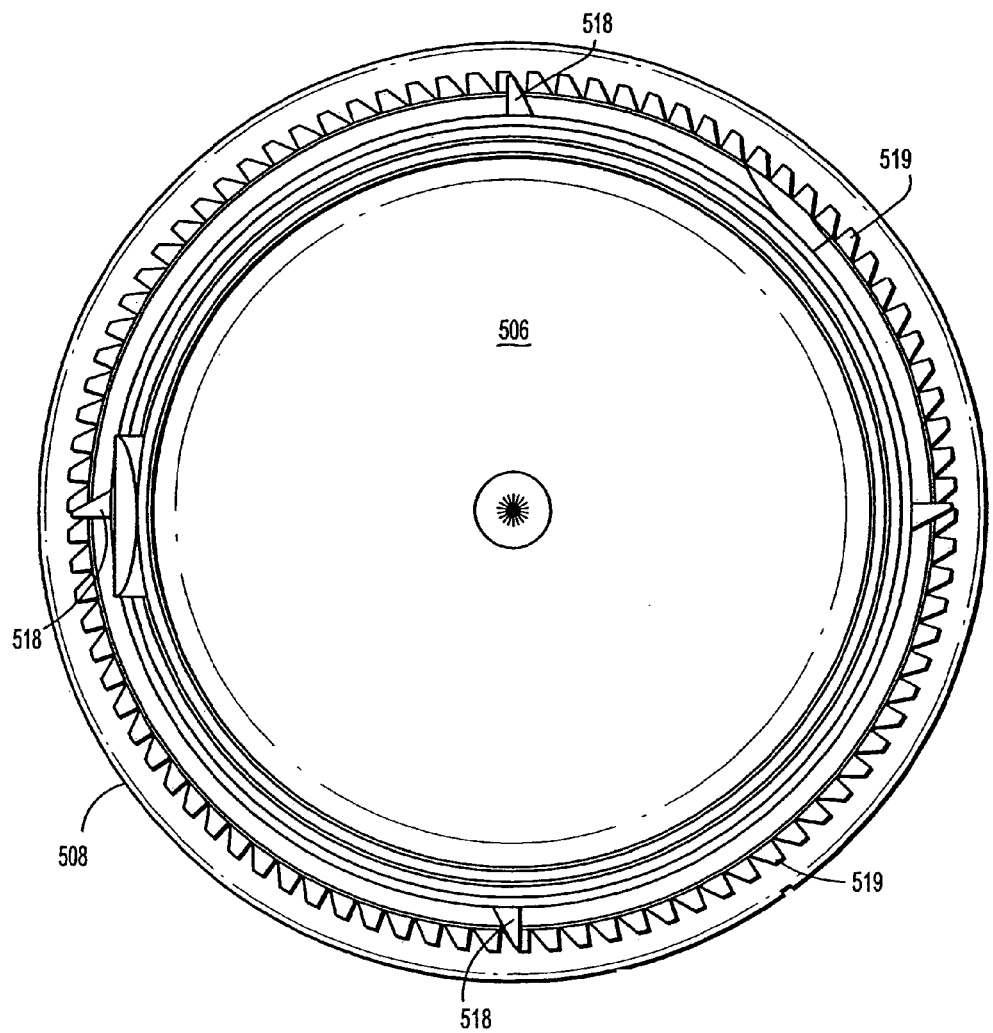
FIG. 35 is an axial view of the fluid housing and the end cap.

Referring now to FIGS. 29-31, there is illustrated another alternative embodiment of the skin applicator apparatus of the present disclosure. Skin applicator apparatus 500 includes fluid container assembly 502 and applicator head assembly 504 connected to the fluid container assembly 502. Fluid container assembly 502 includes fluid housing 506, end cap 508 connected to the housing 506 and liner 510. Fluid housing 506 includes at least one cylindrical locking protrusion 512 or, alternatively, a pair of locking protrusions 512 which extends radially outwardly relative to housing axis "x", and circumferential rib 514 distal of the locking protrusion(s) 512. Fluid housing 506 further includes external thread 516 at its distal end and a plurality of radially spaced wings 518 extending outwardly from the wall of fluid housing 506 proximal of thread 516. Liner 510 is preferably a foil liner, and may be secured to fluid housing 506 through any of the aforementioned means. End cap 508 includes internal thread 520 which cooperates with external thread 516 of fluid housing 506 to secure the end cap 508 onto the fluid housing 506 (FIG. 33). End cap 508 further includes a plurality of angled teeth 519 at the mouth of the end cap (FIG. 31 and FIG. 35). In the secured position, radially spaced wings 518 on the exterior surface of fluid housing 506 engage or bite into the angled teeth 519 of end cap 508 to prevent the end cap 508 from inadvertent removal from the fluid housing 506 (FIG. 35). End cap 508 further defines a distal collar section 508c having a reduced diameter—the function of which will be discussed in greater detail hereinbelow.

Referring again to FIGS. 30-32, fluid container assembly 502 further includes housing extension 522 which is connected to fluid housing 506. In one preferred method of attachment, housing extension 522 includes a pair of cylindrical openings 524 through its wall for reception of locking protrusions 512 of fluid housing 506 in snap relation therewith. Other means for connecting housing extension 522 to fluid housing 506 are also envisioned. Housing extension 522 further includes locking lever 526 in its outer wall. Locking lever 526 is adapted to releasably retain fluid housing 506 in the first unactuated position. Locking lever 526 defines locking shelf 528 and is adapted to deflect radially inwardly along its living hinge to release the locking shelf 528 as will be discussed. Housing extension 522 further defines manually engageable button 530 at its proximal end. Button 530 defines a reduced diameter relative to the remaining portion of housing extension 522 and has a rail 532 extending in an axial direction along its outer surface. Rail 532 ensures a single alignment position to facilitate assembly.

Skin applicator apparatus 500 further includes outer housing 534. Outer housing 534 is secured to applicator head assembly 504 and is dimensioned to accommodate fluid housing 506 and housing extension 522. Outer housing 534 defines a contoured configuration having a plurality of spaced ribs 536 on its outer surface to facilitate gripping engagement by the practitioner. Outer housing 534 defines central aperture 538 at its proximal end which receives manually engageable button 530 of housing extension 522, and keyed opening 540 for receiving rail 532 of the housing extension 522 (FIG. 31). With this relationship, housing extension 522 is adapted to move in a general longitudinal direction relative to outer housing 534, but, is rotatably fixed relative to the outer housing 534.

Figure 32:
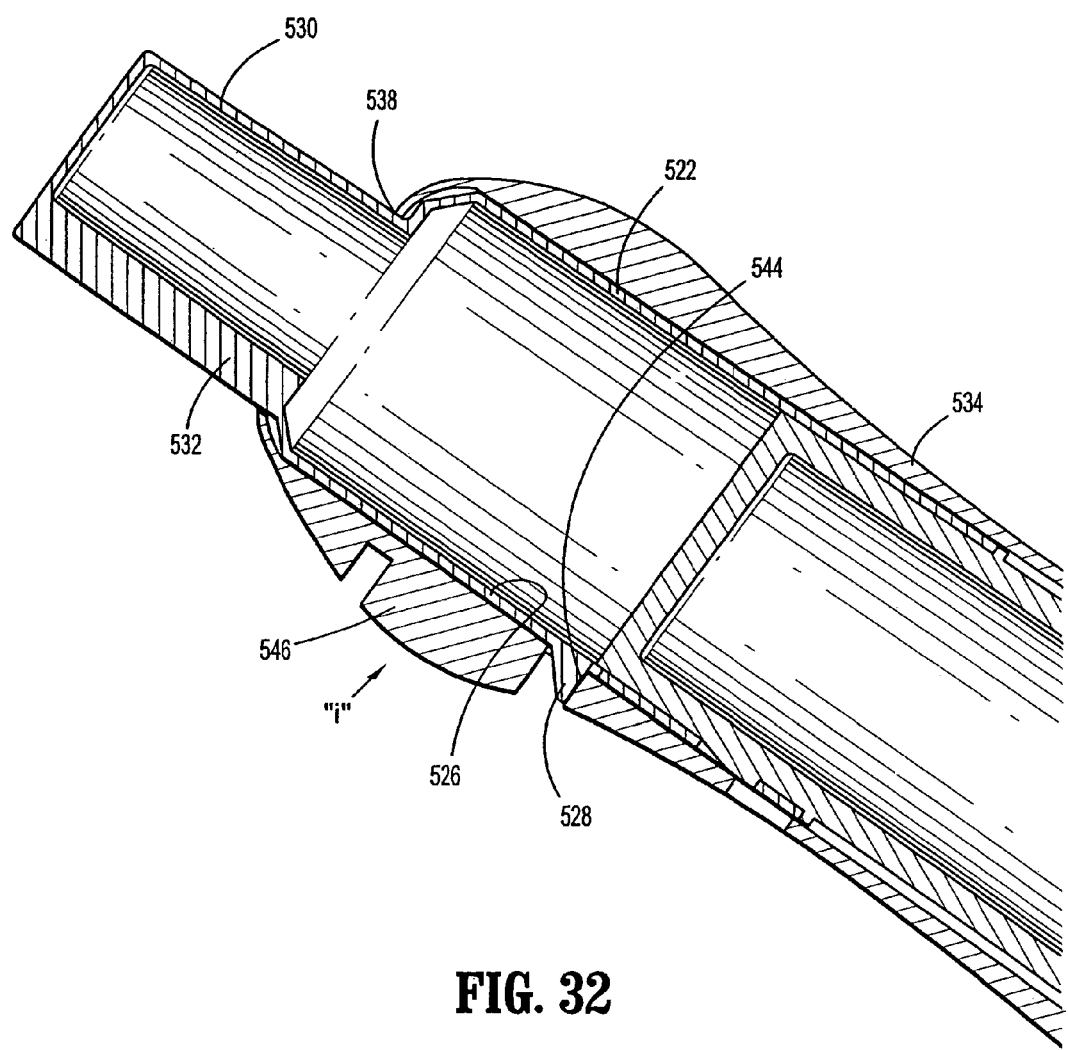
FIG. 32 is a side cross-sectional view of the proximal end of the skin applicator apparatus illustrating the relationship of the locking lever and the release lever of the outer housing and the housing extension.

Outer housing 534 further defines opening 542 (FIG. 31) in its outer wall for at least partially accommodating locking lever 526 of housing extension 522. Opening 542 defines distal locking surface 544 which is engaged by locking shelf 528 of locking lever 526 of housing extension 522 when in the first transit position of fluid housing 506 (FIG. 32). Outer housing 534 incorporates release lever 546 which extends within opening 542 of the outer housing 534 in superposed relation to locking lever 526 of housing extension 522. Release lever 546 pivots radially inwardly about its living hinge to engage and cause corresponding pivotal movement of locking lever 526 to release locking shelf 528 from its engagement with locking surface 544. In this orientation, housing extension 522 and fluid housing 506 are permitted to move in a longitudinal direction to the second actuated position.

Referring now to FIGS. 33 and 36-38, applicator head assembly 504 will be discussed. Applicator head assembly 504 includes applicator frame 548 and absorbent applicator member 550 attached to the applicator frame 548. Applicator frame 548 includes throat 552 defining an internal bore for reception of end cap 508 and fluid housing 506. Throat 552 has at least one opening 552a (FIG. 31) in its outer wall for accommodating a corresponding locking projection 554 of outer housing 534 to fixedly secure applicator frame 548 to the outer housing 534.

Figure 36:
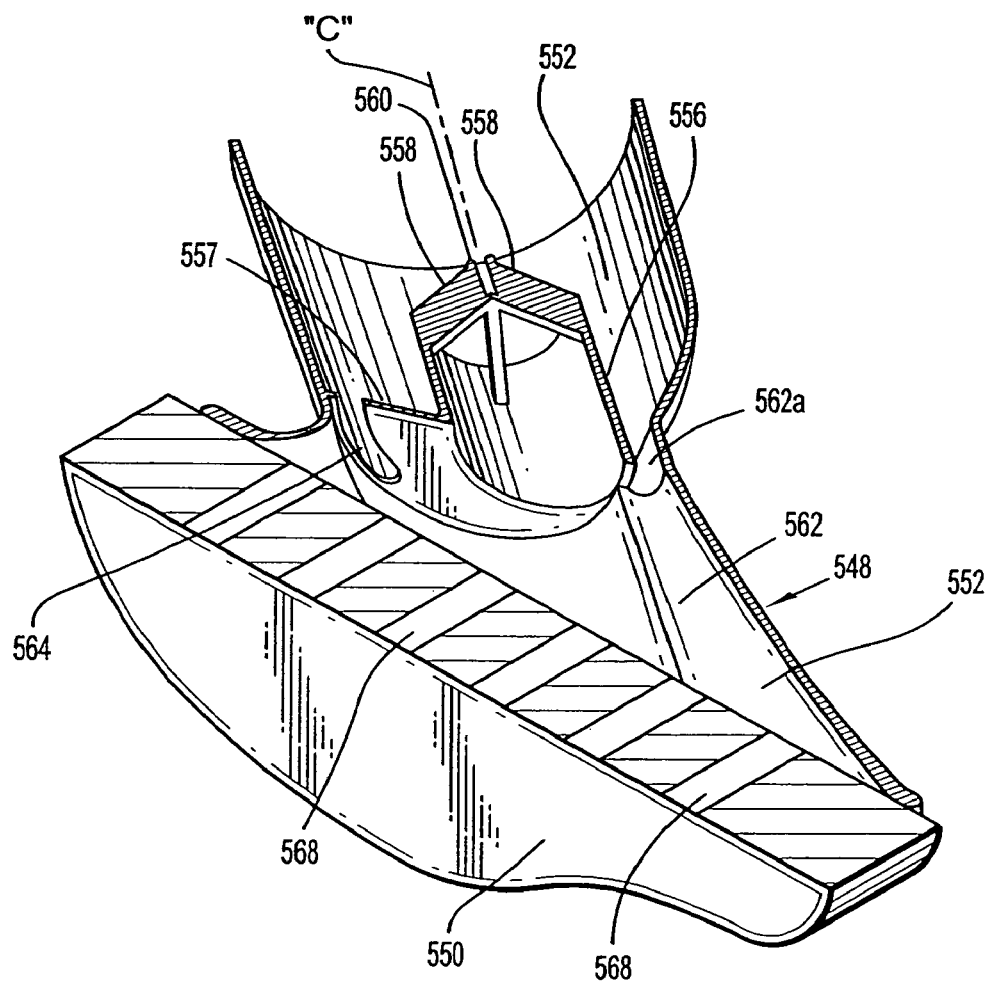
FIG. 36 is a perspective view in cross-section of the applicator frame and absorbent member of the applicator head assembly.
Figure 37:
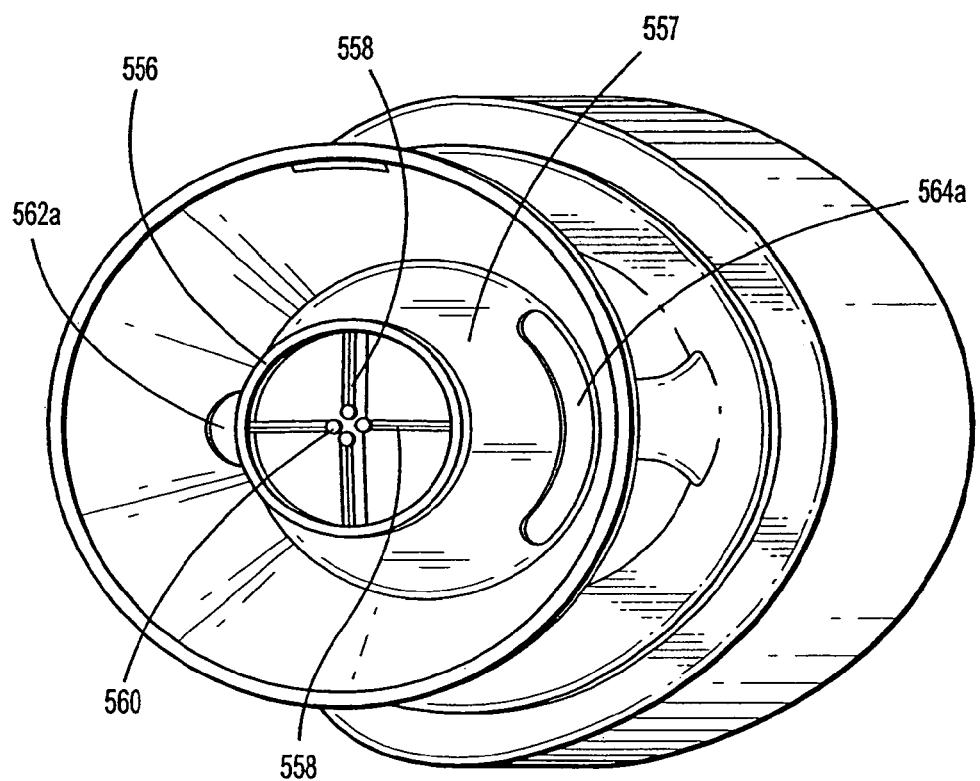
FIGS. 37-38 are additional perspective views of the applicator frame.

As best depicted in FIGS. 33, 36-37, within the interior of throat 552 is internal collar 556 mounted to transverse wall 557, and a plurality of penetrating members 558 extending from the internal collar 556. Penetrating members 558 are preferably four in number and are arranged along intersecting planes to define four quadrants when the penetrating members 558 pierce liner 510. More or less than four penetrating members 558 are also envisioned. Specifically, each penetrating member 558 extends to a point 560 with each of the points 560 of the penetrating members 558 being disposed about a central axis "c" in adjacent spaced relation as shown.

Figure 38:
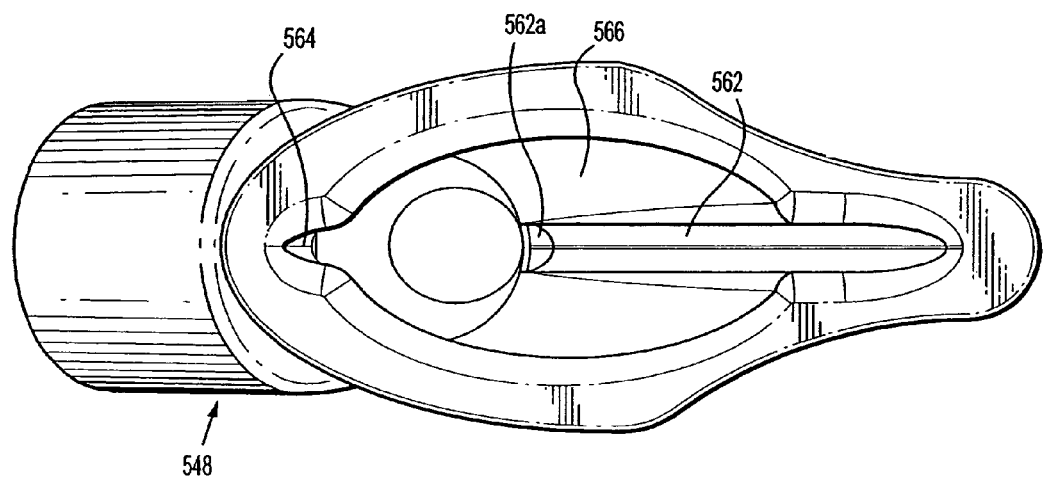

Referring now to FIGS. 36-38, applicator frame 548 further defines first and second channels 562, 564 disposed about the periphery of internal collar 556 adjacent upper and lower areas of throat 552. First and second channels or manifolds 562,564 facilitate passage of the medical agent or fluid directly to the leading and trailing ends, respectively, of applicator member 550. First channel 562 is generally semicircular in cross-section and extends from semicircular passage 562a adjacent the periphery of internal collar 556 to the upper or forward end of applicator frame 548. Second channel 564 extends from an arcuate or crescent shape opening 564a within transverse wall 557 and is in communication with the lower or rear end of applicator frame 548. Applicator frame 548 further defines central enlarged orifice 566 which extends to the lower surface of applicator frame 548. Orifice 566 is in fluid communication with first and second channels 562, 564, and is sized to expel a substantial volume of fluid onto the central area of absorbent member 550.

Figure 39:
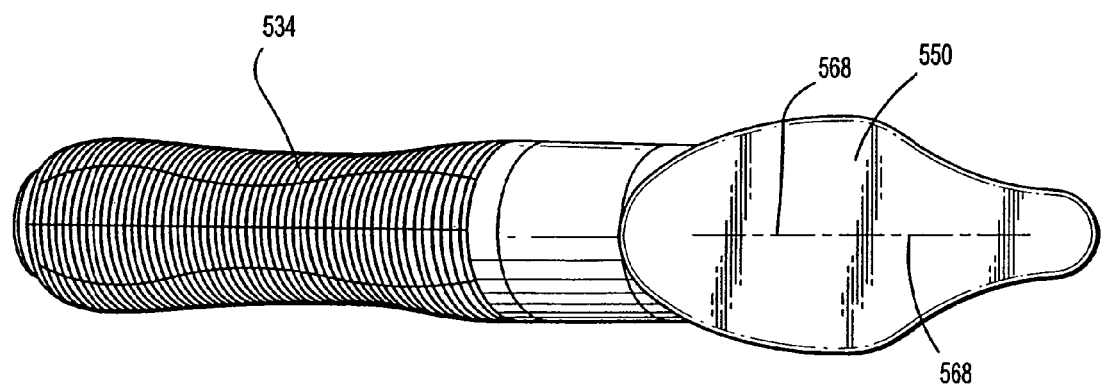
FIG. 39 is a bottom plan view of the applicator apparatus.

Referring now to FIGS. 36 and 39, absorbent member 550 is substantially similar in shape to the absorbent members discussed hereinabove and is preferably in the form of an absorbent sponge, foam, etc. Absorbent member 550 is mounted to the lower surface of applicator frame 548 via conventional means. Absorbent member 550 includes a plurality of spaced slits 568 which extend completely through the thickness of the absorbent member 550 along the central axis of absorbent member 550. Slits 568 function as zero closure valves, i.e. the slits 568 are adapted to remain closed in the absence of pressure to absorbent member 550 but will open when pressure is applied to the absorbent member 550 to permit the fluid to flow therethrough.

In use, the practitioner grabs apparatus 500 with a single hand preferably about outer housing 534. Thereafter, to activate apparatus 500, the practitioner engages release lever 546 of outer housing 534 and depresses the release lever 546 in a radially inward direction "i" as depicted in FIG. 32. Release lever 546 pivots about its living hinge to engage locking lever 526 of housing extension 522 to cause corresponding inward movement of the locking lever 526. As locking lever 526 pivots inwardly, locking shelf 528 of locking lever 526 is released from its engagement with locking surface 544 of outer housing 534. In this position, housing extension 522 and fluid housing 506 are free to move in the longitudinal direction.

Figure 40:
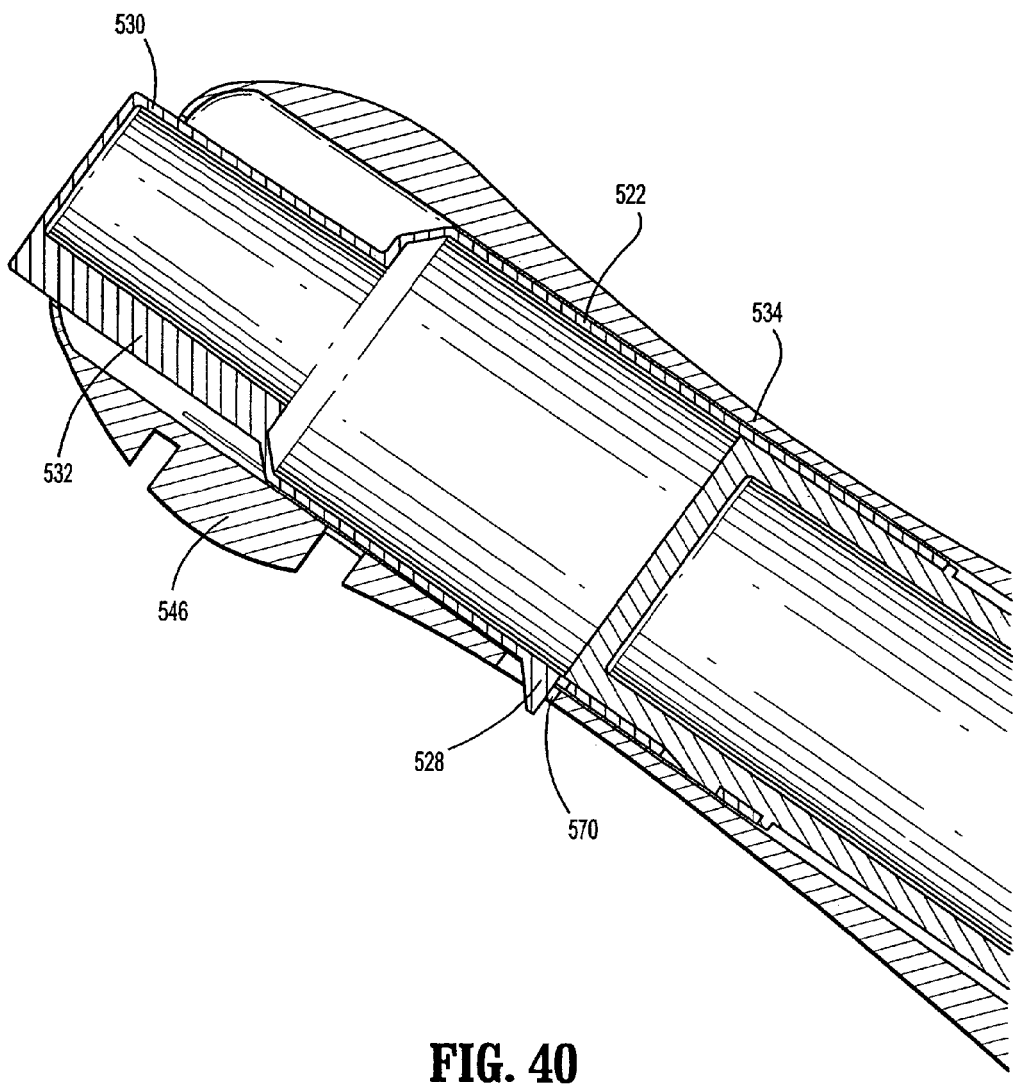
FIG. 40 is a side cross-sectional view similar to the view of FIG. 32 illustrating release of the locking lever and movement of the housing extension and the fluid housing to the second actuated position.
Figure 41:
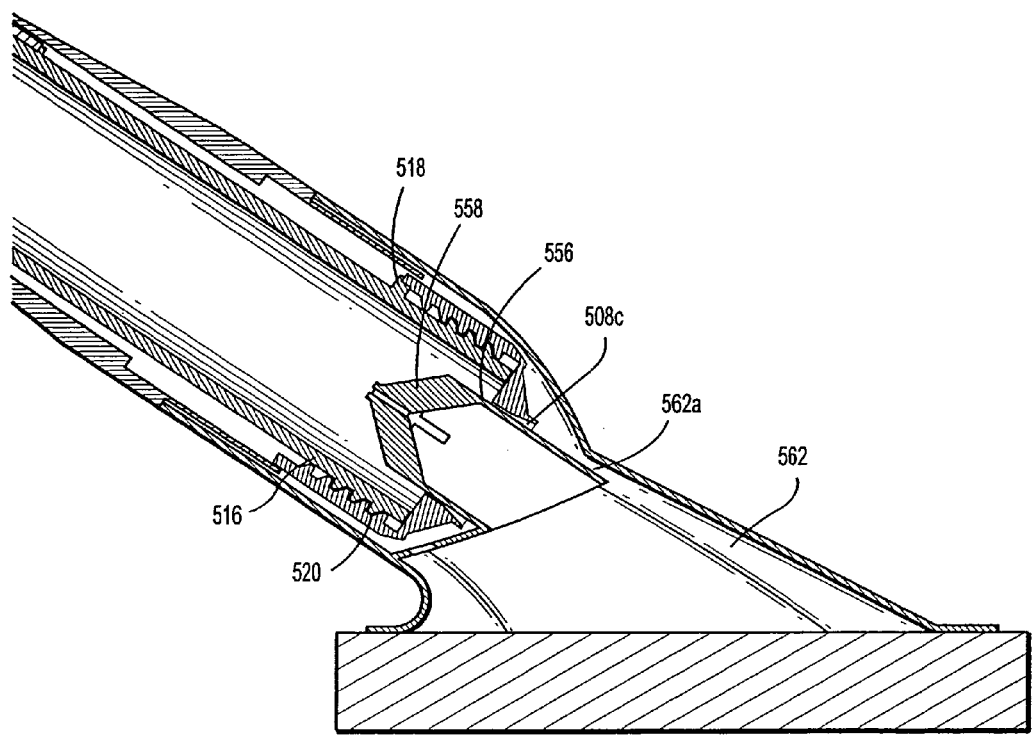
FIG. 41 is a side cross-sectional view similar to the view of FIG. 33 illustrating the relationship of the components subsequent to movement to the second actuated position.
Figure 42:
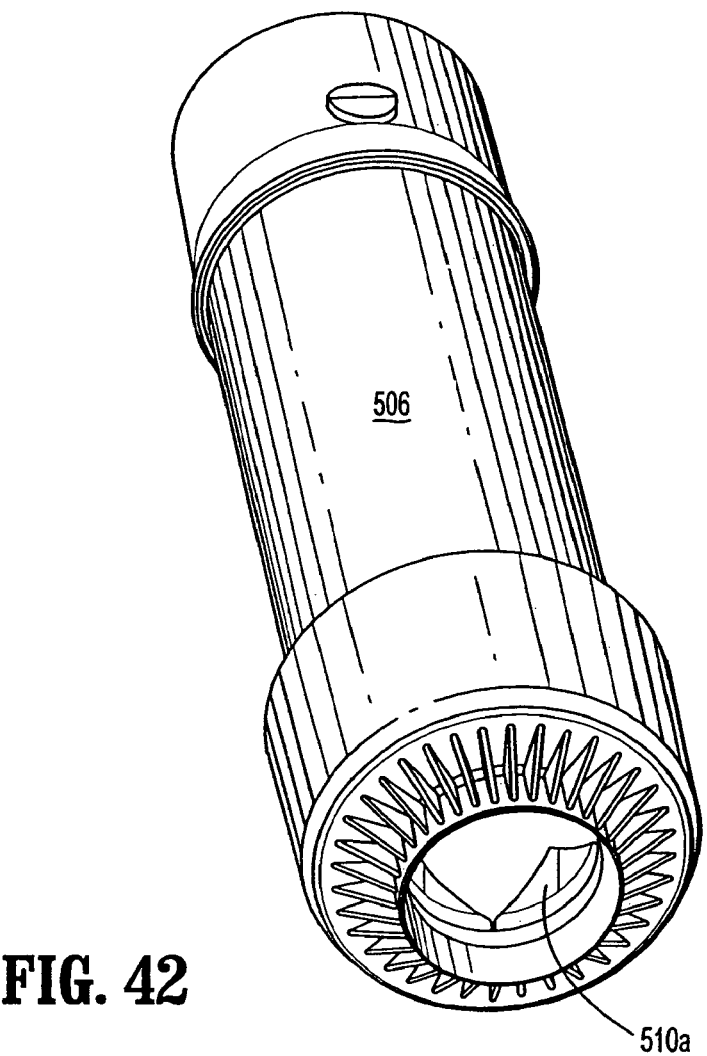
FIG. 42 is a perspective view of the fluid housing and liner subsequent to movement to the second actuated position.
Figure 43:
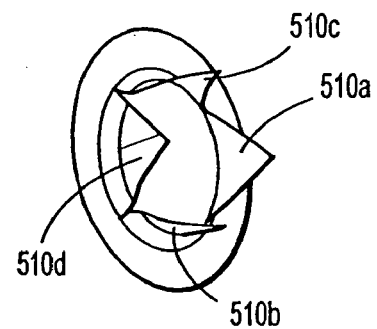
FIG. 43 is an enlarged perspective view of the pierced liner.

Referring now to FIG. 40, the practitioner thereafter advances button 530 at the proximal end of housing extension 522 with the heel of his hand or, alternatively, with the thumb of the practitioner. The activation force required (approximately 8-12 lbs makes it possible to thumb activate if desired) to advance housing extension 522 and fluid housing 506 in a distal direction relative to outer housing 534 and applicator head assembly 504 (FIG. 41). With particular reference now to FIG. 42-43, distal direction of fluid housing 506 causes liner 510 to be penetrated by the four penetrating members 558 which results in the liner 510 being pierced into four quadrants portions 510a-d. The stroke involved allows the foil to be stripped over the sidewall of the piercing cylinder thereby providing the full diameter for fluid flow. Upon rupture of liner 510, the medical agent within fluid housing 506 is expelled almost instantaneously through internal bore of internal collar 556 and into first and second channels 562, 564 for dispensing within enlarged orifice 566 of applicator frame 548. Enlarged orifice 566 is of substantial dimension such that the cohesive force associated with the medical agent is overcome by the mass of the fluid. This allows the fluid to "tumble out" in seconds via gravitational forces, i.e., no compression of the fluid housing is necessary. In addition, first channel 562 directs fluid to the elongated neck section of applicator member and second channel 564 directs fluid to the rear area. In this manner, a uniform layer of fluid is distributed to the absorbent member 550. Furthermore, first and/or second channels 562, 564 may establish an equilibrium within applicator frame 548 by permitting air to pass within the interior of applicator frame 548 thus ensuring a sufficient flow of the medical agent. Preferably, either or both of first and second channels 562, 564 may provide a vent permitting the air displaced during compression of absorbent member 550 to be directed back through channels 562, 564 through respective openings or passages 562a, 564a and into applicator frame 548 for venting to the atmosphere. FIG. 33 illustrates the manner in which first channel 562 extends through passage 562a about collar 556 and communicates with the interior of applicator frame 548. The assembly tolerance associated with the components of apparatus 500 is sufficient to permit the air to vent. Furthermore, in the actuated position, distal collar 508c of end cap 508 hermetically seals about the outer surface of internal collar 556 to prevent leakage toward the proximal end of the applicator frame (see FIG. 41). This arrangement may also serve as a friction fit or interference fit which retains fluid housing in the second actuated position. A volume of medical agent may pass back through passage 562a or opening 564a of transverse wall 557 during compression of absorbent member 550 to accommodate volumetric displacement of the fluid. It is further noted that fluid housing 506 may be retained in the second actuation position by engagement of locking shield 528 of locking lever 526 with a corresponding position locking aperture 570 within the outer wall of outer housing 534 (see e.g., FIG. 40).

As described above, the applicator apparatus of the present disclosure includes key features and advantages not found in the prior art. Whereas the prior art requires two-handed use and high force activation, the present disclosure provides single-handed triggering and light activation pressure similar to activating a click-pen. This results in less hand fatigue and no "smacking" is required. Neither a snap ring nor a high activation force is required to prevent misfire, and no parts require removal prior to use. Instead, a single step, squeeze-to-release shipping lock prevents unintended activation, and the minimum number of parts reduces complexity and manufacturing cost. In addition, prior art applicator handles are smooth, straight, and angled at 45 degrees, resulting in limited comfort and control. In contrast, the ergonomic handle of the present disclosure is ribbed for comfort and traction even when wet. The handle's hourglass contour and rounded end accommodate any size hands, and a reduced handle angle between 30-40 and preferably 35 degrees permits greater access and control. While the prior art includes restrictive conduits or mesh to retard fluid transfer, the wide mouth bottle of the present disclosure allows the mass of antiseptic to overcome surface tension and to drain rapidly to the absorbent member. The bottle contents evacuation is also speeded by the double piercing means which creates air ingress over the fluid layer in the fluid housing. Prior art sponges are shaped symmetrically to compensate for lack of manifolds. In contrast, the "c channel" manifolds of the present disclosure uniformly wet opposing ends of the asymmetric sponge. While prior art devices work poorly when inverted due to small sponge capacity and slow fluid transfer, the present disclosure provides for inverted use and faster prep since the large sponge acts as a reservoir for rapidly transferred fluid. The prior art includes a square sponge head and performs poorly on contoured topology. However, the contoured multi-use sponge conforms to any patient topology, and the integrated sponge neck region provides the dexterity of a conventional sponge stick with the speed of an applicator. The sponge has a thickness T that is twice the thickness of the prior art, which inures less risk injury to patient, and the longer sponge length L allows for faster prep.

The components of medical skin applicator apparatus may be fabricated from materials suitable for medical applications, such as, for example, polymerics or metals, such as stainless steel, depending on the particular application and/or preference of a practitioner. Semi-rigid and rigid polymerics are contemplated for fabrication, as well as resilient materials, such as molded medical grade polypropylene. One skilled in the art, however, will realize that other materials and fabrication methods suitable for assembly and manufacture, in accordance with the present disclosure, also would be appropriate.

Figure 44:
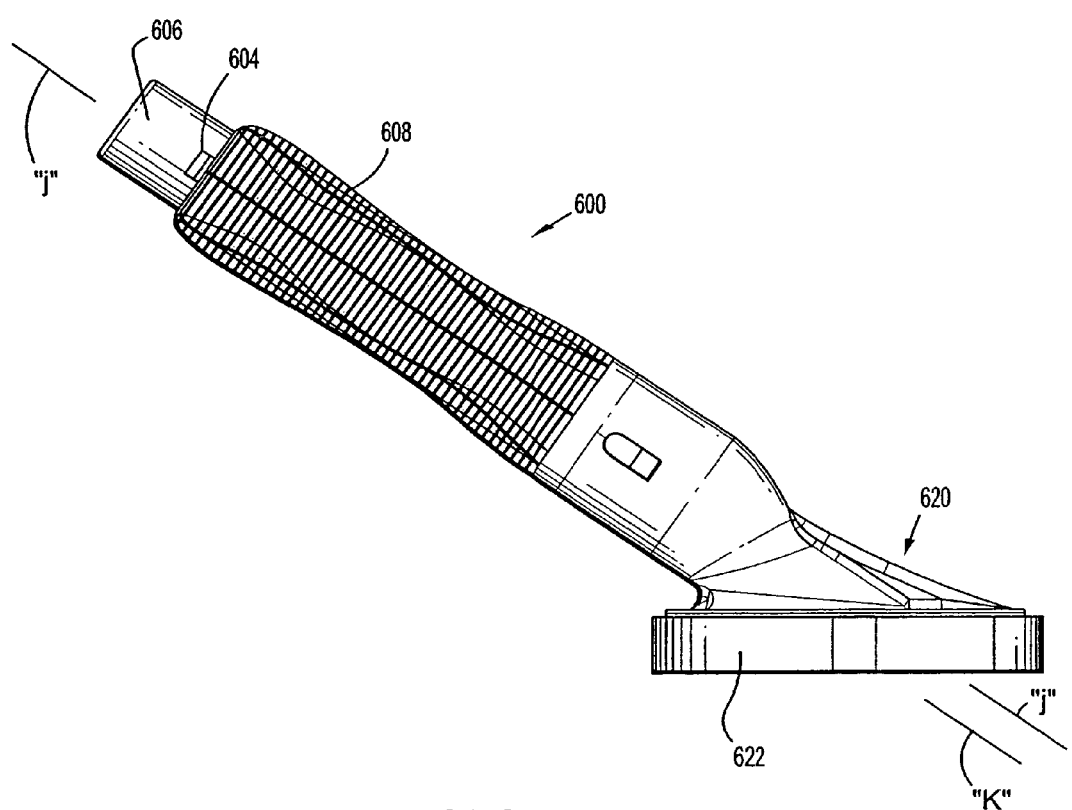
FIG. 44 is a side plan view of another alternate embodiment of the skin applicator apparatus of the present disclosure.
Figure 45:
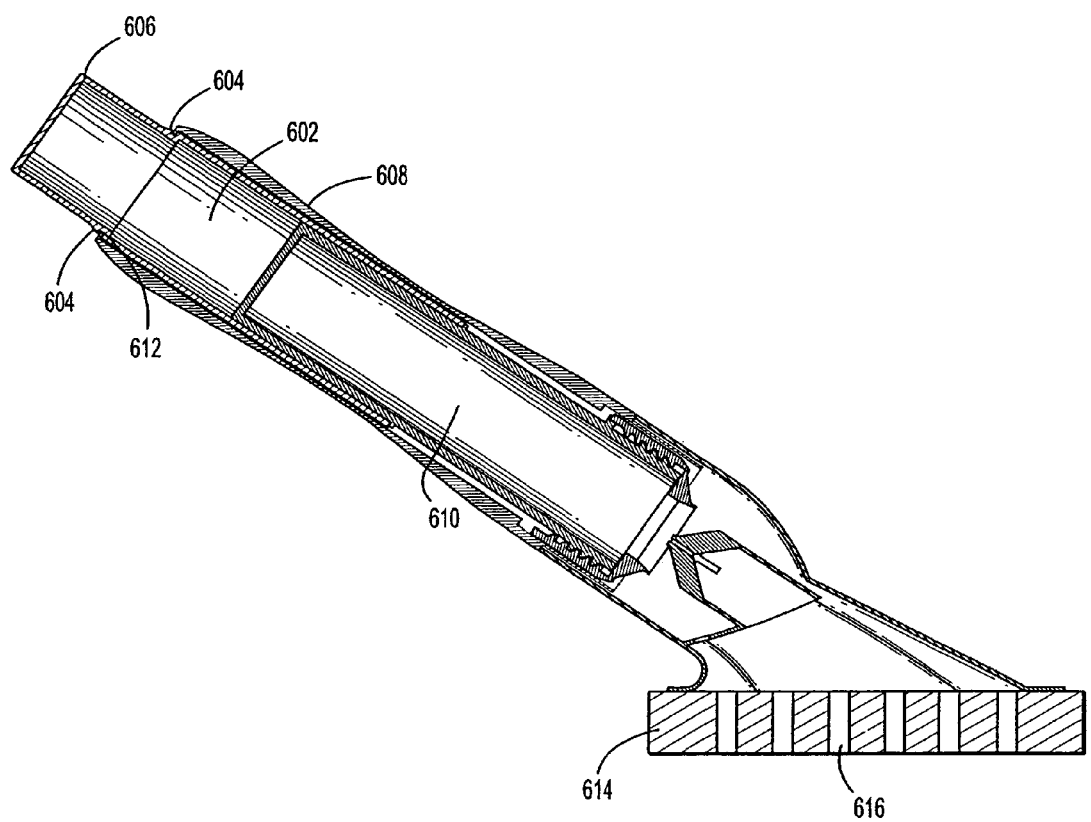
FIG. 45 is a side cross-sectional view illustrating the fluid housing in the first transit position.
Figure 46:
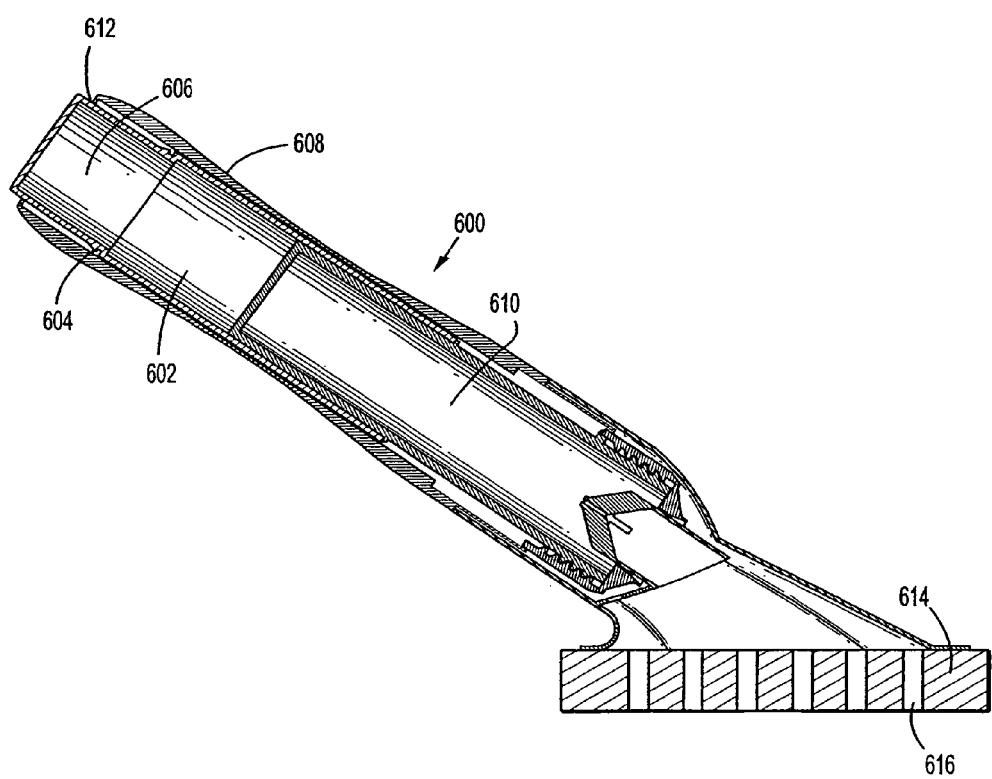
FIG. 46 is a side cross-sectional view illustrating the fluid housing in the second actuated position.

FIGS. 44-46 illustrate an alternate embodiment of the present disclosure. In accordance with this embodiment, skin applicator apparatus 600 incorporates an alternate mechanism to releasably secure the fluid container assembly in the first transit position. In particular, housing extension 602 includes a pair of outer circumferential partial ribs 604 in diametrically opposed relation on the outer surface of button 606. Ribs 604 reside beyond outer housing 608 in the first transit position of fluid housing 610 depicted in FIGS. 44-45. Outer housing 608 defines a restricted opening 612 at its proximal end, which has an internal dimension or diameter less than the effective cross-sectional dimension of housing extension 602 across and inclusive of partial ribs 604. Thus, partial ribs 604 prevent passage of housing extension 602 through opening 612 of outer housing 608. When it is decided that apparatus 600 will be actuated, the practitioner exerts a distal pressure to button 606 of housing extension 602 which causes partial ribs 604 and/or the respective walls of housing extension 602 and outer housing 608 to flex, deform, etc. to permit passage of the partial ribs 604 through the restricted opening 612 thereby enabling fluid housing 610 to move to its second actuated position depicted in FIG. 46. It is further envisioned that housing extension 602 may be secured in the second actuated position through the provision of internal locking tabs or recesses within outer housing 608. The internal tabs or recesses may be appropriately dimensioned to engage, receive, the partial ribs 604 in a secured relation. Absorbent member 614 includes a plurality of openings 616 extending completely through its thickness as disclosed in FIG. 45. Openings 616 replace the slits of prior embodiments Another feature of applicator apparatus 600 and apparatus 500 of FIG. 44 is the arrangement of the handle component relative to applicator head assembly. In particular, the handle components of these apparatuses are displaced relative to the applicator head assembly which facilitates manipulation of the apparatuses about the operative site. In particular, outer housing 608 and the internal components forming the fluid container assembly are arranged along a handle axis "j" as shown in FIG. 44. Applicator head assembly 620 including applicator frame 622 is coaxially arranged about axis "k". As appreciated axis "k" is vertically displaced relative to axis "j" by a predetermined distance but is preferably in parallel relation. This offset allow the practitioner to maintain the most preferred 35 degree relationship with the patient while allowing for additional clearance due to this offset thereby maintaining a "comfort zone" in relation to the patient's skin, e.g., the practitioner's hand is displaced from the patient to enhance maneuverability around the operation site.

Figure 47:
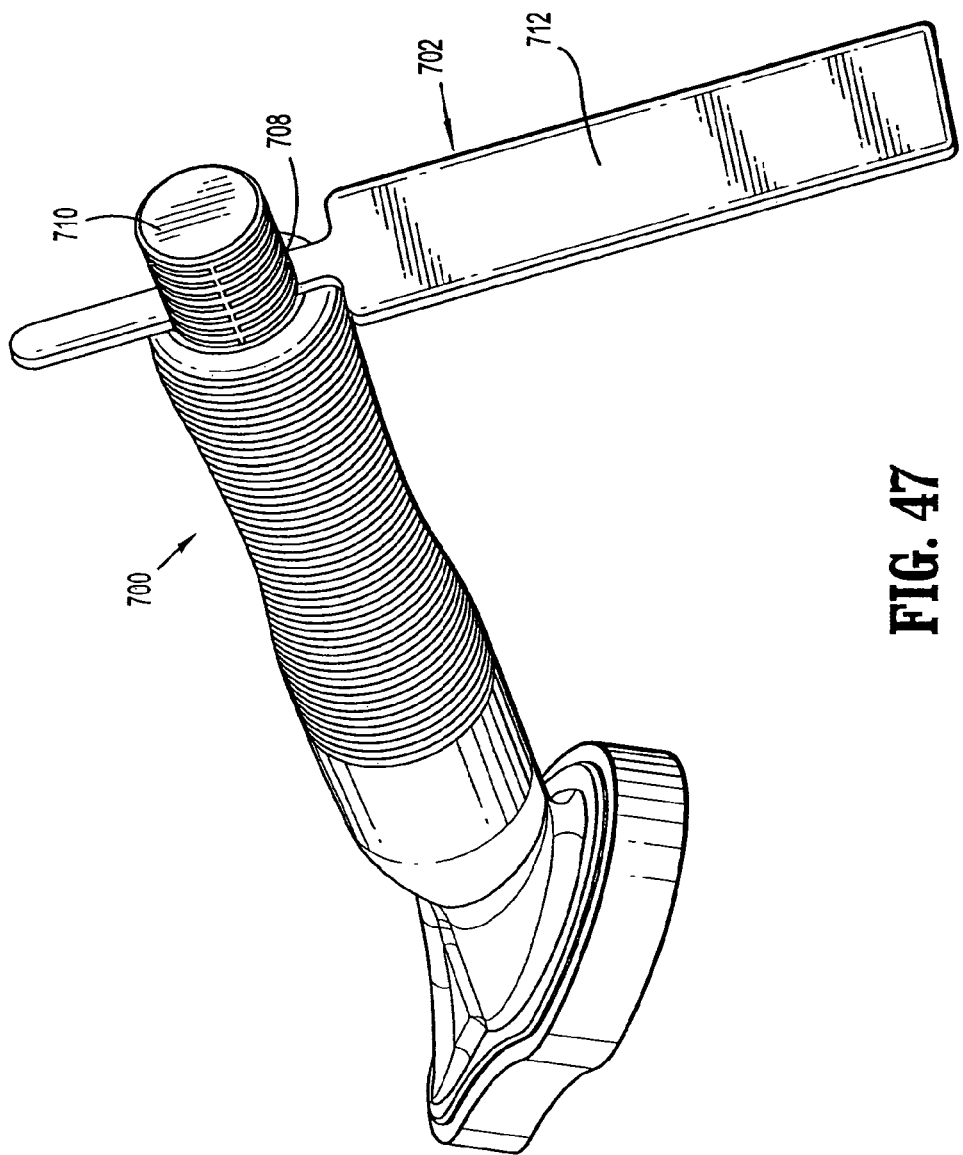
FIG. 47 is a perspective view of another alternate embodiment of the skin applicator apparatus of the present disclosure.
Figure 48:
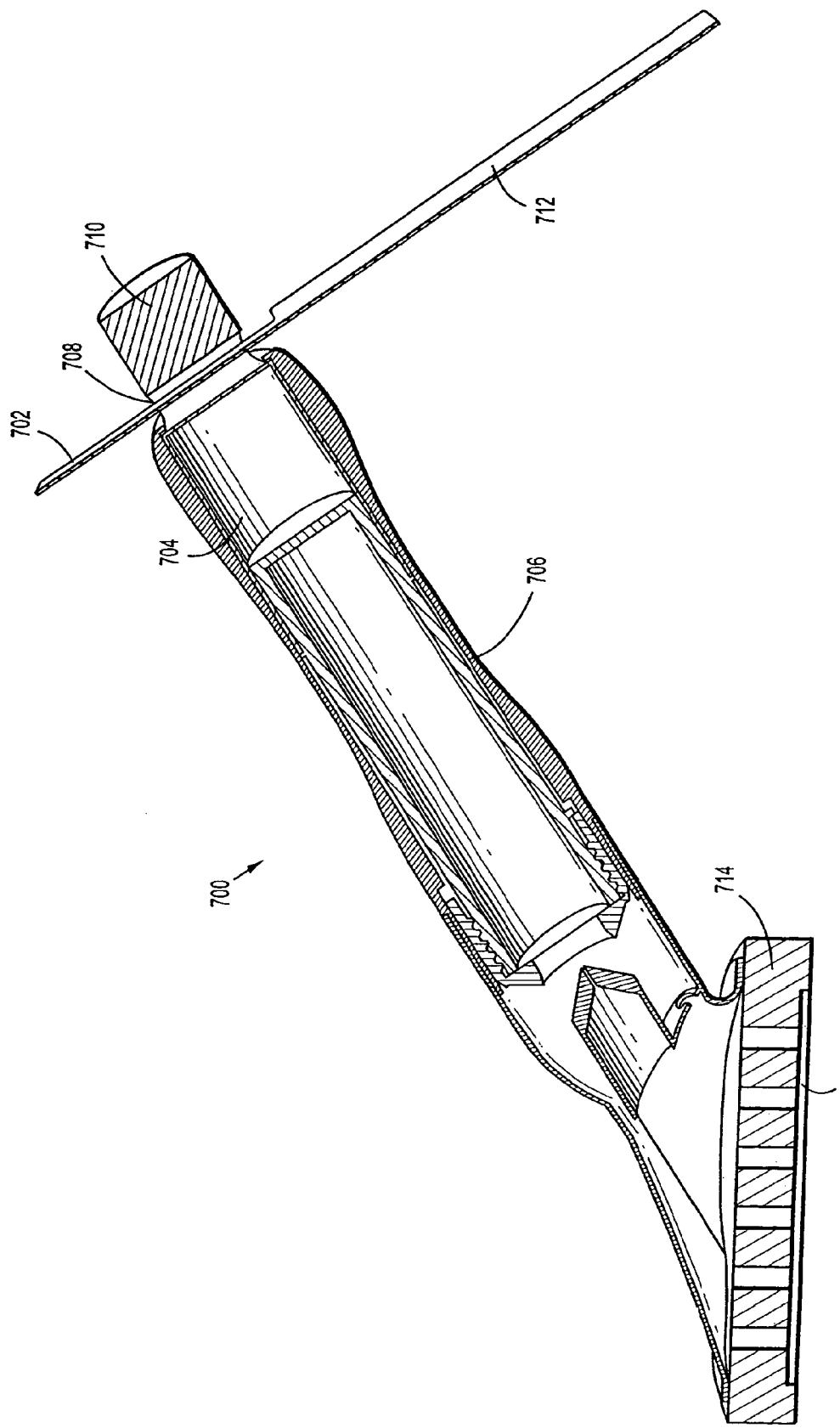
FIG. 48 is a side cross-sectional view of the skin applicator apparatus of FIG. 47.

FIGS. 47-48 illustrate another alternate embodiment of the skin applicator apparatus of the present disclosure. In accordance with this embodiment, skin applicator apparatus 700 is releasably secured in its transit position via detachable tag 702. In particular, housing extension 704 attached to fluid housing 706 includes transverse bore 708 within manually engageable button 710. Releasable tag 702 is positioned within transverse bore 708 and when positioned within the bore 708 prevents advancement of housing extension 704 and attached fluid housing (not shown) thereby releasably securing apparatus 700 in the first transit position. Releasable tag 702 may be removed from transverse bore 708 to permit activation of the apparatus and movement of the fluid container assembly to the second actuated position. Releasable tab 702 may be fabricated from any solid or flexible material and preferably incorporates handle 712 to facilitate grasping by the practitioner. Absorbent member 714 of the applicator head assembly preferable incorporates longitudinal channel 716 in its lower surface to provide a greater volume of fluid flow. Channel 716 may be in connection with slots or openings extending through the absorbent member 714.

Figure 49:
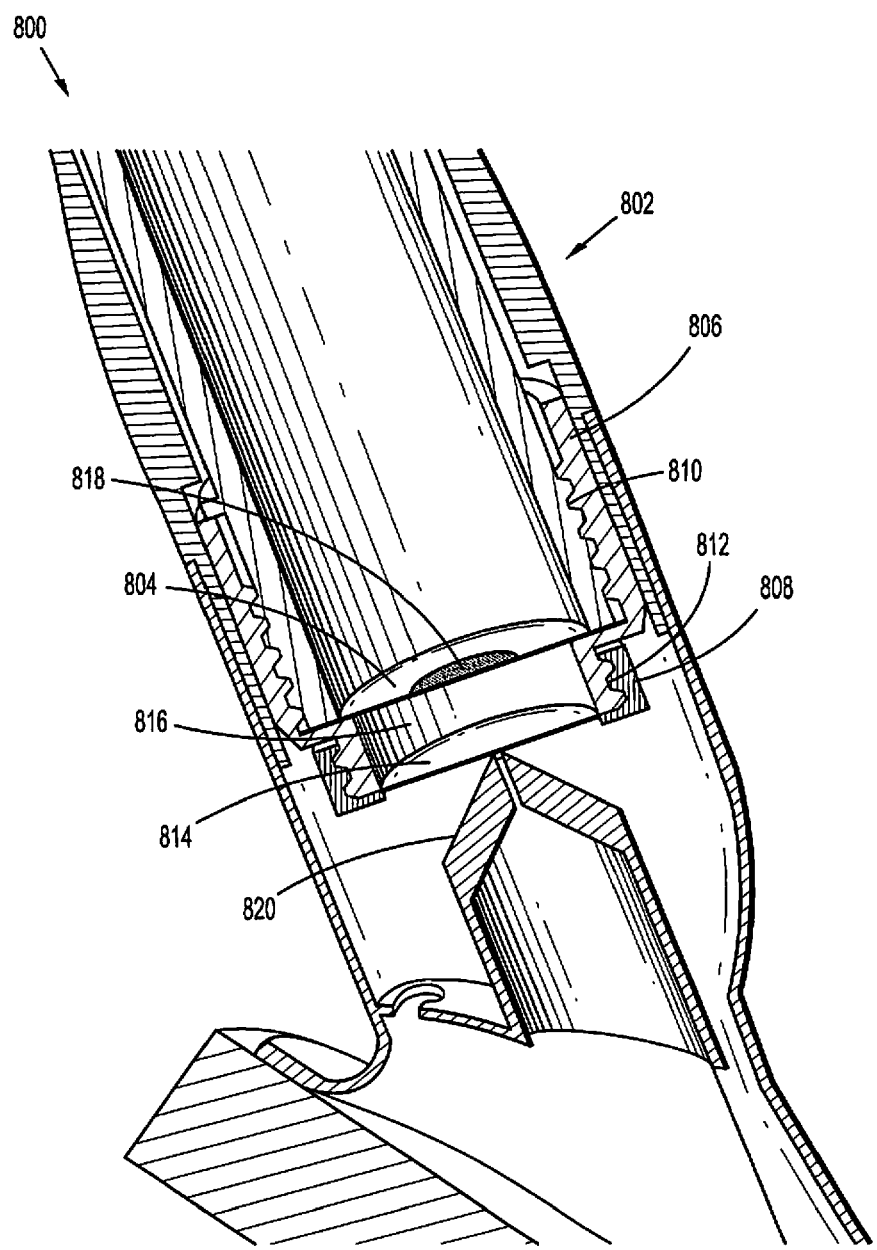
FIG. 49 is a partial side cross-sectional view of another embodiment of the skin applicator apparatus of the present disclosure.
Figure 50:
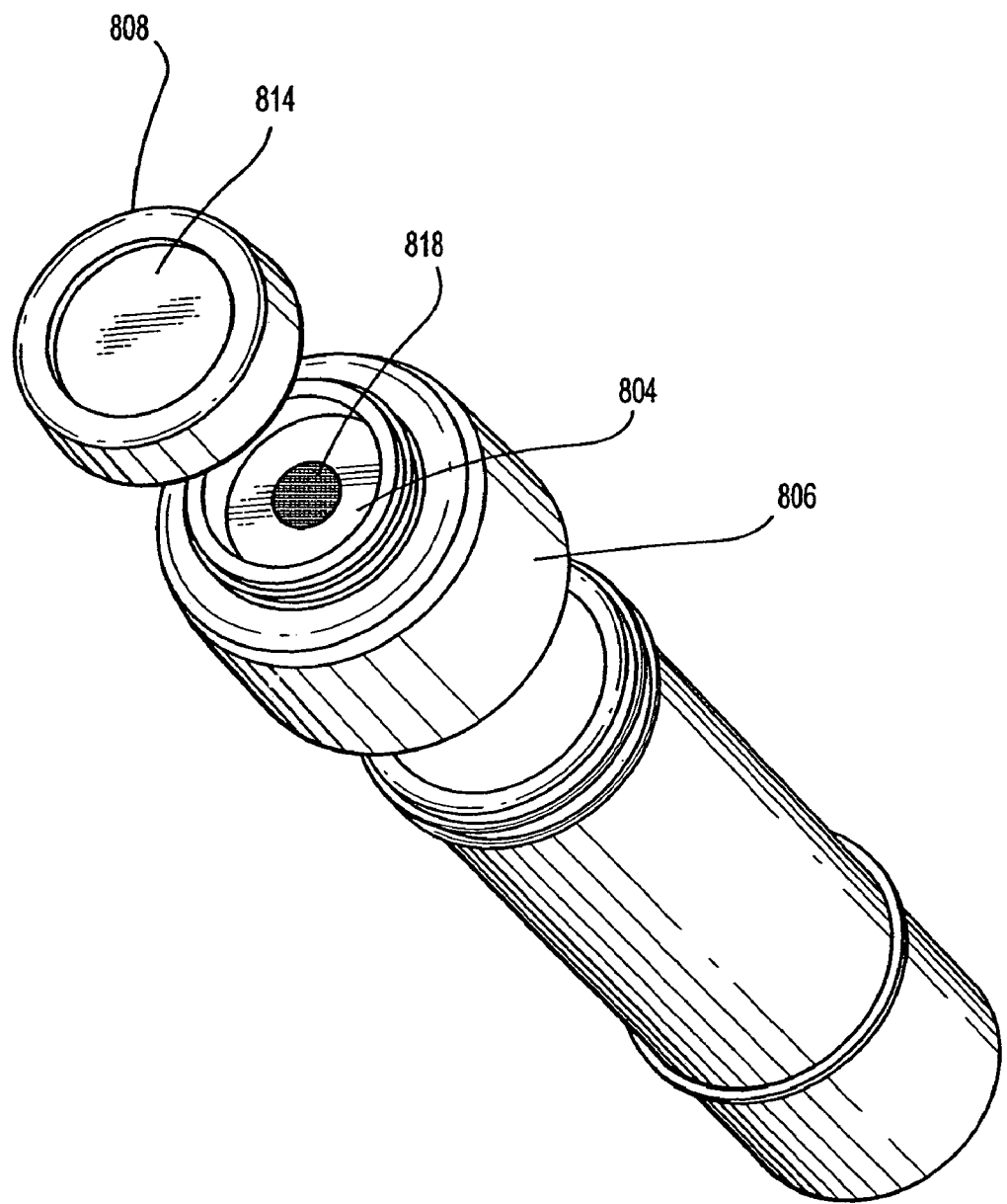
FIG. 50 is an exploded perspective view of the skin applicator apparatus of FIG. 49.

FIGS. 49-50 illustrate another alternate embodiment of the present disclosure useful for dispensing clear antiseptics such as Chlorhexidine Gluconate/Alcohol solutions. Clear antiseptics pose a problem to practitioners since it is difficult to verify the area of coverage after application. Skin applicator apparatus 800 is substantially similar to the skin applicator apparatus discussed in connection with FIG. 29 but further includes a dye chamber for introducing a dye or coloring agent to the medical agent or fluid. Specifically, fluid housing 802 has foil liner 804 connected thereto as discussed hereinabove and first end cap 806 threadably mounted to the housing 802. Apparatus 800 further includes second end cap 808 mounted to first end cap 806. In one preferred arrangement, first end cap 806 includes external threads 810 and second end cap 808 includes corresponding internal threads 812 which threadably engage the external threads 810 to secure the second end cap 808 to the first end cap 806. Second end cap 808 also includes foil liner 814 secured within the interior of the end cap. In the mounted condition of second end cap 808 to first end cap 806, a chamber 816 is defined between the respective foil liners 814, 804 of the two components. A dye or coloring agent 818 is stored within chamber 816. A suitable dye is FD&C green #3 dye manufactured by Parchem Trading Ltd. White Plains, N.Y. 10601. During actuation of the apparatus, the penetrating members 820 of applicator frame 822 pierce both liners 814, 804 whereby the dye 818 within chamber 816 mixes with the medical agent during passage through applicator frame 822. The dye thus colors the medical agent or antiseptic to a desired color.

Figure 51:
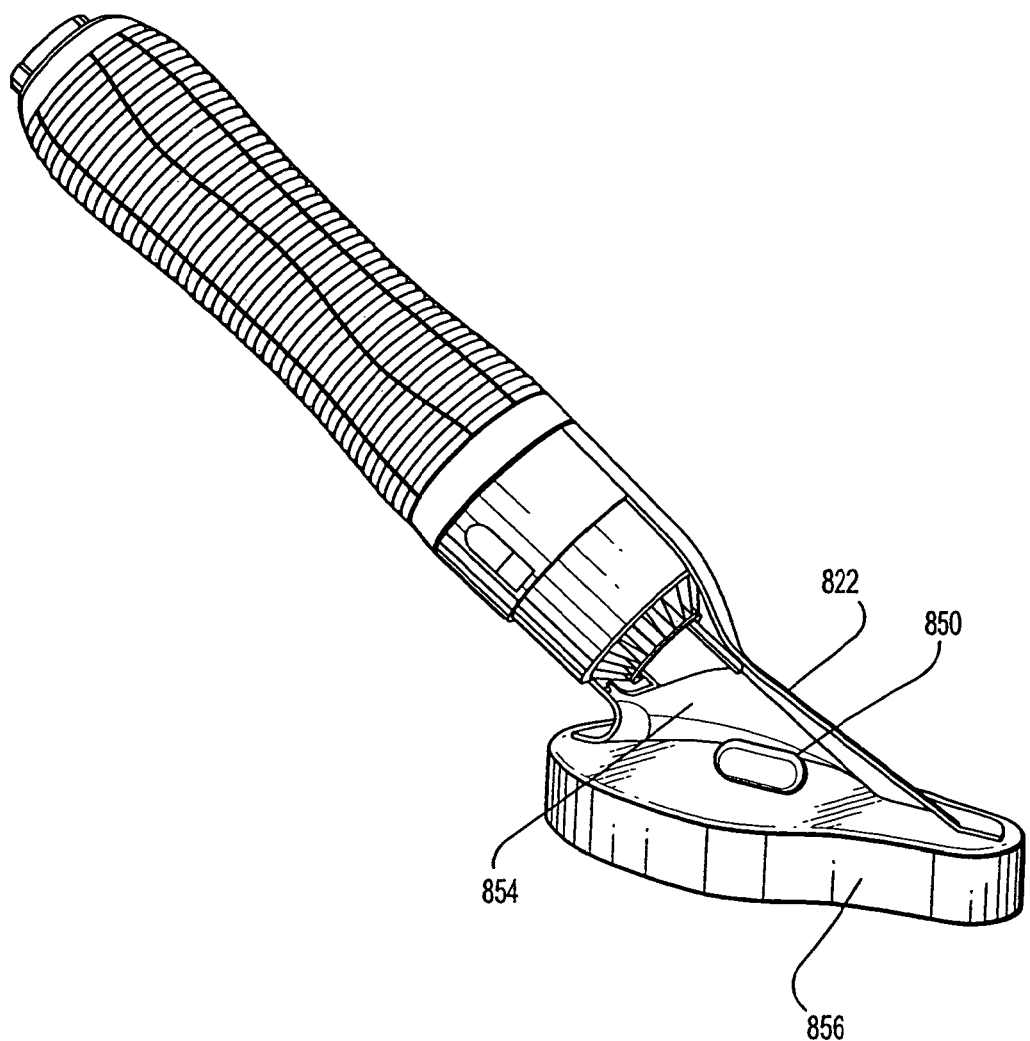
FIG. 51 is a perspective view in partial cross-section of another embodiment of the skin applicator apparatus of the present disclosure.

FIG. 51 illustrates an alternate embodiment in which a dye tablet 850 is positioned within applicator frame 822. Preferably, the tablet 850 containing the dye is positioned within internal conduit 854 adjacent absorbent member 856. The dye tablet is contacted by the medical agent as it is transferred to the absorbent member 856. The dye tablet may be composed of the dye discussed in connection with the embodiment of FIGS. 49-50.

Figure 52:
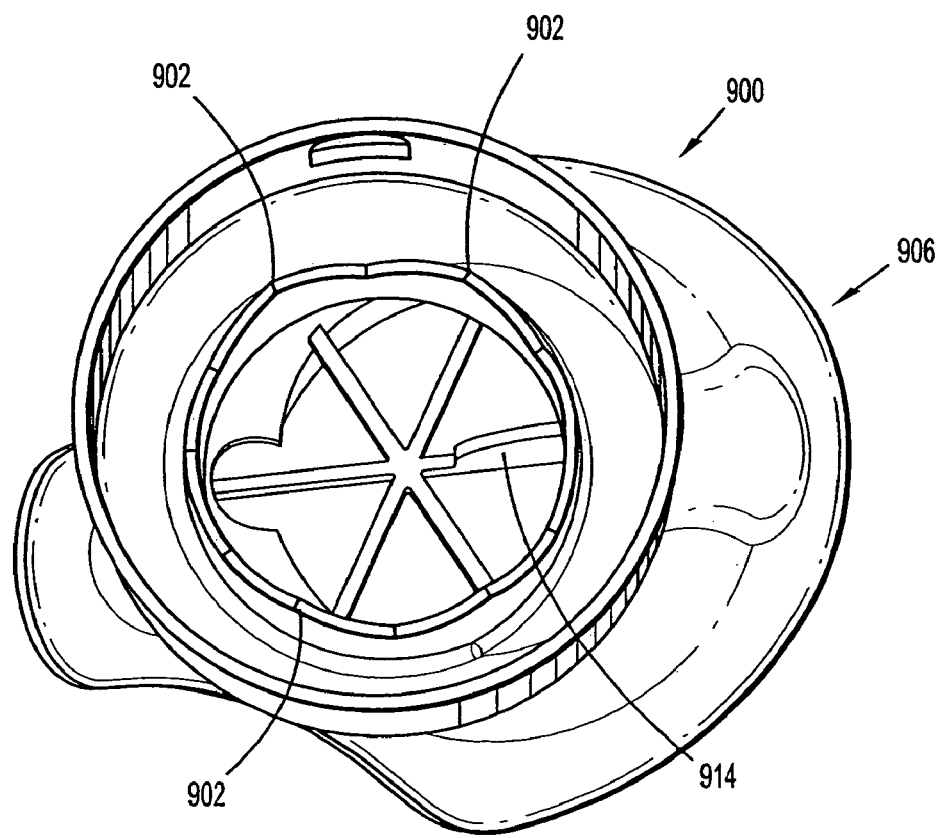
FIG. 52 is a perspective view of an alternate embodiment of the skin applicator apparatus of the present disclosure where applicator frame has a circular array of penetrating members.
Figure 53:
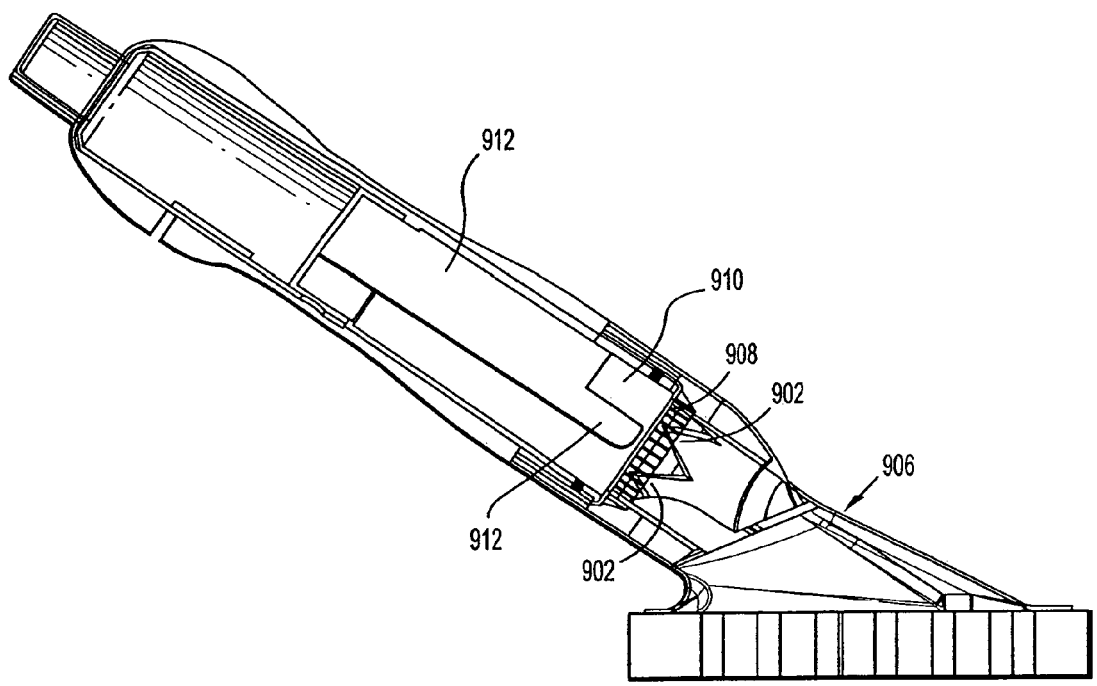
FIG. 53 is a side cross-sectional view of the skin applicator apparatus of FIG. 52 in the first transit position thereof.
Figure 54:
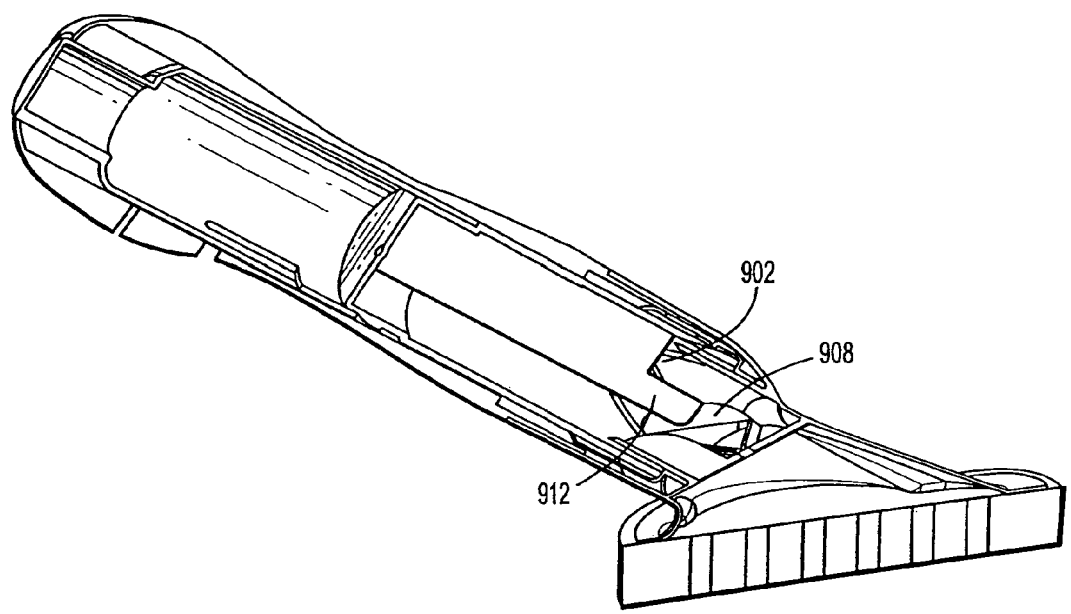
FIG. 54 is a side cross-sectional view of the skin applicator apparatus in the second actuated position.
Figure 55:
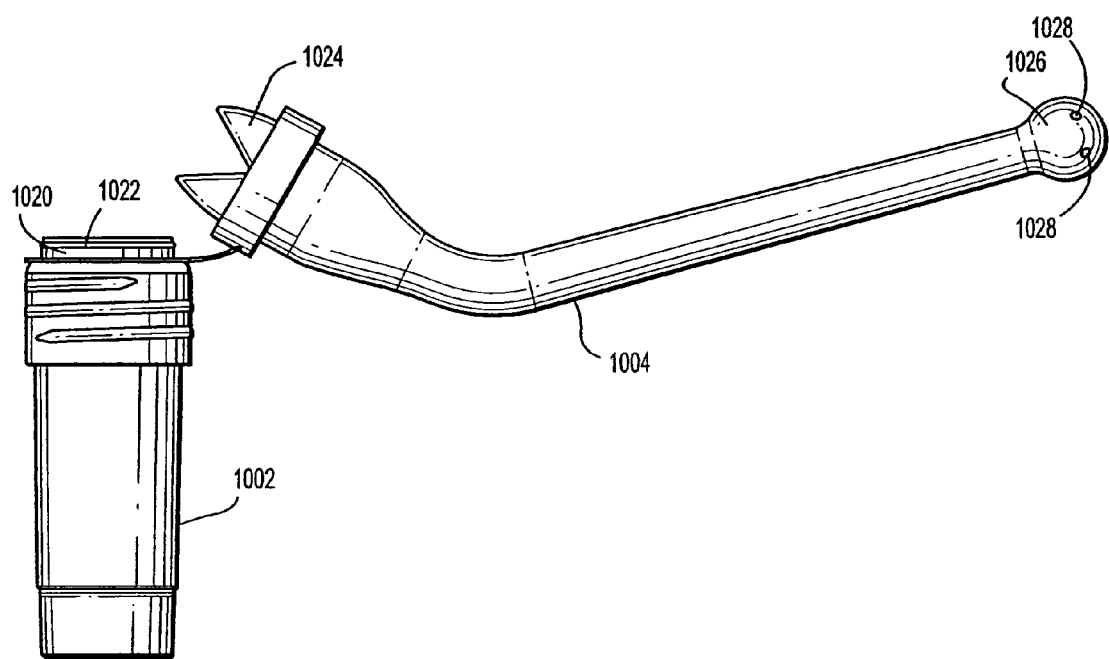
FIG. 55 is a side plan view of another alternate embodiment of the skin applicator apparatus of the present disclosure.
Figure 56:
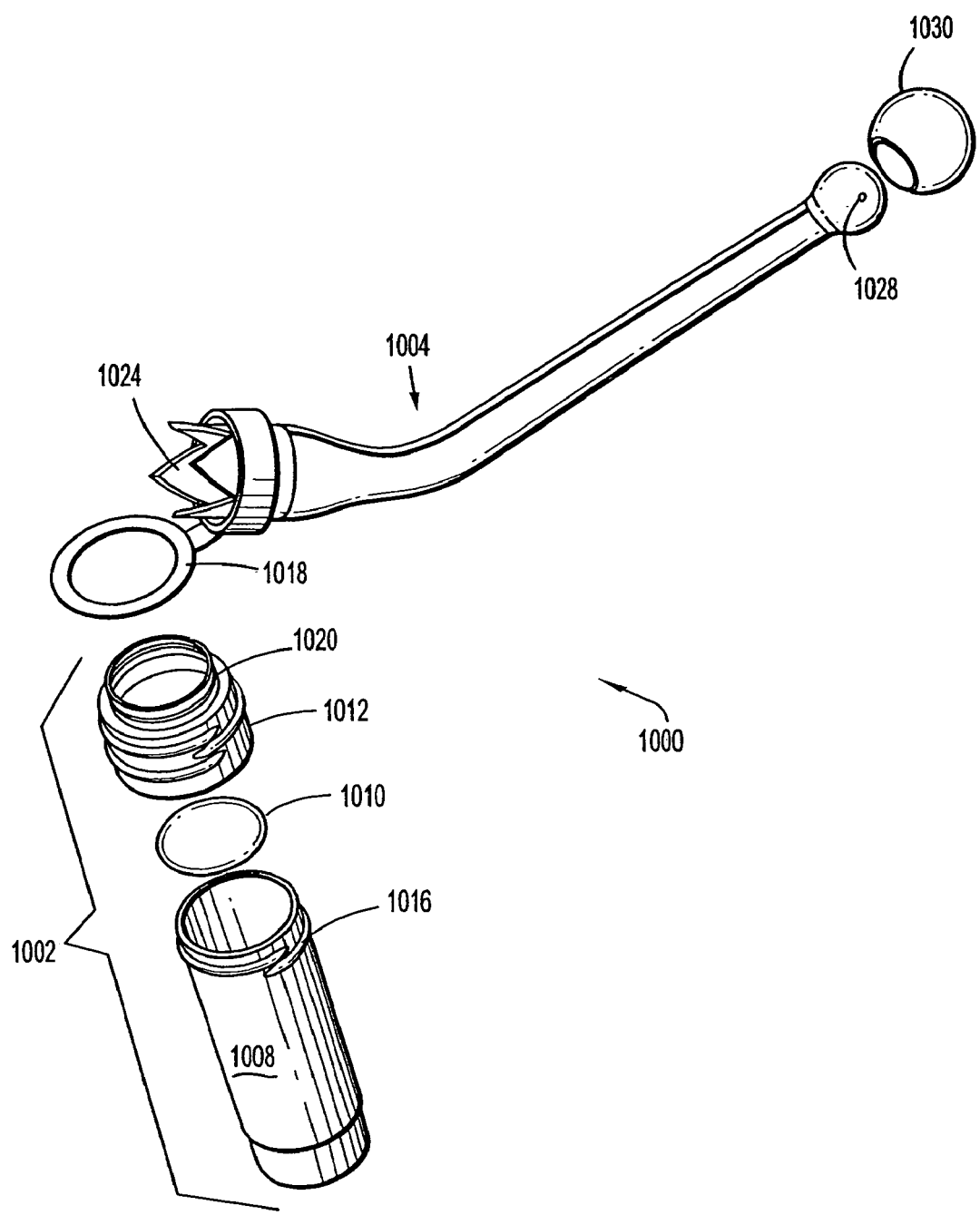
FIG. 56 is an exploded perspective view of the skin applicator apparatus of FIG. 55.
Figure 57:
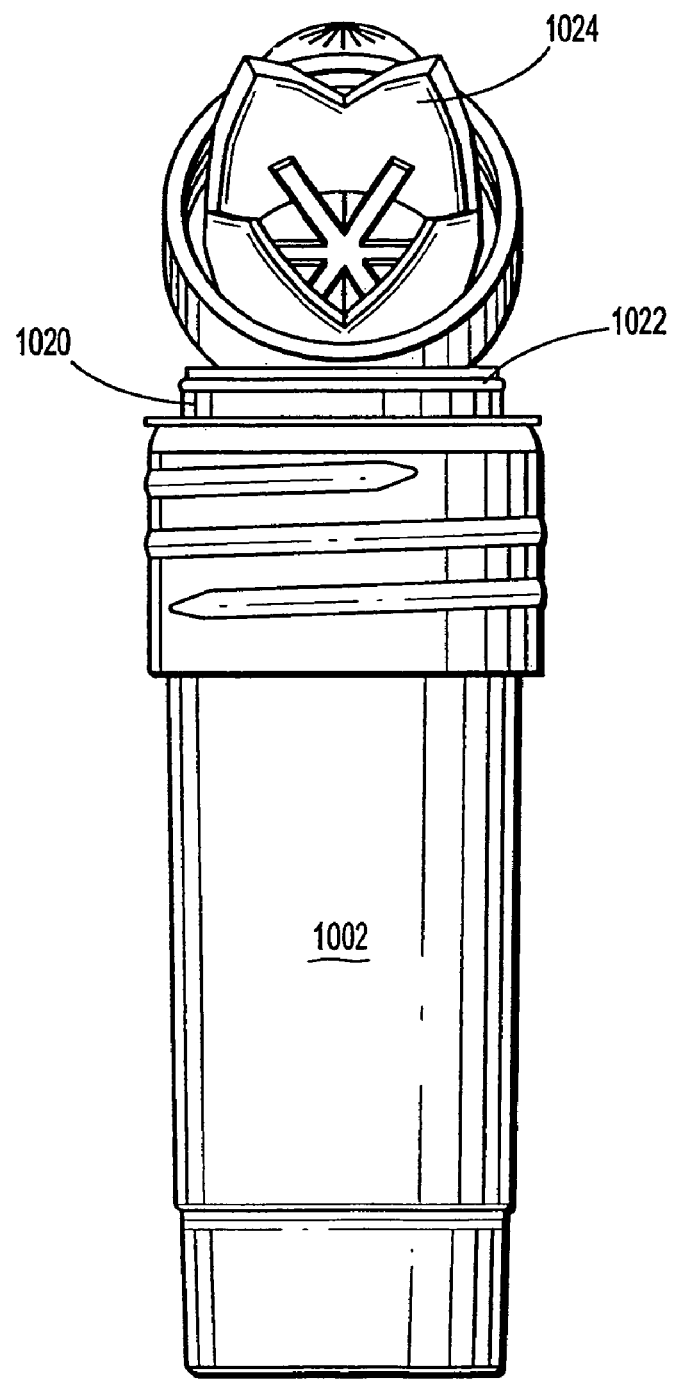
FIG. 57 is another plan view of the skin applicator apparatus of FIG. 55.

FIGS. 52-54 illustrate another alternate embodiment of the present disclosure. Skin applicator apparatus 900 includes an alternate mechanism for severing the foil liner. The mechanism is preferably in the form of a circular array of penetrating members or spikes 902 extending from internal collar 904 of applicator frame 906 which is shown in perspective view in FIG. 52. This circular array is adapted to form a general circular opening within foil liner 908 attached to fluid housing 910. In further accordance with this embodiment, fluid housing 910 is provided with an internal dividing wall 912 extending in a general longitudinal direction. Similarly, internal collar 904 may be provided with longitudinal wall 914. Internal walls 912,914 serve to engage and rotate the wall portion of foil liner 908 severed by the circular array of penetrating members 902 from its original transverse position to a rotated position in general alignment with the longitudinal axis (as shown in FIG. 54) upon movement of fluid housing 910 to the second position of FIG. 54. In this position, the medical agent can flow in an unrestricted manner through applicator frame 906 unimpeded by the severed foil liner 908. Preferably, the internal walls 912, 914 within fluid housing 910 and internal collar 904 of applicator frame 906 are radially displaced or longitudinally misaligned such that the severed wall portion of the foil liner is trapped between the two walls 912,914 upon movement to the second actuated position. In other respects, this embodiment functions in a similar manner to the prior embodiment of FIG. 29.

Figure 58:
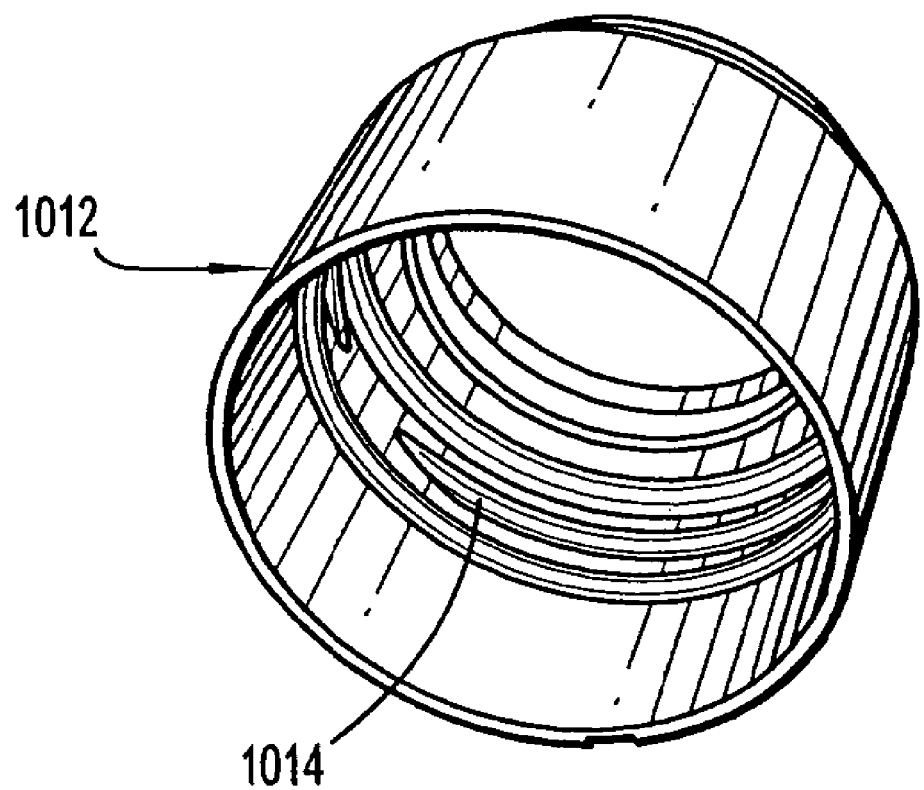
FIG. 58 is a perspective view of the end cap of the skin applicator apparatus of FIG. 55.

Referring now to 55-58, an alternative embodiment in accordance with the principals of the present disclosure is disclosed. Skin applicator apparatus 1000 includes fluid container assembly 1002 which is tethered to the applicator 1004 through a tether line 1006. More specifically, fluid container assembly 1002 includes fluid housing 1008, foil liner 1010 and end cap 1012 which is threadably mounted to fluid housing 1008. End cap 1012 includes internal thread 1014 which threadably engages external thread 1016 (FIG. 58) of fluid housing 1008. Applicator 1004 includes O-ring connector 1018 to which tether 1006 is connected. O-ring connector 1018 is positioned over the neck 1020 of end cap 1012 and retainer therein by circumferential rib 1022 on the exterior of the neck 1020. Applicator 1004 incorporates a circumferential array of penetrating members 1024 similar to the array discussed in the prior embodiment for piercing liner 1010. Applicator 1004 incorporates a plurality of spaced bulbous applicator tip 1026 with a plurality of spaced openings 1028 for dispensing the medical agent. A circular absorbent sponge 1030 may be mounted onto applicator tip 1026. In use, applicator 1004 can be pivoted onto assembly 1002 and secured to the fluid container 1002 through reception of circumferential rib 1022 with annular recess 1032 within applicator 1004. Other means are also envisioned including an interference fit, snap fit, bayonet coupling or the like. Mounting of the applicator 1004 causes the spikes to penetrate the liner thereby activating the apparatus 1000.

It will be understood that various modifications and changes in form and detail may be made to the embodiments of the present disclosure without departing from the spirit and scope of the invention. Therefore, the above description should not be construed as limiting the invention but merely as exemplifications of preferred embodiments thereof. Those skilled in the art will envision other modifications within the scope and spirit of the present invention as defined by the claims appended hereto. Having thus described the invention with the details and particularity required by the patent laws, what is claimed and desired protected is set forth in the appended claims.

What is claimed is:

1. A medical skin applicator apparatus, which comprises:
a fluid housing having a fluid chamber for storing a medical agent and a dye chamber for storing a dye; and
an applicator coupled to the fluid housing, the applicator including an applicator surface for applying the medical agent to a patient, the applicator having a penetrating member adapted to penetrate the fluid housing upon achieving a predetermined coupled relation of the fluid housing and the applicator, to thereby permit the medical agent to be dispensed from the fluid chamber and the dye dispensed from the dye chamber, and applied to the patient with the applicator surface, the fluid housing being adapted to move relative to the applicator from a first transit position to a second actuated position to cause penetration of the penetrating member with the fluid housing to establish the predetermined coupled relation thereof.

2. The medical skin applicator apparatus according to claim 1 wherein the fluid housing is adapted for longitudinal movement to move from the first transit position to the second actuated position.

3. The medical skin applicator apparatus according to claim 2 wherein the dye chamber is isolated from the fluid chamber when the fluid housing is in the first transit position.

4. The medical skin applicator apparatus according to claim 1 including means for retaining the fluid housing in the second actuated position.

5. The medical skin applicator apparatus according to claim 1 including means for retaining the fluid housing in the first transit position.

6. A medical skin applicator apparatus, which comprises:
a fluid housing having a fluid chamber with a medical agent, the fluid housing having a first penetrable wall to permit access to the fluid chamber and release of the medical agent therefrom and a second penetrable wall distal of the first penetrable wall and having dye stored between the first and second penetrable walls; and
an applicator coupled to the fluid housing, the applicator including an applicator surface for applying the medical agent and the dye to a patient, the applicator having a penetrating member, the fluid housing being adapted for longitudinal movement relative to the applicator from a first transit position to a second actuated position to cause penetration of the penetrating member with the first penetrable wall and the second penetrable wall to cause respective release of the medical agent and the dye.

7. The medical skin applicator apparatus according to claim 6 wherein the fluid housing includes a first end cap mounted adjacent the penetrating wall.

8. The medical skin applicator apparatus according to claim 7 wherein the first end cap defines an open portal to permit the penetrating member to pass therethrough and penetrate the first penetrable wall of the fluid housing upon movement of the fluid housing to the second actuated position.

9. The medical skin applicator apparatus according to claim 8 including a second end cap mounted to the first end cap, the dye being disposed within a dye chamber defined between the first and second end caps.

10. The medical skin applicator apparatus according to claim 9 wherein the second end cap is threadably coupled to the first end cap.

11. The medical skin applicator apparatus according to claim 10 wherein the first and second penetrable walls each includes a foil member.

* * * * *